US011306325B2

United States Patent
Gilbert et al.

(10) Patent No.: US 11,306,325 B2
(45) Date of Patent: Apr. 19, 2022

(54) ADENOVIRAL VECTOR

(71) Applicant: Oxford University Innovation Limited, Oxfordshire (GB)

(72) Inventors: Sarah C. Gilbert, Oxfordshire (GB); Adrian V S Hill, Oxfordshire (GB); Matthew G. Cottingham, Oxfordshire (GB); Matthew Dicks, Oxfordshire (GB); Susan J. Morris, Oxfordshire (GB); Alexander Douglas, Oxfordshire (GB)

(73) Assignee: Oxford University Innovation Limited, Oxfordshire (GB)

( * ) Notice: Subject to any disclaimer, the term of this patent is extended or adjusted under 35 U.S.C. 154(b) by 0 days.

(21) Appl. No.: 16/310,281

(22) PCT Filed: Jun. 23, 2017

(86) PCT No.: PCT/GB2017/051851
§ 371 (c)(1),
(2) Date: Dec. 14, 2018

(87) PCT Pub. No.: WO2017/221031
PCT Pub. Date: Dec. 28, 2017

(65) Prior Publication Data
US 2019/0175716 A1    Jun. 13, 2019

(30) Foreign Application Priority Data
Jun. 23, 2016 (GB) ..................... 1610967

(51) Int. Cl.
| A61K 39/00 | (2006.01) |
| C12N 15/86 | (2006.01) |
| C12N 7/00 | (2006.01) |
| A61K 48/00 | (2006.01) |
| A61K 39/12 | (2006.01) |
| C12N 15/861 | (2006.01) |
| A61K 39/235 | (2006.01) |
| A61K 39/145 | (2006.01) |
| A61K 35/761 | (2015.01) |
| A61P 31/16 | (2006.01) |
| A61P 31/06 | (2006.01) |
| A61K 39/04 | (2006.01) |
| A61K 39/21 | (2006.01) |

(52) U.S. Cl.
CPC .......... *C12N 15/861* (2013.01); *A61K 35/761* (2013.01); *A61K 39/12* (2013.01); *A61K 39/145* (2013.01); *A61K 39/235* (2013.01); *A61P 31/16* (2018.01); *C12N 15/86* (2013.01); *C12N 15/8613* (2013.01); *A61K 39/00* (2013.01); *A61K 39/04* (2013.01); *A61K 39/21* (2013.01); *A61P 31/06* (2018.01); *C12N 2710/10044* (2013.01); *C12N 2710/10343* (2013.01); *Y02A 50/30* (2018.01)

(58) Field of Classification Search
CPC . C12N 15/86; C12N 7/00; A61P 35/00; A61P 37/04; A61K 39/12
See application file for complete search history.

(56) References Cited

U.S. PATENT DOCUMENTS

| 2012/0027788 A1 | 2/2012 | Colloca et al. | |
| 2015/0044766 A1* | 2/2015 | Dicks .................... | A61K 48/00 435/320.1 |

FOREIGN PATENT DOCUMENTS

| EP | 3475433 B1 | 7/2021 |
| WO | 2005/071093 | 8/2005 |
| WO | 2012/172277 | 12/2012 |
| WO | WO2012172277 | * 12/2012 |
| WO | 2013/052832 | 4/2013 |
| WO | 2015/052543 | 4/2015 |
| WO | 2015/063647 | 5/2015 |
| WO | 2016/016651 | 2/2016 |

OTHER PUBLICATIONS

Examination Report dated Feb. 21, 2020 for European Patent Application No. 17734440, 8 pages.
Written Opinion dated Apr. 22, 2020 for Singapore Application No. 11201811178U, 6 pages.
Cottingham et al., "Preventing Spontaneous Genetic Rearrangements in the Transgene Cassettes of Adenovirus Vectors", Biotechnology and Bioengineering, Mar. 2012, 109(3), pp. 719-728.
Dicks, et al. "A Novel Chimpanzee Adenovirus Vector with Low Human Seroprevalence: Improved Systems for Vector Derivation and Comparative Immunogenicity", PLoS one, Jul. 2012, 7(7), 12 pages.
Dicks, et al., "The Relative Magnitude of Transgene-Specific Adaptive Immune Responses Induced by Human and Chimpanzee Adenovirus Vectors differs between Laboratory Animals and a Target Species", Vaccine, Jan. 2015, 33, pp. 1121-1128.
Great Britain Patent Application No. 1610967.0, Search Report, dated Mar. 23, 2017, 2 pages.
International Patent Application No. PCT/GB2017/051851, International Search Report, dated Sep. 12, 2017, 6 pages.
International Patent Application No. PCT/GB2017/051851, Written Opinion of the International Searching Authority, dated Sep. 12, 2017, 8 pages.
Kapulu et al., "Comparative Assessment of Transmission-Blocking Vaccine Candidates Against Plasmodium Falciparum", Scientific Reports, Jun. 2015, 5(1), 15 pages.

(Continued)

*Primary Examiner* — Barry A Chestnut
(74) *Attorney, Agent, or Firm* — Morgan, Lewis & Bockius LLP

(57) ABSTRACT

The present invention provides recombinant adenoviral vectors, immunogenic compositions thereof and their uses in medicine. In particular, the present invention provides an adenoviral vector comprising the genome of an adenovirus other than AdHu5 and AdY25, wherein the genome of the adenovirus has been modified such that the vector lacks the native E4 locus of the adenovirus and comprises heterologous E4Orf1, E4Orf2 and E4Orf3 coding regions from AdY25.

21 Claims, 10 Drawing Sheets

Specification includes a Sequence Listing.

(56) References Cited

OTHER PUBLICATIONS

Morris, et al., Simian Adenoviruses as Vaccine Vectors, Future Virology, Sep. 2016, 11 (9), pp. 649-659.

Roshorm et al., "T Cells Induced by Recombinant Chimpanzee Adenovirus Alone and in Prime-boost regimens decrease chimeric EcoHIV/NDK challenge virus load", Eur J Immunol, 2012 42(12), pp. 3243-3255.

Thomas et al., "Effects of the Deletion of Eady Region 4 (E4) Open Reading Frame 1 (orf1), orf1-2, orf1-3 and orf1-4 on Virus-Host Cell Interaction, Transgene Expression, and Immunogenicity of Replicating Adenovirus HIV Vaccine Vectors", PLoS one, Oct. 2013, 8(10), 14 pages.

Buchbinder et al, Efficacy assessment of a cell-mediated immunity HIV-1 vaccine (the Step Study): a double-blind, randomised, placebo-controlled, test-of-concept trial; Lancet, vol. 372, Nov. 2008.

Farina et al Replication-Defective Vector Based on a Chimpanzee Adenovirus; J. Virol, Dec. 2001, p. 11603-11613.

Dudareva et al, Prevalence of serum neutralizing antibodies against chimpanzee adenovirus 63 and human adenovirus 5 in Kenyan children, in the context of vaccine vector efficacy; Vaccine 27, 2009, 3501-3504.

R. Wigand et al, Chimpanzee Adenoviruses Are Related to Four Subgenera of Human Adenoviruses; Intervirology, vol. 30; 1 1989.

Roy et al, Characterization of a family of chimpanzee adenoviruses and development of molecular clones for gene transfer vectors; Hum. Gen. Ther., 2004, 15:519-530.

The trusted leader in cloning technology; http://www.invitrogen.com/gateway.

Havenga et al, Novel replication-incompetent adenoviral B-group vectors: high vector stability and yield in PER.C6 cells; J.G.V., 2006, 87, 2135-214.

Warming, S., et al., Simple and highly efficient BAC recombineering using galK selection; Nucleic Acids Res, Feb. 24, 2005; 33(4): e36.

Colloca, S., et al., Vaccine vectors derived from a large collection of simian adenoviruses induce potent cellular immunity across multiple species; Sci Transl Med, 2012. 4(115): p. 115ra2.

Quinn, K.M., et al. Comparative Analysis of the Magnitude, Quality, Phenotype, and Protective Capacity of Simian Immunodeficiency Virus Gag-Specific CD8 + T Cells following Human-, Simian-, and Chimpanzee-Derived Recombinant Adenoviral Vector Immunization; J Immunol, 2013. 190(6): p. 2720-2735.

Extended European Search Report dated Dec. 17, 2021 for European Patent Application No. 21182840.5, 15 pages.

Office Action dated Nov. 10, 2021 for Mexican Patent Application No. MX/a/2018/016074, 9 pages.

\* cited by examiner

Table 1.

| Group | ChAdOx2 HAV dose |
|---|---|
| 1 (n=3) | $5 \times 10^9$ vp |
| 2 (n=3) | $2.5 \times 10^{10}$ vp |
| 3 (n=3-6) | $5 \times 10^{10}$ vp |

Table 2.

ChAdOx2 HAV

| | Participant | D0 | D2 | D7 | D14 | D28 | D56 | D364 |
|---|---|---|---|---|---|---|---|---|
| Group 1 | 00101002 | 15/03/2017 | 17/03/2017 | 22/03/2017 | 29/03/2017 | 12/04/2017 | 10/05/2017 | 14/03/2018 |
| | 00101003 | 21/03/2017 | 23/03/2017 | 28/03/2017 | 04/04/2017 | 18/04/2017 | 16/05/2017 | 20/03/2018 |
| | 00101005 | 21/03/2017 | 23/03/2017 | 28/03/2017 | 04/04/2017 | 18/04/2017 | 16/05/2017 | 20/03/2018 |
| Group 2 | 00101004 | 04/04/2017 | 06/04/2017 | 11/04/2017 | 18/04/2017 | 02/05/2017 | 30/05/2017 | 03/04/2018 |
| | 00101006 | 11/04/2017 | 13/04/2017 | 18/04/2017 | 25/04/2017 | 09/05/2017 | 06/06/2017 | 10/04/2018 |
| | 00101008 | 11/04/2017 | 13/04/2017 | 18/04/2017 | 25/04/2017 | 09/05/2017 | 06/06/2017 | 10/04/2018 |
| Group 3 | 00101011 | 17/05/2017 | 19/05/2017 | 24/05/2017 | 31/05/2017 | 14/06/2017 | 12/07/2017 | 16/05/2018 |
| | 00101018 | 23/05/2017 | 25/05/2017 | 30/05/2017 | 06/06/2017 | 20/06/2017 | 18/07/2017 | 22/05/2018 |
| | 00101010 | 24/05/2017 | 26/05/2017 | 31/05/2017 | 07/06/2017 | 21/06/2017 | 19/07/2017 | 23/05/2018 |

|         |       |              | SFC per million PBMC |        |       |
|---------|-------|--------------|------|--------|-------|
| Patient | Group | Dose (v.p.)  | D0   | D28    | D56   |
| 002     |       |              | 82.7 | 65.3   | 36.0  |
| 003     | 1     | $5 \times 10^9$ | 248.0 | 38.7 | 104.0 |
| 005     |       |              | 80.0 | 128.0  | 40.0  |
| 004     |       |              | 61.3 | 1701.3 | 624.0 |
| 006     | 2     | $2.5 \times 10^{10}$ | 104.0 | 1033.3 | |
| 008     |       |              | 24.7 | 534.7  |       |
| 010     |       |              | 233.3 |       |       |
| 011     | 3     | $5 \times 10^{10}$ | 129.3 |  |   |
| 018     |       |              | 178.7 |       |       |

SEQUENCE LISTING

<160> NUMBER OF SEQ ID NOS: 21

<210> SEQ ID NO 1
<211> LENGTH: 36519
<212> TYPE: DNA
<213> ORGANISM: Chimpanzee adenovirus C68

<400> SEQUENCE: 1

| | | | | | |
|---|---|---|---|---|---|
| ccatcttcaa | taatatacct | caaactttt | gtgcgcgtta | atatgcaaat | gaggcgtttg | 60 |
| aatttgggga | ggaagggcgg | tgattggtcg | agggatgagc | gaccgttagg | ggcggggcga | 120 |
| gtgacgtttt | gatgacgtgg | ttgcgaggag | gagccagttt | gcaagttctc | gtgggaaaag | 180 |
| tgacgtcaaa | cgaggtgtgg | tttgaacacg | gaaatactca | attttcccgc | gctctctgac | 240 |
| aggaaatgag | gtgtttctgg | gcggatgcaa | gtgaaaacgg | gccattttcg | cgcgaaaact | 300 |
| gaatgaggaa | gtgaaaatct | gagtaatttc | gcgtttatgg | cagggaggag | tatttgccga | 360 |
| gggccgagta | gactttgacc | gattacgtgg | gggtttcgat | taccgtgttt | ttcacctaaa | 420 |
| tttccgcgta | cggtgtcaaa | gtccggtgtt | tttacgtagg | tgtcagctga | tcgccagggt | 480 |
| atttaaacct | gcgctctcca | gtcaagaggc | cactcttgag | tgccagcgag | aagagttttc | 540 |
| tcctccgcgc | cgcgagtcag | atctacactt | tgaaagatga | ggcacctgag | agacctgccc | 600 |
| gatgagaaaa | tcatcatcgc | ttccgggaac | gagattctgg | aactggtggt | aaatgccatg | 660 |
| atgggcgacg | accctccgga | gccccccacc | ccatttgaga | caccttcgct | gcacgatttg | 720 |
| tatgatctgg | aggtggatgt | gcccgaggac | gatcccaatg | aggaggcggt | aaatgatttt | 780 |
| tttagcgatg | ccgcgctgct | agctgccgag | gaggcttcga | gctctagctc | agacagcgac | 840 |
| tcttcactgc | atacccctag | acccggcaga | ggtgagaaaa | agatccccga | gcttaaaggg | 900 |
| gaagagatgg | acttgcgctg | ctatgaggaa | tgcttgcccc | cgagcgatga | tgaggacgag | 960 |
| caggcgatcc | agaacgcagc | gagccaggga | gtgcaagccg | ccagcgagag | ctttgcgctg | 1020 |
| gactgcccgc | ctctgcccgg | acacggctgt | aagtcttgtg | aatttcatcg | catgaatact | 1080 |
| ggagataaag | ctgtgttgtg | tgcactttgc | tatatgagag | cttacaacca | ttgtgtttac | 1140 |
| agtaagtgtg | attaagttga | actttagagg | gaggcagaga | gcagggtgac | tgggcgatga | 1200 |
| ctggtttatt | tatgtatata | tgttctttat | ataggtcccg | tctctgacgc | agatgatgag | 1260 |
| accccacta | caaagtccac | ttcgtcaccc | ccagaaattg | gcacatctcc | acctgagaat | 1320 |
| attgttagac | cagttcctgt | tagagccact | gggaggagag | cagctgtgga | atgtttggat | 1380 |
| gacttgctac | agggtgggt | tgaacctttg | gacttgtgta | cccggaaacg | ccccaggcac | 1440 |
| taagtgccac | acatgtgtgt | ttacttgagg | tgatgtcagt | atttataggg | tgtggagtgc | 1500 |
| aataaaaat | gtgttgactt | taagtgcgtg | gtttatgact | caggggtggg | gactgtgagt | 1560 |
| atataagcag | gtgcagacct | gtgtggttag | ctcagagcgg | catggagatt | tggacggtct | 1620 |
| tggaagactt | tcacaagact | agacagctgc | tagagaacgc | ctcgaacgga | gtctcttacc | 1680 |
| tgtggagatt | ctgcttcggt | ggcgacctag | ctaggctagt | ctacagggcc | aaacaggatt | 1740 |
| atagtgaaca | atttgaggtt | attttgagag | agtgttctgg | tcttttttgac | gctcttaact | 1800 |
| tgggccatca | gtctcacttt | aaccagagga | tttcgagagc | ccttgatttt | actactcctg | 1860 |
| gcagaaccac | tgcagcagta | gccttttttg | cttttattct | tgacaaatgg | agtcaagaaa | 1920 |
| cccatttcag | cagggattac | cagctggatt | tcttagcagt | agctttgtgg | agaacatgga | 1980 |
| agtgccagcg | cctgaatgca | atctccggct | acttgccggt | acagccgcta | gacactctga | 2040 |
| ggatcctgaa | tctccaggag | agtcccaggg | cacgccaacg | tcgccagcag | cagcagcagg | 2100 |

```
aggaggatca agaagagaac ccgagagccg gcctggaccc tccggcggag gaggaggagt   2160
agctgacctg tttcctgaac tgcgccgggt gctgactagg tcttcgagtg gtcgggagag   2220
ggggattaag cgggagaggc atgatgagac taatcacaga actgaactga ctgtgggtct   2280
gatgagtcgc aagcgcccag aaacagtgtg gtggcatgag gtgcagtcga ctggcacaga   2340
tgaggtgtcg gtgatgcatg agaggttttc tctagaacaa gtcaagactt gttggttaga   2400
gcctgaggat gattgggagg tagccatcag gaattatgcc aagctggctc tgaggccaga   2460
caagaagtac aagattacta agctgataaa tatcagaaat gcctgctaca tctcagggaa   2520
tggggctgaa gtggagatct gtctccagga aagggtggct ttcagatgct gcatgatgaa   2580
tatgtacccg ggagtggtgg gcatggatgg ggttaccttt atgaacatga ggttcagggg   2640
agatgggtat aatggcacgg tctttatggc caataccaag ctgacagtcc atggctgctc   2700
cttctttggg tttaataaca cctgcatcga ggcctggggt caggtcggtg tgaggggctg   2760
cagtttttca gccaactgga tggggtcgt gggcaggacc aagagtatgc tgtccgtgaa   2820
gaaatgcttg tttgagaggt gccacctggg ggtgatgagc gagggcgaag ccagaatccg   2880
ccactgcgcc tctaccgaga cgggctgctt tgtgctgtgc aagggcaatg ctaagatcaa   2940
gcataatatg atctgtggag cctcggacga gcgcggctac cagatgctga cctgcgccgg   3000
cgggaacagc catatgctgg ccaccgtaca tgtggcttcc catgctcgca gccctggcc   3060 cgagttcgag cacaatgtca tgaccaggtg caatatgcat ctggggtccc gccgaggcat   3120
gttcatgccc taccagtgca acctgaatta tgtgaaggtg ctgctggagc ccgatgccat   3180
gtccagagtg agcctgacgg gggtgtttga catgaatgtg gaggtgtgga agattctgag   3240
atatgatgaa tccaagacca ggtgccgagc ctgcgagtgc ggaggaagc atgccaggtt   3300 ccagcccgtg tgtgtggatg tgacggagga cctgcgaccc gatcatttgg tgttgccctg   3360
caccgggacg gagttcggtt ccagcgggga agaatctgac tagagtgagt agtgttctgg   3420 ggcggggag gacctgcatg agggccagaa taactgaaat ctgtgctttt ctgtgtgttg   3480
cagcagcatg agcggaagcg gctcctttga gggaggggta ttcagcccctt atctgacggg   3540 gcgtctcccc tcctgggcgg gagtgcgtca gaatgtgatg ggatccacgg tggacggccg   3600
gcccgtgcag cccgcgaact cttcaaccct gacctatgca accctgagct cttcgtcgtt   3660
ggacgcagct gccgccgcag ctgctgcatc tgccgccagc gccgtgcgcg gaatggccat   3720
gggcgccggc tactacggca ctctggtggc caactcgagt tccaccaata atcccgccag   3780
cctgaacgag gagaagctgt tgctgctgat ggcccagctc gaggccttga cccagcgcct   3840
gggcgagctg acccagcagg tggctcagct gcaggagcag acgcgggccg cggttgccac   3900
ggtgaaatcc aaataaaaaa tgaatcaata aataaacgga gacggttgtt gattttaaca   3960
cagagtctga atctttattt gattttcgc gcgcggtagg ccctggacca ccggtctcga   4020
tcattgagca cccggtggat cttttccagg accggtagaa ggtgggcttg gatgttgagg   4080
tacatgggca tgagcccgtc ccgggggtgg aggtagctcc attgcagggc ctcgtgctcg   4140
ggggtggtgt tgtaaatcac ccagtcatag caggggcgca gggcatggtg ttgcacaata   4200
tctttgagga ggagactgat ggccacgggc agcccttggg tgtaggtgtt tacaaatctg   4260
ttgagctggg agggatgcat gcgggggag atgaggtgca tcttggcctg gatcttgaga   4320
ttggcgatgt taccgcccag atcccgcctg gggttcatgt tgtgcaggac caccagcacg   4380
gtgtatccgg tgcacttggg gaatttatca tgcaacttgg aagggaaggc gtgaaagaat   4440
```

```
ttggcgacgc ctttgtgccc gcccaggttt tccatgcact catccatgat gatggcgatg    4500
ggcccgtggg cggcggcctg ggcaaagacg tttcggggt cggacacatc atagttgtgg     4560
tcctgggtga ggtcatcata ggccatttta atgaatttgg ggcggagggt gccggactgg    4620
gggacaaagg taccctcgat cccgggggcg tagttcccct cacagatctg catctcccag    4680
gctttgagct cggaggggg gatcatgtcc acctgcgggg cgataaagaa cacggtttcc     4740
ggggcggggg agatgagctg ggccgaaagc aagttccgga gcagctggga cttgccgcag    4800
ccggtggggc cgtagatgac cccgatgacc ggctgcaggt ggtagttgag ggagagacag    4860
ctgccgtcct cccggaggag gggggccacc tcgttcatca tctcgcgcac gtgcatgttc    4920
tcgcgcacca gttccgccag gaggcgctct ccccccaggg ataggagctc ctggagcgag    4980
gcgaagtttt tcagcggctt gagtccgtcg gccatgggca ttttggagag gtttgttgc     5040 aagagttcca ggcggtccca gagctcggtg atgtgctcta cggcatctcg atccagcaga    5100
cctcctcgtt tcgcgggttg ggacggctgc gggagtaggg caccagacga tgggcgtcca    5160
gcgcagccag ggtccggtcc ttccagggtc gcagcgtccg cgtcagggtg gtctccgtca    5220
cggtgaaggg gtgcgcgccg ggctgggcgc ttgcgagggt gcgcttcagg ctcatccggc    5280
tggtcgaaaa ccgctcccga tcggcgccct gcgcgtcggc caggtagcaa ttgaccatga    5340
gttcgtagtt gagcgcctcg gccgcgtggc ctttggcgcg gagcttacct ttggaagtct    5400
gcccgcaggc gggacagagg agggacttga gggcgtagag cttggggcg aggaagacgg     5460 actcgggggc gtaggcgtcc gcgccgcagt gggcgcagac ggtctcgcac tccacgagcc    5520
aggtgaggtc gggctggtcg gggtcaaaaa ccagtttccc gccgttcttt ttgatgcgtt    5580
tcttaccttt ggtctccatg agctcgtgtc cccgctgggt gacaaagagg ctgtccgtgt    5640
ccccgtagac cgactttatg ggccggtcct cgagcggtgt gccgcggtcc tcctcgtaga    5700
ggaaccccgc ccactccgag acgaaagccc gggtccaggc cagcacgaag gaggccacgt    5760
gggacgggta gcgtcgttg tccaccagcg ggtccacctt ttccagggta tgcaaacaca     5820
tgtccccctc gtccacatcc aggaaggtga ttggcttgta agtgtaggcc acgtgaccgg    5880
gggtcccggc cggggggta taaaagggtg cgggtccctg ctcgtcctca ctgtcttccg     5940
gatcgctgtc caggagcgcc agctgttggg gtaggtattc cctctcgaag gcgggcatga    6000
cctcggcact caggttgtca gtttctagaa acgaggagga tttgatattg acggtgccgg    6060
cggagatgcc tttcaagagc ccctcgtcca tctggtcaga aaagacgatc ttttttgttgt   6120 cgagcttggt ggcgaaggag ccgtagaggg cgttggagag gagcttggcg atggagcgca    6180
tggtctggtt tttttccttg tcggcgcgct ccttggcggc gatgttgagc tgcacgtact    6240
cgcgcgccac gcacttccat tcggggaaga cggtggtcag ctcgtcgggc acgattctga    6300
cctgccagcc ccgattatgc aggtgatga ggtccacact ggtggccacc tcgccgcgca     6360
ggggctcatt agtccagcag aggcgtccgc ccttgcgcga gcagaagggg ggcaggggt     6420 ccagcatgac ctcgtcgggg gggtcggcat cgatggtgaa gatgccgggc aggaggtcgg    6480
ggtcaaagta gctgatggaa gtggccagat cgtccagggc agcttgccat tcgcgcacgg    6540
ccagcgcgcg ctcgtaggga ctgaggggcg tgccccaggg catgggatgg gtaagcgcgg    6600
aggcgtacat gccgcagatg tcgtagacgt agaggggctc ctcgaggatg ccgatgtagg    6660
tggggtagca gcgccccccg cggatgctgg cgcgcacgta gtcatacagc tcgtgcgagg    6720
gggcgaggag cccggccc aggttggtgc gactgggctt tcggcgcgg tagacgatct       6780 ggcggaaaat ggcatgcgag ttggaggaga tggtgggcct ttggaagatg ttgaagtggg    6840
```

```
cgtggggcag tccgaccgag tcgcggatga agtgggcgta ggagtcttgc agcttggcga    6900
cgagctcggc ggtgactagg acgtccagag cgcagtagtc gagggtctcc tggatgatgt    6960
catacttgag ctgtcccttt tgtttccaca gctcgcggtt gagaaggaac tcttcgcggt    7020
ccttccagta ctcttcgagg gggaacccgt cctgatctgc acggtaagag cctagcatgt    7080
agaactggtt gacggccttg taggcgcagc agcccttctc cacggggagg gcgtaggcct    7140
gggcggcctt gcgcagggag gtgtgcgtga gggcgaaagt gtccctgacc atgaccttga    7200
ggaactggtg cttgaagtcg atatcgtcgc agccccctg ctcccagagc tggaagtccg     7260
tgcgcttctt gtaggcgggg ttgggcaaag cgaaagtaac atcgttgaag aggatcttgc    7320
ccgcgcgggg cataaagttg cgagtgatgc ggaaaggttg gggcacctcg gcccggttgt    7380
tgatgacctg ggcggcgagc acgatctcgt cgaagccgtt gatgttgtgg cccacgatgt    7440
agagttccac gaatcgcgga cggcccttga cgtggggcag tttcttgagc tcctcgtagg    7500
tgagctcgtc ggggtcgctg agcccgtgct gctcgagcgc ccagtcggcg agatgggggt    7560
tggcgcggag gaaggaagtc cagagatcca cggccagggc ggtttgcaga cggtcccggt    7620
actgacggaa ctgctgcccg acggccattt tttcggggt gacgcagtag aaggtgcggg     7680
ggtccccgtg ccagcgatcc catttgagct ggagggcgag atcgagggcg agctcgacga    7740
gccggtcgtc cccggagagt ttcatgacca gcatgaaggg gacgagctgc ttgccgaagg    7800
acccccatcca ggtgtaggtt tccacatcgt aggtgaggaa gagcctttcg gtgcgaggat   7860
gcgagccgat ggggaagaac tggatctcct gccaccaatt ggaggaatgg ctgttgatgt    7920
gatggaagta gaaatgccga cggcgcgccg aacactcgtg cttgtgttta tacaagcggc    7980
cacagtgctc gcaacgctgc acgggatgca cgtgctgcac gagctgtacc tgagttcctt    8040
tgacgaggaa tttcagtggg aagtggagtc gtggcgcctg catctcgtgc tgtactacgt    8100
cgtggtggtc ggcctggccc tcttctgcct cgatggtggt catgctgacg agcccgcgcg    8160
ggaggcaggt ccagacctcg gcgcgagcgg gtcggagagc gaggacgagg gcgcgcaggc    8220
cggagctgtc cagggtcctg agacgctgcg gagtcaggtc agtgggcagc ggcggcgcgc    8280
ggttgacttg caggagtttt tccagggcgc gcggaggtc cagatggtac ttgatctcca     8340
ccgcgccatt ggtggcgacg tcgatggctt gcagggtccc gtgcccctgg ggtgtgacca    8400
ccgtcccccg tttcttcttg ggcggctggg gcgacggggg cggtgcctct tccatggtta    8460
gaagcggcgg cgaggacgcg cgccgggcgg caggggcggc tcggggcccg gaggcagggg    8520
cggcaggggc acgtcggcgc cgcgcgcggg taggttctgg tactgcgccc ggagaagact    8580
ggcgtgagcg acgacgcgac ggttgacgtc ctggatctga cgcctctggg tgaaggccac    8640
gggacccgtg agtttgaacc tgaaagagag ttcgacagaa tcaatctcgg tatcgttgac    8700
ggcggcctgc cgcaggatct cttgcacgtc gcccgagttg tcctggtagg cgatctcggt    8760
catgaactgc tcgatctcct cctcttgaag gtctccgcgg ccggcgcgct ccacggtggc    8820
cgcgaggtcg ttggagatgc ggcccatgag ctgcgagaag gcgttcatgc ccgcctcgtt    8880
ccagacgcgg ctgtagacca cgacgccctc gggatcgccg gcgcgcatga ccacctgggc    8940
gaggttgagc tccacgtggc gcgtgaagac cgcgtagttg cagaggcgct ggtagaggta    9000
gttgagcgtg gtggcgatgt gctcggtgac gaagaaatac atgatccagc ggcggagcgg    9060
catctcgctg acgtcgccca gcgcctccaa acgttccatg gcctcgtaaa agtccacggc    9120
gaagttgaaa aactgggagt tgcgcgccga gacggtcaac tcctcctcca gaagacggat    9180
```

```
gagctcggcg atggtggcgc gcacctcgcg ctcgaaggcc cccgggagtt cctccacttc    9240
ctcttcttcc tcctccacta acatctcttc tacttcctcc tcaggcggca gtggtggcgg    9300 gggaggggc ctgcgtcgcc ggcggcgcac gggcagacgg tcgatgaagc gctcgatggt    9360
ctcgccgcgc cggcgtcgca tggtctcggt gacggcgcgc ccgtcctcgc ggggccgcag    9420
cgtgaagacg ccgccgcgca tctccaggtg gccggggggg tccccgttgg gcagggagag    9480
ggcgctgacg atgcatctta tcaattgccc cgtagggact ccgcgcaagg acctgagcgt    9540
ctcgagatcc acgggatctg aaaaccgctg aacgaaggct tcgagccagt cgcagtcgca    9600
aggtaggctg agcacggttt cttctggcgg gtcatgttgg ttgggagcgg ggcgggcgat    9660
gctgctggtg atgaagttga ataggcggt tctgagacgg cggatggtgg cgaggagcac    9720
caggtctttg ggcccggctt gctggatgcg cagacggtcg gccatgcccc aggcgtggtc    9780
ctgacacctg gccaggtcct tgtagtagtc ctgcatgagc cgctccacgg gcacctcctc    9840
ctcgcccgcg cggccgtgca tgcgcgtgag cccgaagccg cgctgggct ggacgagcgc    9900 caggtcggcg acgacgcgct cggcgaggat ggcttgctgg atctgggtga gggtggtctg    9960
gaagtcatca aagtcgacga agcggtggta ggctccggtg ttgatggtgt aggagcagtt   10020
ggccatgacg gaccagttga cggtctggtg gcccggacgc acgagctcgt ggtacttgag   10080
gcgcgagtag gcgcgcgtgt cgaagatgta gtcgttgcag gtgcgcacca ggtactggta   10140
gccgatgagg aagtgcggcg gcggctggcg gtagagcggc catcgctcgg tggcggggc    10200 gccgggcgcg aggtcctcga gcatggtgcg gtggtagccg tagatgtacc tggacatcca   10260
ggtgatgccg gcggcggtgg tggaggcgcg cgggaactcg cggacgcggt tccagatgtt   10320
gcgcagcggc aggaagtagt tcatggtggg cacggtctgg cccgtgaggc gcgcgcagtc   10380
gtggatgctc tatacgggca aaaacgaaag cggtcagcgg ctcgactccg tggcctggag   10440
gctaagcgaa cgggttgggc tgcgcgtgta ccccggttcg aatctcgaat caggctggag   10500
ccgcagctaa cgtggtattg gcactcccgt ctcgacccaa gcctgcacca accctccagg   10560
atacggaggc gggtcgtttt gcaacttttt tttggaggcc ggatgagact agtaagcgcg   10620
gaaagcggcc gaccgcgatg gctcgctgcc gtagtctgga gaagaatcgc cagggttgcg   10680
ttgcggtgtg ccccggttcg aggccggccg gattcgcgg ctaacgaggg cgtggctgcc   10740
ccgtcgtttc caagaccccca tagccagccg acttctccag ttacggagcg agccctctt    10800 ttgttttgtt tgttttttgcc agatgcatcc cgtactgcgg cagatgcgcc cccaccaccc   10860
tccaccgcaa caacagcccc ctccacagcc ggcgcttctg ccccccgcccc agcagcaact   10920 tccagccacg accgccgcgg ccgccgtgag cggggctgga cagagttatg atcaccagct   10980
ggccttggaa gagggcgagg ggctggcgcg cctgggggcg tcgtcgccgg agcggcaccc   11040
gcgcgtgcag atgaaaaggg acgctcgcga ggcctacgtg cccaagcaga acctgttcag   11100
agacaggagc ggcgaggagc ccgaggagat gcgcgcggcc cggttccacg cggggcggga   11160
gctgcggcgc ggcctggacc gaaagagggt gctgagggac gaggatttcg aggcggacga   11220
gctgacgggg atcagccccg cgcgcgcgca cgtggccgcg gccaacctgg tcacggcgta   11280
cgagcagacc gtgaaggagg agagcaactt ccaaaaatcc ttcaacaacc acgtgcgcac   11340
cctgatcgcg cgcgaggagg tgaccctggg cctgatgcac ctgtgggacc tgctggaggc   11400
catcgtgcag aaccccacca gcaagccgct gacggcgcag ctgttcctgg tggtgcagca   11460 tagtcggac aacgaagcgt tcaggagcg gctgctgaat atcaccgagc ccgagggccg    11520
ctggctcctg gacctggtga acattctgca gagcatcgtg gtgcaggagc gcgggctgcc   11580
```

```
gctgtccgag aagctggcgg ccatcaactt ctcggtgctg agtttgggca agtactacgc  11640
taggaagatc tacaagaccc cgtacgtgcc catagacaag gaggtgaaga tcgacgggtt  11700
ttacatgcgc atgaccctga aagtgctgac cctgagcgac gatctggggg tgtaccgcaa  11760
cgacaggatg caccgtgcgg tgagcgccag caggcggcgc gagctgagcg accaggagct  11820
gatgcatagt ctgcagcggg ccctgaccgg ggccgggacc gaggggggaga gctactttga  11880
catgggcgcg gacctgcact ggcagcccag ccgccgggcc ttggaggcgg cggcaggacc  11940
ctacgtagaa gaggtggacg atgaggtgga cgaggagggc gagtacctgg aagactgatg  12000
gcgcgaccgt attttttgcta gatgcaacaa caacagccac ctcctgatcc cgcgatgcgg  12060
gcggcgctgc agagccagcc gtccggcatt aactcctcgg acgattggac ccaggccatg  12120
caacgcatca tggcgctgac gacccgcaac cccgaagcct ttagacagca gccccaggcc  12180
aaccggctct cggccatcct ggaggccgtg gtgccctcgc gctccaaccc cacgcacgag  12240
aaggtcctgg ccatcgtgaa cgcgctggtg gagaacaagg ccatccgcgg cgacgaggcc  12300
ggcctggtgt acaacgcgct gctggagcgc gtggcccgct acaacagcac caacgtgcag  12360
accaacctgg accgcatggt gaccgacgtg cgcgaggccg tgcccagcg cgagcggttc  12420
caccgcgagt ccaacctggg atccatggtg cgctgaacg ccttcctcag cacccagccc  12480
gccaacgtgc cccggggcca ggaggactac accaacttca tcagcgccct gcgcctgatg  12540
gtgaccgagg tgccccagag cgaggtgtac cagtccgggc cggactactt cttccagacc  12600
agtcgccagg gcttgcagac cgtgaacctg agccaggctt tcaagaactt gcagggcctg  12660
tggggcgtgc aggccccggt cggggaccgc gcgacggtgt cgagcctgct gacgccgaac  12720
tcgcgcctgc tgctgctgct ggtggccccc ttcacggaca gcggcagcat caaccgcaac  12780
tcgtacctgg gctacctgat taacctgtac cgcgaggcca tcggccaggc gcacgtggac  12840
gagcagacct accaggagat cacccacgtg agccgcgccc tgggccagga cgacccgggc  12900
aacctggaag ccaccctgaa cttttttgctg accaaccggt cgcagaagat cccgcccag  12960
tacgcgctca gcaccgagga ggagcgcatc ctgcgttacg tgcagcagag cgtgggcctg  13020
ttcctgatgc aggaggggc cacccccagc gccgcgctcg acatgaccgc gcgcaacatg  13080
gagcccagca tgtacgccag caaccgcccg ttcatcaata aactgatgga ctacttgcat  13140
cgggcggccg ccatgaactc tgactatttc accaacgcca tcctgaatcc ccactggctc  13200
ccgccgccgg ggttctacac gggcgagtac gacatgcccg accccaatga cgggttcctg  13260
tgggacgatg tggacagcag cgtgttctcc ccccgaccgg gtgctaacga gcgccccttg  13320
tggaagaagg aaggcagcga ccgacgcccg tcctcggcgc tgtccggccg cgagggtgct  13380
gccgcggcgg tgcccgaggc cgccagtcct ttcccgagct tgcccttctc gctgaacagt  13440
atccgcagca gcgagctggg caggatcacg cgcccgcgct tgctgggcga agaggagtac  13500
ttgaatgact cgctgttgag acccgagcgg gagaagaact tccccaataa cgggatagaa  13560
agcctggtgg acaagatgag ccgctggaag acgtatgcgc aggagcacag ggacgatccc  13620
cgggcgtcgc aggggccac gagccggggc agcgccgccc gtaaacgccg gtggcacgac  13680
aggcagcggg gacagatgtg ggacgatgag gactccgccg acgacagcag cgtgttggac  13740
ttgggtggga gtggtaaccc gttcgctcac ctgcgccccc gtatcgggcg catgatgtaa  13800
gagaaaccga aaataaatga tactcaccaa ggccatggcg accagcgtgc gttcgtttct  13860
tctctgttgt tgttgtatct agtatgatga ggcgtgcgta cccggagggt cctcctcccct  13920
```

```
cgtacgagag cgtgatgcag caggcgatgg cggcggcggc gatgcagccc ccgctggagg   13980
ctccttacgt gccccgcgg tacctggcgc tacggaggg gcggaacagc attcgttact      14040
cggagctggc acccttgtac gataccaccc ggttgtacct ggtggacaac aagtcggcgg    14100
acatcgcctc gctgaactac cagaacgacc acagcaactt cctgaccacc gtggtgcaga    14160
acaatgactt cacccccacg gaggccagca cccagaccat caactttgac gagcgctcgc    14220
ggtggggcgg ccagctgaaa accatcatgc acaccaacat gcccaacgtg aacgagttca    14280
tgtacagcaa caagttcaag gcgcgggtga tggtctcccg caagaccccc aatgggtga     14340 cagtgacaga ggattatgat ggtagtcagg atgagctgaa gtatgaatgg gtggaatttg    14400
agctgcccga aggcaacttc tcggtgacca tgaccatcga cctgatgaac aacgccatca    14460
tcgacaatta cttggcggtg gggcggcaga acggggtgct ggagagcgac atcgcgtga     14520 agttcgacac taggaacttc aggctgggct gggaccccgt gaccgagctg gtcatgcccg    14580
gggtgtacac caacgaggct ttccatcccg atattgtctt gctgcccggc tgcggggtgg    14640
acttcaccga gagccgcctc agcaacctgc tgggcattcg caagaggcag cccttccagg    14700
aaggcttcca gatcatgtac gaggatctgg aggggggcaa catccccgcg ctcctggatg    14760
tcgacgccta tgagaaaagc aaggaggatg cagcagctga agcaactgca gccgtagcta    14820
ccgcctctac cgaggtcagg ggcgataatt ttgcaagcgc cgcagcagtg gcagcggccg    14880
aggcggctga aaccgaaagt aagatagtca ttcagccggt ggagaaggat agcaagaaca    14940
ggagctacaa cgtactaccg gacaagataa acaccgccta ccgcagctgg tacctagcct    15000
acaactatgg cgaccccgag aagggcgtgc gctcctggac gctgctcacc acctcggacg    15060
tcacctgcgg cgtggagcaa gtctactggt cgctgcccga catgatgcaa gacccggtca    15120
ccttccgctc cacgcgtcaa gttagcaact accggtggt gggcgccgag ctcctgcccg     15180
tctactccaa gagcttcttc aacgagcagg ccgtctactc gcagcagctg cgcgccttca    15240 cctgcttac gcacgtcttc aaccgcttcc ccgagaacca gatcctcgtc cgcccgcccg    15300
cgcccaccat taccaccgtc agtgaaaacg ttcctgctct cacagatcac gggaccctgc    15360
cgctgcgcag cagtatccgg ggagtccagc gcgtgaccgt tactgacgcc agacgccgca    15420
cctgccccta cgtctacaag gccctgggca tagtcgcgcc gcgcgtcctc tcgagccgca    15480
ccttctaaat gtccattctc atctcgccca gtaataacac cggttgggc ctgcgcgcgc     15540 ccagcaagat gtacggaggc gctcgccaac gctccacgca acacccgtg cgcgtgcgcg     15600 ggcacttccg cgctccctgg ggcgccctca agggccgcgt gcggtcgcgc accaccgtcg    15660
acgacgtgat cgaccaggtg gtggccgacg cgcgcaacta cacccccgcc gccgcgcccg    15720
tctccaccgt ggacgccgtc atcgacagcg tggtggcgga cgcgcgccgg tacgcccgcg    15780
ccaagagccg gcggcggcgc atcgcccggc ggcaccggag caccccgcc atgcgcgcgg     15840 cgcgagcctt gctgcgcagg gccaggcgca cgggacgcag ggccatgctc agggcggcca    15900
gacgcgcggc ttcaggcgcc agcgccggca ggacccggag acgcgcggcc acggcggcgg    15960
cagcggccat cgccagcatg tcccgcccgc ggcgagggaa cgtgtactgg gtgcgcgacg    16020
ccgccaccgg tgtgcgcgtg cccgtgcgca cccgcccccc tcgcacttga agatgttcac    16080
ttcgcgatgt tgatgtgtcc cagcggcgag gaggatgtcc aagcgcaaat tcaaggaaga    16140
gatgctccag gtcatcgcgc ctgagatcta cggccctgcg gtggtgaagg aggaaagaaa    16200
gccccgcaaa atcaagcggg tcaaaaagga caaaaaggaa gaagaaagtg atgtggacgg    16260
attggtggag tttgtgcgcg agttcgcccc ccggcggcgc gtgcagtggc gcgggcggaa    16320
```

```
ggtgcaaccg gtgctgagac ccggcaccac cgtggtcttc acgcccggcg agcgctccgg    16380
caccgcttcc aagcgctcct acgacgaggt gtacggggat gatgatattc tggagcaggc    16440
ggccgagcgc ctgggcgagt ttgcttacgg caagcgcagc cgttccgcac cgaaggaaga    16500
ggcggtgtcc atcccgctgg accacggcaa ccccacgccg agcctcaagc ccgtgacctt    16560
gcagcaggtg ctgccgaccg cggcgccgcg ccggggggttc aagcgcgagg gcgaggatct    16620
gtaccccacc atgcagctga tggtgccaa gcgccagaag ctggaagacg tgctggagac    16680
catgaaggtg gacccggacg tgcagcccga ggtcaaggtg cggcccatca gcaggtggc    16740 cccgggcctg ggcgtgcaga ccgtggacat caagattccc acggagccca tggaaacgca    16800
gaccgagccc atgatcaagc ccagcaccag caccatggag gtgcagacgg atccctggat    16860
gccatcggct cctagtcgaa gaccccggcg caagtacggc gcggccagcc tgctgatgcc    16920
caactacgcg ctgcatcctt ccatcatccc cacgccgggc taccgcggca cgcgcttcta    16980
ccgcggtcat accagcagcc gccgccgcaa gaccaccact cgccgccgcc gtcgccgcac    17040
cgccgctgca accaccccctg ccgccctggt gcggagagtg taccgccgcg ccgcgcacc    17100 tctgaccctg ccgcgcgcgc gctaccaccc gagcatcgcc atttaaactt cgccagctt    17160 tgcagatcaa tggccctcac atgccgcctt cgcgttccca ttacgggcta ccgaggaaga    17220
aaaccgcgcc gtagaaggct ggcggggaac gggatgcgtc gccaccacca ccggcggcgg    17280
cgcgccatca gcaagcggtt gggggggaggc ttcctgcccg cgctgatccc catcatcgcc    17340
gcggcgatcg gggcgatccc cggcattgct tccgtggcgg tgcaggcctc tcagcgccac    17400
tgagacacac ttggaaacat cttgtaataa acccatggac tctgacgctc ctggtcctgt    17460
gatgtgtttt cgtagacaga tggaagacat caatttttcg tccctggctc cgcgacacgg    17520
cacgcggccg ttcatgggca cctggagcga catcggcacc agccaactga acggggcgc    17580 cttcaattgg agcagtctct ggagcgggct taagaatttc gggtccacgc ttaaaaccta    17640
tggcagcaag gcgtggaaca gcaccacagg gcaggcgctg agggataagc tgaaagagca    17700
gaacttccag cagaaggtgg tcgatggcct cgcctcgggc atcaacgggg tggtggacct    17760
ggccaaccag gccgtgcagc ggcagatcaa cagccgcctg gacccggtgc cgcccgccgg    17820
ctccgtggag atgccgcagg tggaggagga gctgcctccc ctggacaagc ggggcgagaa    17880 gcgacccccgc ccgatgcgg aggagacgct gctgacgcac acgacgagc cgccccgta    17940 cgaggaggcg gtgaaactgg gtctgcccac cacgcggccc atcgcgcccc tggccaccgg    18000
ggtgctgaaa cccgaaaagc ccgcgaccct ggacttgcct cctccccagc cttcccgccc    18060
ctctacagtg gctaagcccc tgccgccggt ggccgtggcc cgcgcgcgac ccggggggcac    18120 cgcccgccct catgcgaact ggcagagcac tctgaacagc atcgtgggtc tgggagtgca    18180
gagtgtgaag cgccgccgct gctattaaac ctaccgtagc gcttaacttg cttgtctgtg    18240
tgtgtatgta ttatgtcgcc gccgccgctg tccaccagaa ggaggagtga agaggcgcgt    18300
cgccgagttg caagatggcc accccatcga tgctgcccca gtgggcgtac atgcacatcg    18360
ccggacagga cgcttcggag tacctgagtc cgggtctggt gcagtttgcc cgcgccacag    18420
acacctactt cagtctgggg aacaagttta ggaaccccac ggtggcgccc acgcacgatg    18480
tgaccaccga ccgcagccag cggctgacgc tgcgcttcgt gcccgtggac cgcgaggaca    18540
acacctactc gtacaaagtg cgctacacgg tggccgtggg cgacaaccgc gtgctggaca    18600
tggccagcac ctactttgac atccgcggcg tgctggatcg gggccctagc ttcaaaccct    18660
```

```
actccggcac cgcctacaac agtctggccc ccaagggagc acccaacact tgtcagtgga   18720
catataaagc cgatggtgaa actgccacag aaaaaaccta tacatatgga aatgcacccg   18780
tgcagggcat taacatcaca aaagatggta ttcaacttgg aactgacacc gatgatcagc   18840
caatctacgc agataaaacc tatcagcctg aacctcaagt gggtgatgct gaatggcatg   18900
acatcactgg tactgatgaa agtatggag gcagagctct taagcctgat accaaaatga    18960
agccttgtta tggttctttt gccaagccta ctaataaaga aggaggtcag gcaaatgtga   19020
aaacaggaac aggcactact aaagaatatg acatagacat ggctttcttt gacaacagaa   19080
gtgcggctgc tgctggccta gctccagaaa ttgttttgta tactgaaaat gtggatttgg   19140
aaactccaga tacccatatt gtatacaaag caggcacaga tgacagcagc tcttctatta   19200
atttgggtca gcaagccatg cccaacagac ctaactacat tggtttcaga gacaacttta   19260
tcgggctcat gtactacaac agcactggca atatgggggt gctggccggt caggcttctc   19320
agctgaatgc tgtggttgac ttgcaagaca gaaacaccga gctgtcctac cagctcttgc   19380
ttgactctct gggtgacaga acccggtatt tcagtatgtg gaatcaggcg gtggacagct   19440
atgatcctga tgtgcgcatt attgaaaatc atggtgtgga ggatgaactt cccaactatt   19500
gtttccctct ggatgctgtt ggcagaacag atacttatca gggaattaag gctaatggaa   19560
ctgatcaaac cacatggacc aaagatgaca gtgtcaatga tgctaatgag ataggcaagg   19620
gtaatccatt cgccatggaa atcaacatcc aagccaacct gtggaggaac ttcctctacg   19680
ccaacgtggc cctgtacctg cccgactctt acaagtacac gccggccaat gttaccctgc   19740
ccaccaacac caacacctac gattacatga acggccgggt ggtggcgccc tcgctggtgg   19800
actcctacat caacatcggg gcgcgctggt cgctggatcc catggacaac gtgaacccct   19860
tcaaccacca ccgcaatgcg gggctgcgct accgctccat gctcctgggc aacgggcgct   19920
acgtgccctt ccacatccag gtgccccaga aattttttcgc catcaagagc ctcctgctcc   19980
tgcccgggtc ctacacctac gagtggaact tccgcaagga cgtcaacatg atcctgcaga   20040
gctccctcgg caacgacctg cgcacggacg gggcctccat ctccttcacc agcatcaacc   20100
tctacgccac cttcttcccc atggcgcaca caccggcctc cacgctcgag gccatgctgc   20160
gcaacgacac caacgaccag tccttcaacg actacctctc ggcggccaac atgctctacc   20220
ccatcccggc caacgccacc aacgtgccca tctccatccc ctcgcgcaac tgggccgcct   20280
tccgcggctg gtccttcacg cgtctcaaga ccaaggagac gccctcgctg ggctccgggt   20340 tcgacccctac cttcgtctac tcgggctcca tcccctacct cgacggcacc ttctacctca   20400 accacaccttt caagaaggtc tccatcacct tcgactcctc cgtcagctgg cccggcaacg   20460
accggctcct gacgcccaac gagttcgaaa tcaagcgcac cgtcgacggc gagggctaca   20520
acgtggccca gtgcaacatg accaaggact ggttcctggt ccagatgctg gcccactaca   20580
acatcggcta ccagggcttc tacgtgcccg agggctacaa ggaccgcatg tactccttct   20640
tccgcaactt ccagccatg agccgccagg tggtggacga ggtcaactac aaggactacc   20700
aggccgtcac cctggcctac cagcacaaca actcgggctt cgtcggctac ctcgcgccca   20760
ccatgcgcca gggccagccc taccccgcca actacccta cccgctcatc ggcaagagcg   20820
ccgtcaccag cgtcacccag aaaaagttcc tctgcgacag ggtcatgtgg cgcatcccct   20880
tctccagcaa cttcatgtcc atgggcgcgc tcaccgacct cggccagaac atgctctatg   20940
ccaactccgc ccacgcgcta gacatgaatt tcgaagtcga ccccatggat gagtccaccc   21000
ttctctatgt tgtgcttcgaa gtcttcgacg tcgtccgagt gcaccagccc caccgcggcg   21060
```

```
tcatcgaggc cgtctacctg cgcacccct tctcggccgg taacgccacc acctaagctc    21120
ttgcttcttg caagccatgg ccgcgggctc cggcgagcag gagctcaggg ccatcatccg    21180
cgacctgggc tgcgggccct acttcctggg caccttcgat aagcgcttcc cgggattcat    21240
ggccccgcac aagctggcct cgccatcgt caacacggcc ggccgcgaga ccgggggcga    21300
gcactggctg gccttcgcct ggaacccgcg ctcgaacacc tgctacctct tcgaccccttt    21360
cgggttctcg gacgagcgcc tcaagcagat ctaccagttc gagtacgagg gcctgctgcg    21420
ccgcagcgcc ctggccaccg aggaccgctg cgtcaccctg gaaaagtcca cccagaccgt    21480
gcagggtccg cgctcggccg cctgcgggct cttctgctgc atgttcctgc acgccttcgt    21540
gcactggccc gaccgcccca tggacaagaa ccccaccatg aacttgctga cggggggtgcc    21600
caacggcatg ctccagtcgc cccaggtgga acccacctg cgccgcaacc aggaggcgct    21660
ctaccgcttc ctcaactccc actccgccta cttttcgctcc caccgcgcgc gcatcgagaa    21720
ggccaccgcc ttcgaccgca tgaatcaaga catgtaaacc gtgtgtgtat gttaaatgtc    21780
tttaataaac agcactttca tgttacacat gcatctgaga tgattttattt agaaatcgaa    21840
agggttctgc cgggtctcgg catggcccgc gggcagggac acgttgcgga actggtactt    21900
ggccagccac ttgaactcgg ggatcagcag tttgggcagc ggggtgtcgg ggaaggagtc    21960
ggtccacagc ttccgcgtca gttgcagggc gcccagcagg tcgggcgcgg agatcttgaa    22020
atcgcagttg ggaccgcgt tctgcgcgcg ggagttgcgg tacacggggt tgcagcactg    22080
gaacaccatc agggccgggt gcttcacgct cgccagcacc gtcgcgtcgg tgatgctctc    22140
cacgtcgagg tcctcggcgt tggccatccc gaaggggtc atcttgcagg tctgccttcc    22200
catggtgggc acgcacccgg gcttgtggtt gcaatcgcag tgcaggggga tcagcatcat    22260
ctgggcctgg tcggcgttca tccccgggta catggccttc atgaaagcct ccaattgcct    22320
gaacgcctgc tgggccttgg ctccctcggt gaagaagacc ccgcaggact tgctagagaa    22380
ctggttggtg gcgcacccgg cgtcgtgcac gcagcagcgc gcgtcgttgt tggccagctg    22440
caccacgctg cgccccccagc ggttctgggt gatcttggcc cggtcgggt tctccttcag    22500
cgcgcgctgc ccgttctcgc tcgccacatc catctcgatc atgtgctcct tctggatcat    22560
ggtggtcccg tgcaggcacc gcagcttgcc ctcggcctcg gtgcacccgt gcagccacag    22620
cgcgcacccg gtgcactccc agttcttgtg ggcgatctgg gaatgcgcgt gcacgaagcc    22680
ctgcaggaag cggcccatca tggtggtcag ggtcttgttg ctagtgaagg tcagcggaat    22740
gccgcggtgc tcctcgttga tgtacaggtg gcagatgcgg cggtacacct cgccctgctc    22800
gggcatcagc tggaagttgg ctttcaggtc ggtctccacg cggtagcggt ccatcagcat    22860
agtcatgatt tccatacct tctcccaggc cgagacgatg gcaggctca tagggttctt    22920
caccatcatc ttagcgctag cagccgcggc caggggtcg ctctcgtcca gggtctcaaa    22980
gctccgcttg ccgtccttct cggtgatccg caccgggggg tagctgaagc ccacggccgc    23040
cagctcctcc tcggcctgtc tttcgtcctc gctgtcctgg ctgacgtcct gcaggaccac    23100
atgcttggtc ttgcgggtt tcttcttggg cggcagcggc ggcggagatg ttggagatgg    23160
cgagggggag cgcgagttct cgctcaccac tactatctct tcctcttctt ggtccgaggc    23220
cacgcggcgg taggtatgtc tcttcggggg cagaggcgga ggcgacgggc tctcgccgcc    23280
gcgacttggc ggatggctgg cagagcccct tccgcgttcg ggggtgcgct cccggcggcg    23340
ctctgactga cttcctccgc ggccggccat tgtgttctcc tagggaggaa caacaagcat    23400
```

```
ggagactcag ccatcgccaa cctcgccatc tgcccccacc gccgacgaga agcagcagca   23460
gcagaatgaa agcttaaccg ccccgccgcc cagccccgcc acctccgacg cggccgtccc   23520
agacatgcaa gagatggagg aatccatcga gattgacctg ggctatgtga cgcccgcgga   23580
gcacgaggag gagctggcag tgcgcttttc acaagaagag atacaccaag aacagccaga   23640
gcaggaagca gagaatgagc agagtcaggc tgggctcgag catgacggcg actacctcca   23700
cctgagcggg gggaggacg cgctcatcaa gcatctggcc cggcaggcca ccatcgtcaa   23760
ggatgcgctg ctcgaccgca ccgaggtgcc cctcagcgtg gaggagctca gccgcgccta   23820
cgagttgaac ctcttctcgc cgcgcgtgcc ccccaagcgc cagcccaatg cacctgcga   23880 gcccaacccg cgcctcaact tctacccggt cttcgcggtg cccgaggccc tggccaccta   23940
ccacatcttt ttcaagaacc aaaagatccc cgtctcctgc cgcgccaacc gcacccgcgc   24000
cgacgccctt ttcaacctgg gtcccggcgc ccgcctacct gatatcgcct ccttggaaga   24060
ggttcccaag atcttcgagg gtctgggcag cgacgagact cgggccgcga acgtctgca   24120 aggagaagga ggagagcatg agcaccacag cgccctggtc gagttggaag gcgacaacgc   24180
gcggctggcg gtgctcaaac gcacggtcga gctgacccat ttcgcctacc cggctctgaa   24240 cctgccccc aaagtcatga gcgcggtcat ggaccaggtg ctcatcaagc gcgcgtcgcc   24300
catctccgag gacgagggca tgcaagactc cgaggagggc aagcccgtgg tcagcgacga   24360
gcagctggcc cggtggctgg gtcctaatgc tagtccccag agtttggaag agcggcgcaa   24420
actcatgatg gccgtggtcc tggtgaccgt ggagctggag tgcctgcgcc gcttcttcgc   24480
cgacgcggag accctgcgca aggtcgagga gaacctgcac tacctcttca ggcacggggtt   24540 cgtgcgccag gcctgcaaga tctccaacgt ggagctgacc aacctggtct cctacatggg   24600
catcttgcac gagaaccgcc tggggcagaa cgtgctgcac accaccctgc gcggggaggc   24660
ccggcgcgac tacatccgcg actgcgtcta cctctacctc tgccacacct ggcagacggg   24720
catgggcgtg tggcagcagt gtctggagga gcagaacctg aaaagctct gcaagctcct   24780 gcagaagaac ctcaagggtc tgtggaccgg gttcgacgag cgcaccaccg cctcggacct   24840 ggccgaccc attttccccg agcgcctcag gctgacgctg cgcaacggcc tgcccgactt   24900
tatgagccaa agcatgttgc aaaactttcg ctctttcatc ctcgaacgct ccggaatcct   24960
gcccgccacc tgctccgcgc tgccctcgga cttcgtgccg ctgaccttcc gcagtgccc   25020 cccgccgctg tggagccact gctacctgct gcgcctggcc aactacctgg cctaccactc   25080
ggacgtgatc gaggacgtca gcggcgaggg cctgctcgag tgccactgcc gctgcaacct   25140
ctgcacgccg caccgctccc tggcctgcaa ccccagctg ctgagcgaga cccagatcat   25200
cggcaccttc gagttgcaag ggcccagcga aggcgagggt tcagccgcca aggggggtct   25260
gaaactcacc ccggggctgt ggacctcggc ctacttgcgc aagttcgtgc ccgaggacta   25320
ccatcccttc gagatcaggt tctacgagga ccaatcccat ccgccaagg ccgagctgtc   25380 ggcctgcgtc atcacccagg gggcgatcct ggcccaattg caagccatcc agaaatcccg   25440
ccaagaattc ttgctgaaaa agggccgcgg ggtctacctc gacccccaga ccggtgagga   25500
gctcaacccc ggcttccccc aggatgcccc gaggaaacaa gaagctgaaa gtggagctgc   25560
cgcccgtgga ggatttggag gaagactggg agaacagcag tcaggcagag gaggaggaga   25620
tggaggaaga ctgggacagc actcaggcag aggaggacag cctgcaagac agtctggagg   25680
aagacgagga ggaggcagag gaggaggtgg aagaagcagc cgccgccaga ccgtcgtcct   25740
cggcggggga gaaagcaagc agcacggata ccatctccgc tccgggtcgg ggtcccgctc   25800
```

```
gaccacacag tagatgggac gagaccggac gattcccgaa ccccaccacc cagaccggta   25860
agaaggagcg gcagggatac aagtcctggc ggggcacaa aaacgccatc gtctcctgct    25920
tgcaggcctg cggggcaac atctccttca cccggcgcta cctgctcttc caccgcgggg    25980
tgaactttcc ccgcaacatc ttgcattact accgtcacct ccacagcccc tactacttcc   26040
aagaagaggc agcagcagca gaaaaagacc agcagaaaac cagcagctag aaaatccaca   26100
gcggcggcag caggtggact gaggatcgcg gcgaacgagc cggcgcaaac ccgggagctg    26160
aggaaccgga tctttcccac cctctatgcc atcttccagc agagtcgggg gcaggagcag   26220
gaactgaaag tcaagaaccg ttctctgcgc tcgctcaccc gcagttgtct gtatcacaag   26280
agcgaagacc aacttcagcg cactctcgag gacgccgagg ctctcttcaa caagtactgc   26340
gcgctcactc ttaaagagta gcccgcgccc gcccagtcgc agaaaaaggc gggaattacg   26400
tcacctgtgc ccttcgccct agccgcctcc acccatcatc atgagcaaag agattcccac   26460
gccttacatg tggagctacc agccccagat gggcctggcc gccggtgccg cccaggacta   26520
ctccacccgc atgaattggc tcagcgccgg gcccgcgatg atctcacggg tgaatgacat   26580
ccgcgcccac cgaaaccaga tactcctaga acagtcagcg ctcaccgcca cgccccgcaa   26640
tcacctcaat ccgcgtaatt ggcccgccgc cctggtgtac caggaaattc cccagcccac   26700
gaccgtacta cttccgcgag acgcccaggc cgaagtccag ctgactaact caggtgtcca   26760
gctggcgggc ggcgccaccc tgtgtcgtca ccgccccgct cagggtataa agcggctggt   26820
gatccggggc agaggcacac agctcaacga cgaggtggtg agctcttcgc tgggtctgcg   26880
acctgacgga gtcttccaac tcgccggatc ggggagatct tccttcacgc ctcgtcaggc   26940
cgtcctgact ttggagagtt cgtcctcgca gccccgctcg ggtggcatcg gcactctcca   27000
gttcgtggag gagttcactc cctcggtcta cttcaacccc ttctccggct ccccggcca    27060 ctacccggac gagttcatcc cgaacttcga cgccatcagc gagtcggtgg acggctacga   27120
ttgaatgtcc catggtggcg cagctgacct agctcggctt cgacacctgg accactgccg   27180
ccgcttccgc tgcttcgctc gggatctcgc cgagtttgcc tactttgagc tgcccgagga   27240
gcaccctcag ggcccggccc acggagtgcg gatcgtcgtc gaaggggggcc tcgactccca   27300 cctgcttcgg atcttcagcc agcgtccgat cctggtcgag cgcgagcaag gacagaccct   27360
tctgactctg tactgcatct gcaaccaccc cggcctgcat gaaagtcttt gttgtctgct   27420
gtgtactgag tataataaaa gctgagatca gcgactactc cggacttccg tgtgttcctg   27480
aatccatcaa ccagtctttg ttcttcaccg ggaacgagac cgagctccag ctccagtgta   27540
agccccacaa gaagtacctc acctggctgt tccagggctc cccgatcgcc gttgtcaacc   27600
actgcgacaa cgacggagtc ctgctgagcg ccctgccaa ccttactttt tccacccgca    27660
gaagcaagct ccagctcttc caacccttcc tccccgggac ctatcagtgc gtctcgggac   27720
cctgccatca caccttccac ctgatcccga ataccacagc gtcgctcccc gctactaaca   27780
accaaactaa cctccaccaa cgccaccgtc gcgaccttc tgaatctaat actaccaccc    27840
acaccggagg tgagctccga ggtcaaccaa cctctgggat ttactacggc ccctgggagg   27900
tggttgggtt aatagcgcta ggcctagttg cgggtgggct tttggttctc tgctaccat    27960 acctcccttg ctgttcgtac ttagtggtgc tgtgttgctg gtttaagaaa tggggaagat   28020 cacccctagtg agctgcggtg cgctggtggc ggtgttgctt cgattgtggg gactgggcgg   28080
tgcggctgta gtgaaggaga aggccgatcc ctgcttgcat ttcaatccca acaaatgcca   28140
```

```
gctgagtttt cagcccgatg gcaatcggtg cgcggtactg atcaagtgcg gatgggaatg    28200
cgagaacgtg agaatcgagt acaataacaa gactcggaac aatactctcg cgtccgtgtg    28260
gcagcccggg gaccccgagt ggtacaccgt ctctgtcccc ggtgctgacg gctccccgcg    28320
caccgtgaat aatactttca ttttttgcgca catgtgcgac acggtcatgt ggatgagcaa    28380
gcagtacgat atgtggcccc ccacgaagga gaacatcgtg gtcttctcca tcgcttacag    28440
cctgtgcacg cgctaatca ccgctatcgt gtgcctgagc attcacatgc tcatcgctat    28500
tcgcccaga aataatgccg aaaaagaaaa acagccataa cgttttttt cacacctttt      28560
tcagaccatg gcctctgtta aattttgct tttatttgcc agtctcattg ccgtcattca     28620
tggaatgagt aatgagaaaa ttactattta cactggcact aatcacacat tgaaaggtcc    28680
agaaaaagcc acagaagttt catggtattg ttattttaat gaatcagatg tatctactga    28740
actctgtgga aacaataaca aaaaaaatga gagcattact ctcatcaagt ttcaatgtgg    28800
atctgactta accctaatta acatcactag agactatgta ggtatgtatt atggaactac    28860
agcaggcatt tcggacatgg aattttatca agtttctgtg tctgaaccca ccacgcctag    28920
aatgaccaca accacaaaaa ctacacctgt taccactatg cagctcacta ccaataacat    28980
ttttgccatg cgtcaaatgg tcaacaatag cactcaaccc accccaccca gtgaggaaat    29040
tcccaaatcc atgattggca ttattgttgc tgtagtggtg tgcatgttga tcatcgcctt    29100
gtgcatggtg tactatgcct tctgctacag aaagcacaga ctgaacgaca agctggaaca    29160
cttactaagt gttgaatttt aatttttag aaccatgaag atcctaggcc ttttaatttt     29220
ttctatcatt acctctgctc tatgcaattc tgacaatgag gacgttactg tcgttgtcgg    29280
atcaaattat acactgaaag gtccagcgaa gggtatgctt tcgtggtatt gctattttgg    29340
atctgacact acagaaactg aattatgcaa tcttaagaat ggcaaaattc aaaattctaa    29400
aattaacaat tatatatgca atggtactga tctgatactc tcaatatca cgaaatcata    29460
tgctggcagt tacacctgcc ctggagatga tgctgacagt atgatttttt acaaagtaac    29520
tgttgttgat cccactactc cacctccacc caccacaact actcacacca cacacacaga    29580
tcaaaccgca gcagaggagg cagcaaagtt agccttgcag gtccaagaca gttcatttgt    29640
tggcattacc cctacacctg atcagcggtg tccggggctg ctagtcagcg gcattgtcgg    29700
tgtgctttcg ggattagcag tcataatcat ctgcatgttc atttttgctt gctgctatag    29760
aaggctttac cgacaaaaat cagacccact gctgaacctc tatgtttaat ttttttccaga   29820
gtcatgaagg cagttagcgc tctagttttt tgttctttga ttggcattgt ttttttgcaat   29880
cctattccta aagttagctt tattaaagat gtgaatgtta ctgaggggg caatgtgaca     29940
ctggtaggtg tagagggtgc tgaaaacacc acctggacaa ataccaccct caatgggtgg    30000
aaagatattt gcaattggag tgtattagtt tatacatgtg agggagttaa tcttaccatt    30060
gtcaatgcca cctcagctca aatggtaga attcaaggac aaagtgtcag tgtatctaat     30120
gggtatttta cccaacatac ttttatctat gacgttaaag tcataccact gcctacgcct    30180
agcccaccta gcactaccac acagacaacc cacactacac agacaaccac atacagtaca    30240
ttaaatcagc ctaccaccac tacagcagca gaggttgcca gctcgtctgg ggtccgagtg    30300
gcatttttga tgtgggcccc atctagcagt cccactgcta gtaccaatga gcagactact    30360
gaatttttgt ccactgtcga gagccacacc acagctacct ccagtgcctt ctctagcacc    30420
gccaatctct cctcgctttc ctctacacca atcagtcccg ctactactcc tagccccgct    30480
cctcttccca ctcccctgaa gcaaacagac ggcggcatgc aatggcagat caccctgctc    30540
```

```
attgtgatcg ggttggtcat cctggccgtg ttgctctact acatcttctg ccgccgcatt    30600
cccaacgcgc accgcaagcc ggtctacaag cccatcattg tcgggcagcc ggagccgctt    30660
caggtggaag ggggtctaag gaatcttctc ttctctttta cagtatggtg attgaactat    30720
gattcctaga caattcttga tcactattct tatctgcctc ctccaagtct gtgccaccct    30780
cgctctggtg gccaacgcca gtccagactg tattgggccc ttcgcctcct acgtgctctt    30840
tgccttcacc acctgcatct gctgctgtag catagtctgc ctgcttatca ccttcttcca    30900
gttcattgac tggatctttg tgcgcatcgc ctacctgcgc caccaccccc agtaccgcga    30960
ccagcgagtg gcgcggctgc tcaggctcct ctgataagca tgcgggctct gctacttctc    31020
gcgcttctgc tgttagtgct cccccgtccc gtcgaccccc ggtcccccac ccagtccccc    31080
gaggaggtcc gcaaatgcaa attccaagaa ccctggaaat tcctcaaatg ctaccgccaa    31140
aaatcagaca tgcatcccag ctggatcatg atcattggga tcgtgaacat tctggcctgc    31200
accctcatct cctttgtgat ttaccccctgc tttgactttg gttggaactc gccagaggcg    31260
ctctatctcc cgcctgaacc tgacacacca ccacagcaac ctcaggcaca cgcactacca    31320
ccactacagc ctaggccaca atacatgccc atattagact atgaggccga gccacagcga    31380
cccatgctcc ccgctattag ttacttcaat ctaaccggcg gagatgactg acccactggc    31440
caacaacaac gtcaacgacc ttctcctgga catggacggc cgcgcctcgg agcagcgact    31500
cgcccaactt cgcattcgcc agcagcagga gagagccgtc aaggagctgc aggatgcggt    31560
ggccatccac cagtgcaaga gaggcatctt ctgcctggtg aaacaggcca agatctccta    31620
cgaggtcact ccaaacgacc atcgcctctc ctacgagctc ctgcagcagc gccagaagtt    31680
cacctgcctg gtcggagtca cccccatcgt catcacccag cagtctggcg ataccaaggg    31740
gtgcatccac tgctcctgcg actccccccga ctgcgtccac actctgatca agaccctctg    31800
cggcctccgc gacctcctcc ccatgaacta atcacccccct tatccagtga ataaagatc    31860 atattgatga tgatttaca gaaataaaaa ataatcattt gatttgaaat aaagatacaa    31920
tcatattgat gatttgagtt taacaaaaaa ataaagaatc acttacttga aatctgatac    31980
caggtctctg tccatgtttt ctgccaacac cacttcactc ccctcttccc agctctggta    32040
ctgcaggccc cggcgggctg caaacttcct ccacacgctg aaggggatgt caaattcctc    32100
ctgtccctca atcttcattt tatcttctat cagatgtcca aaaagcgcgt ccgggtggat    32160
gatgacttcg accccgtcta cccctacgat gcagacaacg caccgaccgt gcccttcatc    32220
aaccccccct tcgtctcttc agatggattc caagagaagc cctgggggt gttgtccctg    32280 cgactggccg accccgtcac caccaagaac ggggaaatca ccctcaagct gggagagggg    32340
gtggacctcg attcctcggg aaaactcatc tccaacacgg ccaccaaggc cgccgccct     32400 ctcagttttt ccaacaacac catttccctt aacatggatc accccttta cactaaagat     32460 ggaaaattat ccttacaagt ttctccacca ttaaatatac tgagaacaag cattctaaac    32520
acactagctt taggttttgg atcaggttta ggactccgtg gctctgcctt ggcagtacag    32580
ttagtctctc cacttacatt tgatactgat ggaaacataa agcttacctt agacagaggt    32640
ttgcatgtta caacaggaga tgcaattgaa agcaacataa gctgggctaa aggtttaaaa    32700
tttgaagatg gagccatagc aaccaacatt ggaaatgggt tagagtttgg aagcagtagt    32760
acagaaacag gtgttgatga tgcttaccca atccaagtta aacttggatc tggccttagc    32820
tttgacagta caggagccat aatggctggt aacaaagaag acgataaact cactttgtgg    32880
```

```
acaacacctg atccatcacc aaactgtcaa atactcgcag aaaatgatgc aaaactaaca  32940
ctttgcttga ctaaatgtgg tagtcaaata ctggccactg tgtcagtctt agttgtagga  33000
agtggaaacc taaaccccat tactggcacc gtaagcagtg ctcaggtgtt tctacgtttt  33060
gatgcaaacg tgttctttt aacagaacat tctacactaa aaaatactg ggggtatagg  33120
cagggagata gcatagatgg cactccatat accaatgctg taggattcat gcccaattta  33180
aaagcttatc caaagtcaca aagttctact actaaaaata atatagtagg gcaagtatac  33240
atgaatggag atgtttcaaa acctatgctt ctcactataa ccctcaatgg tactgatgac  33300
agcaacagta catattcaat gtcattttca tacacctgga ctaatggaag ctatgttgga  33360
gcaacatttg gggctaactc ttataccttc tcatacatcg cccaagaatg aacactgtat  33420
cccaccctgc atgccaaccc ttcccacccc actctgtgga acaaactctg aaacacaaaa  33480
taaaataaag ttcaagtgtt ttattgattc aacagtttta caggattcga gcagttattt  33540
ttcctccacc ctcccaggac atggaataca ccaccctctc cccccgcaca gccttgaaca  33600
tctgaatgcc attggtgatg acatgctttt tggtctccac gttccacaca gtttcagagc  33660
gagccagtct cgggtcggtc agggagatga aaccctccgg gcactcccgc atctgcacct  33720
cacagctcaa cagctgagga ttgtcctcgg tggtcgggat cacggttatc tggaagaagc  33780
agaagagcgg cggtgggaat catagtccgc gaacgggatc ggccggtggt gtcgcatcag  33840
gccccgcagc agtcgctgcc gccgccgctc cgtcaagctg ctgctcaggg ggtccgggtc  33900
cagggactcc ctcagcatga tgcccacggc cctcagcatc agtcgtctgg tgcggcgggc  33960
gcagcagcgc atgcggatct cgctcaggtc gctgcagtac gtgcaacaca gaaccaccag  34020
gttgttcaac agtccatagt tcaacacgct ccagccgaaa ctcatcgcgg gaaggatgct  34080
acccacgtgg ccgtcgtacc agatcctcag gtaaatcaag tggtgccccc tccagaacac  34140
gctgcccacg tacatgatct ccttgggcat gtggcggttc accacctccc ggtaccacat  34200
caccctctgt tgaacatgc agccccggat gatcctgcgg aaccacaggg ccagcaccgc  34260
cccgcccgcc atgcagcgaa gagacccccgg gtcccggcaa tggcaatgga ggacccaccg  34320
ctcgtacccg tggatcatct gggagctgaa caagtctatg ttggcacagc acaggcatat  34380
gctcatgcat ctcttcagca ctctcaactc ctcggggggtc aaaaccatat cccagggcac  34440
ggggaactct tgcaggacag cgaacccccgc agaacagggc aatcctcgca cagaacttac  34500
attgtgcatg gacagggtat cgcaatcagg cagcaccggg tgatcctcca ccagagaagc  34560
gcgggtctcg gtctcctcac agcgtggtaa ggggggccggc cgatacgggt gatgcggga  34620
cgcggctgat cgtgttcgcg accgtgtcat gatgcagttg ctttcggaca ttttcgtact  34680
tgctgtagca gaacctggtc cgggcgctgc acaccgatcg ccggcggcgg tctcggcgct  34740
tggaacgctc ggtgttgaaa ttgtaaaaca gccactctct cagaccgtgc agcagatcta  34800
gggcctcagg agtgatgaag atcccatcat gcctgatggc tctgatcaca tcgaccaccg  34860
tggaatgggc cagacccagc cagatgatgc aattttgttg ggtttcggtg acggcggggg  34920
agggaagaac aggaagaacc atgattaact tttaatccaa acggtctcgg agtacttcaa  34980
aatgaagatc gcggagatgg cacctctcgc ccccgctgtg ttggtggaaa ataacagcca  35040
ggtcaaaggt gatacggttc tcgagatgtt ccacggtggc ttccagcaaa gcctccacgc  35100
gcacatccag aaacaagaca atagcgaaag cgggagggtt ctctaattcc tcaatcatca  35160
tgttacactc ctgcaccatc cccagataat tttcattttt ccagccttga atgattcgaa  35220
ctagttcgtg aggtaaatcc aagccagcca tgataaagag ctcgcgcaga gcgccctcca  35280
```

```
ccggcattct taagcacacc ctcataattc caagatattc tgctcctggt tcacctgcag    35340
cagattgaca agcggaatat caaaatctct gccgcgatcc ctgagctcct ccctcagcaa    35400
taactgtaag tactctttca tatcctctcc gaaatttta gccataggac caccaggaat     35460
aagattaggg caagccacag tacagataaa ccgaagtcct ccccagtgag cattgccaaa    35520
tgcaagactg ctataagcat gctggctaga cccggtgata tcttccagat aactggacag    35580
aaaatcgccc aggcaatttt taagaaaatc aacaaaagaa aaatcctcca ggtggacgtt    35640
tagagcctcg ggaacaacga tgaagtaaat gcaagcggtg cgttccagca tggttagtta    35700
gctgatctgt agaaaaaaca aaaatgaaca ttaaaccatg ctagcctggc gaacaggtgg    35760
gtaaatcgtt ctctccagca ccaggcaggc cacggggtct ccggcgcgac cctcgtaaaa    35820
attgtcgcta tgattgaaaa ccatcacaga gagacgttcc cggtggccgg cgtgaatgat    35880
tcgacaagat gaatacaccc ccggaacatt ggcgtccgcg agtgaaaaaa agcgcccgag    35940
gaagcaataa ggcactacaa tgctcagtct caagtccagc aaagcgatgc catgcggatg    36000
aagcacaaaa ttctcaggtg cgtacaaaat gtaattactc ccctcctgca caggcagcaa    36060
agcccccgat ccctccaggt acacatacaa agcctcagcg tccatagctt accgagcagc    36120
agcacacaac aggcgcaaga gtcagagaaa ggctgagctc taacctgtcc acccgctctc    36180
tgctcaatat atagcccaga tctacactga cgtaaaggcc aaagtctaaa atacccgcc     36240 aaataatcac acacgcccag cacacgccca gaaaccggtg acacactcaa aaaaatacgc    36300
gcacttcctc aaacgcccaa aactgccgtc atttccgggt tcccacgcta cgtcatcaaa    36360
acacgacttt caaattccgt cgaccgttaa aaacgtcacc cgccccgccc ctaacggtcg    36420
cccgtctctc agccaatcag cgccccgcat ccccaaattc aaacacctca tttgcatatt    36480
aacgcgcaca aaaagtttga ggtatattat tgatgatgg                           36519

<210> SEQ ID NO 2
<211> LENGTH: 2588
<212> TYPE: DNA
<213> ORGANISM: Chimpanzee adenovirus C68

<400> SEQUENCE: 2
ttacaggatt cgagcagtta ttttcctcc accctcccag gacatggaat acaccaccct      60
ctccccccgc acagccttga acatctgaat gccattggtg atggacatgc ttttggtctc    120
cacgttccac acagtttcag agcgagccag tctcgggtcg gtcagggaga tgaaaccctc    180
cgggcactcc cgcatctgca cctcacagct caacagctga ggattgtcct cggtggtcgg    240
gatcacggtt atctggaaga agcagaagag cggcggtggg aatcatagtc gcgaacggg     300 atcggccggt ggtgtcgcat caggccccgc agcagtcgct gccgccgccg ctccgtcaag    360
ctgctgctca gggggtccgg gtccagggac tccctcagca tgatgcccac ggccctcagc    420
atcagtcgtc tggtgcggcg ggcgcagcag cgcatgcgga tctcgctcag gtcgctgcag    480
tacgtgcaac acagaaccac caggttgttc aacagtccat agttcaacac gctccagccg    540
aaactcatcg cggaaggat gctacccacg tggccgtcgt accagatcct caggtaaatc      600
aagtggtgcc cctccagaa cacgctgccc acgtacatga tctccttggg catgtggcgg      660
ttcaccacct cccggtacca catcaccctc tggttgaaca tgcagccccg gatgatcctg    720
cggaaccaca gggccagcac cgccccgccc gccatgcagc gaagagaccc cgggtcccgg    780
caatggcaat ggaggaccca ccgctcgtac ccgtggatca tctgggagct gaacaagtct    840
```

```
atgttggcac agcacaggca tatgctcatg catctcttca gcactctcaa ctcctcgggg    900
gtcaaaacca tatcccaggg cacggggaac tcttgcagga cagcgaaccc cgcagaacag    960
ggcaatcctc gcacagaact acattgtgc atggacaggg tatcgcaatc aggcagcacc    1020
gggtgatcct ccaccagaga agcgcgggtc tcggtctcct cacagcgtgg taagggggcc    1080
ggccgatacg ggtgatggcg ggacgcggct gatcgtgttc gcgaccgtgt catgatgcag    1140
ttgctttcgg acattttcgt acttgctgta gcagaacctg gtccgggcgc tgcacaccga    1200
tcgccggcgg cggtctcggc gcttggaacg ctcggtgttg aaattgtaaa acagccactc    1260
tctcagaccg tgcagcagat ctagggcctc aggagtgatg aagatcccat catgcctgat    1320
ggctctgatc acatcgacca ccgtggaatg ggccagaccc agccagatga tgcaattttg    1380
ttgggtttcg gtgacggcgg gggagggaag aacaggaaga accatgatta acttttaatc    1440
caaacggtct cggagtactt caaaatgaag atcgcggaga tggcacctct cgccccgct    1500
gtgttggtgg aaaataacag ccaggtcaaa ggtgatacgg ttctcgagat gttccacggt    1560
ggcttccagc aaagcctcca cgcgcacatc cagaaacaag acaatagcga aagcgggagg    1620
gttctctaat tcctcaatca tcatgttaca ctcctgcacc atccccagat aattttcatt    1680
tttccagcct tgaatgattc gaactagttc gtgaggtaaa tccaagccag ccatgataaa    1740
gagctcgcgc agagcgccct ccaccggcat tcttaagcac accctcataa ttccaagata    1800
ttctgctcct ggttcacctg cagcagattg acaagcggaa tatcaaaatc tctgccgcga    1860
tccctgagct cctccctcag caataactgt aagtactctt tcatatcctc tccgaaattt    1920
ttagccatag gaccaccagg aataagatta gggcaagcca cagtacagat aaaccgaagt    1980
cctccccagt gagcattgcc aaatgcaaga ctgctataag catgctggct agacccggtg    2040
atatcttcca gataactgga cagaaaatcg cccaggcaat ttttaagaaa atcaacaaaa    2100
gaaaaatcct ccaggtggac gtttagagcc tcgggaacaa cgatgaagta aatgcaagcg    2160
gtgcgttcca gcatggttag ttagctgatc tgtagaaaaa acaaaaatga acattaaacc    2220
atgctagcct ggcgaacagg tgggtaaatc gttctctcca gcaccaggca ggccacgggg    2280
tctccggcgc gaccctcgta aaaattgtcg ctatgattga aaaccatcac agagagacgt    2340
tcccggtggc cggcgtgaat gattcgacaa gatgaataca ccccggaac attggcgtcc    2400
gcgagtgaaa aaaagcgccc gaggaagcaa taaggcacta caatgctcag tctcaagtcc    2460
agcaaagcga tgccatgcgg atgaagcaca aaattctcag gtgcgtacaa aatgtaatta    2520
ctcccctcct gcacaggcag caaagccccc gatccctcca ggtacacata caaagcctca    2580
gcgtccat                                                            2588
```

<210> SEQ ID NO 3
<211> LENGTH: 124
<212> TYPE: PRT
<213> ORGANISM: Chimpanzee adenovirus Y25

<400> SEQUENCE: 3

Met Asp Ala Glu Ala Leu Tyr Val Phe Leu Glu Gly Ala Gly Ala Leu
1               5                   10                  15

Leu Pro Val Gln Glu Gly Ser Asn Tyr Ile Phe Tyr Ala Pro Ala Asn
            20                  25                  30

Phe Val Leu His Pro His Gly Val Ala Leu Leu Glu Leu Arg Leu Ser
        35                  40                  45

Ile Val Val Pro Arg Gly Phe Ile Gly Arg Phe Phe Ser Leu Thr Asp
    50                  55                  60

```
Ala Asn Val Pro Gly Val Tyr Ala Ser Ser Arg Ile Ile His Ala Gly
 65                  70                  75                  80

His Arg Glu Gly Leu Ser Val Met Leu Phe Asn His Gly Asp Ser Phe
                 85                  90                  95

Tyr Glu Gly Arg Ala Gly Asp Pro Val Ala Cys Leu Val Leu Glu Arg
                100                 105                 110

Val Ile Tyr Pro Pro Val Arg Gln Ala Ser Met Val
            115                 120
```

<210> SEQ ID NO 4
<211> LENGTH: 129
<212> TYPE: PRT
<213> ORGANISM: Chimpanzee adenovirus Y25

<400> SEQUENCE: 4

```
Met Leu Glu Arg Thr Pro Cys Thr Tyr Ser Ile Val Val Pro Glu Ala
 1               5                  10                  15

Leu Asn Leu His Leu Asp Asp Phe Ser Phe Val Asp Phe Leu Lys Asn
                 20                  25                  30

Cys Leu Pro Asp Phe Leu Ser Ser Tyr Leu Glu Asp Ile Thr Gly Ser
                 35                  40                  45

Ser Gln His Ala Tyr Phe Asn Leu Thr Phe Gly Asn Ala His Trp Gly
 50                  55                  60

Gly Leu Arg Phe Ile Cys Asn Val Ala Cys Pro Ala Leu Ile Pro Gly
 65                  70                  75                  80

Gly Pro Met Ala Lys Asn Phe Gly Asp Asp Met Lys Asp Tyr Ile Gln
                 85                  90                  95

Leu Leu Leu Arg Glu Glu Leu Arg Asp Arg Gly Arg Asp Phe Asp Ile
                100                 105                 110

Pro Ile Val Asn Leu Leu Gln Val Asn Gln Glu Gln Asn Leu Leu Glu
                115                 120                 125

Leu
```

<210> SEQ ID NO 5
<211> LENGTH: 117
<212> TYPE: PRT
<213> ORGANISM: Chimpanzee adenovirus Y25

<400> SEQUENCE: 5

```
Met Arg Val Cys Leu Arg Met Pro Val Glu Gly Ala Leu Arg Glu Leu
 1               5                  10                  15

Phe Ile Met Ala Gly Leu Asp Leu Pro Gln Glu Leu Ile Arg Ile Ile
                 20                  25                  30

Gln Gly Trp Lys Asn Glu Asn Tyr Leu Gly Met Val Gln Glu Cys Asn
                 35                  40                  45

Met Met Ile Glu Glu Leu Glu Asn Ala Pro Ala Phe Ala Val Leu Leu
 50                  55                  60

Phe Leu Asp Val Arg Val Ala Leu Leu Glu Ala Thr Val Glu His
 65                  70                  75                  80

Leu Glu Asn Arg Val Thr Phe Asp Leu Ala Val Ile Phe His Gln His
                 85                  90                  95

Ser Gly Gly Glu Arg Cys His Leu Arg Asp Leu His Phe Glu Val Leu
                100                 105                 110

Arg Asp Arg Leu Glu
            115
```

<210> SEQ ID NO 6
<211> LENGTH: 36711
<212> TYPE: DNA
<213> ORGANISM: Chimpanzee adenovirus AdY25

<400> SEQUENCE: 6

| | | | | | | |
|---|---|---|---|---|---|---|
| ccatcatcaa | taatatacct | caaacttttt | gtgcgcgtta | atatgcaaat | gaggcgtttg | 60 |
| aatttgggaa | gggaggaagg | tgattggccg | agagaagggc | gaccgttagg | ggcggggcga | 120 |
| gtgacgtttt | gatgacgtga | ccgcgaggag | gagccagttt | gcaagttctc | gtgggaaaag | 180 |
| tgacgtcaaa | cgaggtgtgg | tttgaacacg | gaaatactca | attttcccgc | gctctctgac | 240 |
| aggaaatgag | gtgtttctag | gcggatgcaa | gtgaaaacgg | gccattttcg | cgcgaaaact | 300 |
| gaatgaggaa | gtgaaaatct | gagtaatttc | gcgtttatga | cagggaggag | tatttgccga | 360 |
| gggccgagta | gactttgacc | gattacgtgg | gggtttcgat | taccgtgttt | ttcacctaaa | 420 |
| tttccgcgta | cggtgtcaaa | gtccggtgtt | tttacgtagg | tgtcagctga | tcgccagggt | 480 |
| atttaaacct | gcgctctcca | gtcaagaggc | cactcttgag | tgccagcgag | aagagttttc | 540 |
| tcctccgcgc | cgcgagtcag | atctacactt | tgaaagatga | ggcacctgag | agacctgccc | 600 |
| gatgagaaaa | tcatcatcgc | ttccgggaac | gagattctgg | aactggtggt | aaatgccatg | 660 |
| atgggcgacg | accctccgga | gccccccacc | ccatttgagg | caccttcgct | acacgatttg | 720 |
| tatgatctgg | aggtggatgt | gcccgaggac | gaccccaacg | aggaggcggt | aaatgattta | 780 |
| tttagcgatg | ccgcgctgct | agctgccgag | gaggcttcga | gccctagctc | agacagcgac | 840 |
| tcttcactgc | ataccoctag | acccggcaga | ggtgagaaaa | agatccccga | gcttaaaggg | 900 |
| gaagagatgg | acttgcgctg | ctatgaggaa | tgcttgcccc | cgagcgatga | tgaggacgag | 960 |
| caggcgatcc | agaacgcagc | gagccaggga | atgcaagccg | ccagcgagag | ttttgcgctg | 1020 |
| gactgcccgc | ctctgccggg | acacggctgt | aagtcttgtg | aatttcatcg | cttgaatact | 1080 |
| ggagataaag | ctgtgttatg | tgcactttgc | tatatgagag | cttacaacca | ttgtgtttac | 1140 |
| agtaagtgtg | attaagttga | actttagagg | gaggcagaga | gcagggtgac | tgggcgatga | 1200 |
| ctggtttatt | tatgtatata | tgttcttatt | ataggtcccg | tctctgacgc | agatgatgag | 1260 |
| accccccacta | cagagtccac | ttcgtcaccc | ccagaaattg | gcacatctcc | acctgagaat | 1320 |
| attgttagac | cagttcctgt | tagagccact | gggaggagag | cagctgtgga | atgtttggat | 1380 |
| gacttgctac | aggctgggga | tgaaccttgg | gacttgtgta | cccggaaacg | ccccaggcac | 1440 |
| taagtgccac | acatgtgtgt | ttacttgagg | tgatgtcagt | atttataggg | tgtggagtgc | 1500 |
| aataaaaaat | gtgttgactt | taagtgcgtg | gtttatgact | caggggtggg | gactgtgggt | 1560 |
| atataagcag | gtgcagacct | gtgtggttag | ctcagagcgg | catggagatt | tggacgatct | 1620 |
| tggaagatct | tcacaagact | agacagctgc | tagagaacgc | ctcgaacgga | gtctctcacc | 1680 |
| tgtggagatt | ctgcttcggt | ggcgacctag | ctaagctagt | ctatagggcc | aaacaggatt | 1740 |
| atagcgaaca | atttgaggtt | attttgagag | agtgtccggg | tcttttttgac | gctcttaatt | 1800 |
| tgggtcatca | gactcacttt | aaccagagga | ttgtaagagc | ccttgatttt | actactcccg | 1860 |
| gcagatccac | tgcggcagta | gccttttttg | cttttcttct | tgacaaatgg | agtcaagaaa | 1920 |
| cccatttcag | cagggattac | cagctggatt | tcttagcagt | agctttgtgg | agaacatgga | 1980 |
| aatcccagcg | cctgaatgca | atctcaggct | acttgccggt | acagccacta | gacactctga | 2040 |
| agatcctgaa | tctccaggag | agtcccaggg | cacgccaacg | tcgccggcag | cagcagcggc | 2100 |
| agcaggagga | ggatcaagaa | gagaacccga | gagccggcct | ggaccctccg | gcggaggagg | 2160 |

```
agtagctgac ctgtttcctg aactgcgccg ggtgctgact aggtcttcga gtggtcggga    2220
gagggggatt aagcgggaga ggcatgatga gactaatcac agaactgaac tgactgtggg    2280
tctgatgagc cgcaagcgtc cagaaacagt gtggtggcat gaggtgcagt cgactggcac    2340
agatgaggtg tcagtgatgc atgagaggtt ttccctagaa caagtcaaga cttgttggtt    2400
agagcctgag gatgattggg aggtagccat caggaattat gccaagctgg ctctgaggcc    2460
agacaagaag tacaagatta ctaagctgat aaatatcaga aatgcctgct acatctcagg    2520
gaatggggct gaagtggaga tctgtcttca ggaaagggtg gctttcagat gctgcatgat    2580
gaatatgtac ccgggagtgg tgggcatgga tgggtcacc tttatgaaca tgaggttcag     2640
gggagatggg tataatggca cggtctttat ggccaatacc aagctgacag ttcatggctg    2700
ctccttcttt gggtttaata cacctgcat gaggcctgg ggtcaggttg gtgtgagggg      2760
ctgtagtttt tcagccaact ggatgggggt cgtgggcagg accaagagta tgctgtccgt    2820
gaagaaatgc ttgttcgaga ggtgccacct ggggtgatg agcgagggcg aagccagaat     2880
ccgccactgc gcctctaccg agacgggctg ttttgtgctg tgcaagggca atgctaagat    2940
caagcataat atgatctgtg gagcctcgga cgagcgcggc taccagatgc tgacctgcgc    3000
cggtgggaac agccatatgc tggccaccgt gcatgtggcc tcccatgccc gcaagccctg    3060
gcccgagttc gagcacaatg tcatgaccag gtgcaatatg catctggggt cccgccgagg    3120
catgttcatg ccctatcagt gcaacctgaa ttatgtgaag gtgctgctgg agcccgatgc    3180
catgtccaga gtgagcctga cggggtgtt tgacatgaat gtggaggtgt ggaagattct     3240
gagatatgat gaatccaaga ccaggtgccg agcctgcgag tgcggaggga agcatgccag    3300
gttccagccc gtgtgtgtgg aggtgacgga ggacctgcga cccgatcatt tggtgttgtc    3360
ctgcaccggg acggagttcg gttccagcgg ggaagaatct gactagagtg agtagtgttc    3420
tggggcgggg gaggacctgc atgagggcca gaatgactga atctgtgct tttctgtgtg     3480 ttgcagcatc atgagcggaa gcggctcctt tgagggaggg gtattcagcc cttatctgac    3540
ggggcgtctc ccctcctggg cgggagtgcg tcagaatgtg atgggatcca cggtggacgg    3600
ccggcccgtg cagcccgcga actcttcaac cctgacctat gcaaccctga gctcttcgtc    3660
ggtggacgca gctgccgccg cagctgctgc atccgccgcc agcgccgtgc gcggaatggc    3720
catgggcgcc ggctactacg gcactctggt ggccaactcg agttccacca ataatcccgc    3780
cagcctgaac gaggagaagc tgctgctgct gatggcccag cttgaggcct tgacccagcg    3840
cctgggcgag ctgacccagc aggtggctca gctgcaggag cagacgcggg ccgcggttgc    3900
cacggtgaaa tccaaataaa aaatgaatca ataaataaac ggagacggtt gttgattta    3960 acacagagtc tgaatcttta tttgattttt cgcgcgcgt aggccctgga ccaccggtct     4020
cgatcattga gcacccggtg gatcttttcc aggacccggt agaggtgggc ttggatgttg    4080
aggtacatgg gcatgagccc gtcccgggggt ggaggtagc tccattgcag ggcctcgtgc    4140
tcgggggtgg tgttgtaaat cacccagtca tagcaggggc gcagggcgtg gtgttgcaca    4200
atatctttga ggaggagact gatggccacg ggcagcccctt tggtgtaggt gtttacaaat   4260
ctgttgagct gggagggatg catgcggggg gagatgaggt gcatcttggc ctggatcttg    4320
agattggcga tgttaccgcc cagatcccgc ctggggttca tgttgtgcag gaccaccagc    4380
acggtgtatc cggtgcactt ggggaattta tcatgcaact tggaagggaa ggcgtgaaag    4440
aatttggcga cgcccttgtg tccgcccagg ttttccatgc actcatccat gatgatggca    4500
```

```
atgggcccgt gggcggcggc ctgggcaaag acgtttcggg ggtcggacac atcatagttg   4560
tggtcctggg tgaggtcatc ataggccatt ttaatgaatt tggggcggag ggtgccggac   4620
tgggggacaa aggtaccctc gatcccgggg gcgtagttcc cctcacagat ctgcatctcc   4680
caggctttga gctcagaggg ggggatcatg tccacctgcg gggcgataaa gaacacggtt   4740
tccggggcgg gggagatgag ctgggccgaa agcaagttcc ggagcagctg ggacttgccg   4800
cagccggtgg ggccgtaaat gaccccgatg accggctgca ggtggtagtt gagggagaga   4860
cagctgccgt cctcccggag ggggggggcc acctcgttca tcatctcgcg cacgtgcatg   4920
ttctcgcgca ccagttccgc caggaggcgc tctcccccca gagataggag ctcctggagc   4980
gaggcgaagt ttttcagcgg cttgagtccg tcggccatgg gcattttgga gagggtctgt   5040
tgcaagagtt ccaagcggtc ccagagctcg gtgatgtgct ctacggcatc tcgatccagc   5100
agacctcctc gtttcgcggg ttgggacgac tgcgggagta gggcaccaga cgatgggcgt   5160
ccagcgcagc cagggtccgg tccttccagg gccgcagcgt ccgcgtcagg gtggtctccg   5220
tcacggtgaa ggggtgcgcg ccgggctggg cgcttgcgag ggtgcgcttc aggctcatcc   5280
ggctggtcga aaaccgctcc cgatcggcgc cctgcgcgtc ggccaggtag caattgacca   5340
tgagttcgta gttgagcgcc tcggccgcgt ggcctttggc gcggagctta cctttggaag   5400
tctgcccgca ggcgggacag aggagggact tgagggcgta gagcttgggg gcgaggaaga   5460
cggaatcggg ggcgtaggcg tccgcgccgc agtgggcgca gacggtctcg cactccacga   5520
gccaggtgag gtcgggctgg tcggggtcaa aaaccagttt cccgccgttc tttttgatgc   5580
gtttcttacc tttggtctcc atgagctcgt gtccccgctg ggtgacaaag aggctgtccg   5640
tgtccccgta gaccgacttt atgggccggt cctcgagcgg tgtgccgcgg tcctcctcgt   5700
agaggaaccc cgcccactcc gagacgaaag cccgggtcca ggccagcacg aaggaggcca   5760
cgtgggacgg gtagcggtcg ttgtccacca gcgggtccac ttttttccagg gtatgcaaac   5820
acatgtcccc ctcgtccaca tccaggaagg tgattggctt gtaagtgtag gccacgtgac   5880
cgggggtccc ggccgggggg gtataaaagg gggcggggccc ctgctcgtcc tcactgtctt   5940
ccggatcgct gtccaggagc gccagctgtt ggggtaggta ttccctctcg aaggcgggca   6000
tgacctcggc actcaggttg tcagtttcta gaaacgagga ggatttgata ttgacggtgc   6060
cagcggagat gcctttcaag agccctcgt ccatctggtc agaaaagacg attttttgt    6120
tgtcgagctt ggtggcgaag gagccgtaga gggcgttgga aaggagcttg gcgatggagc   6180
gcatggtctg gtttttttcc ttgtcggcgc gctccttggc cgcgatgttg agctgcacgt   6240
actcgcgcgc cacgcacttc cattcgggga agacggtggt catctcgtcg ggcacgattc   6300
tgacctgcca acctcgatta tgcagggtga tgaggtccac actggtggcc acctcgccgc   6360
gcaggggctc gttggtccag cagaggcggc cgcccttgcg cgagcagaag gggggcagag   6420
ggtccagcat gacctcgtcg gggggtcgg catcgatggt gaagatgccg ggcaggagat   6480
cggggtcgaa gtagctgatg gaagtggcca gatcgtccag ggaagcttgc cattcgcgca   6540
cggccagcgc gcgctcgtag ggactgaggg gcgtgcccca gggcatgggg tgggtgagcg   6600
cggaggcgta catgccgcag atgtcgtaga cgtagagggg ctcctcgagg atgccgatgt   6660
aggtggggta gcagcgcccc ccgcggatgc tggcgcgcac gtagtcatac agctcgtgcg   6720
agggcgcgag gagccccggg cccaggttgg tgcgactggg cttttcggcg cggtagacga   6780
tctggcgaaa gatggcatgc gagttggagg agatggtggg cctttggaag atgttgaagt   6840
gggcgtgggg gaggccgacc gagtcgcgga tgaagtgggc gtaggagtct tgcagtttgg   6900
```

```
cgacgagctc ggcggtgacg aggacgtcca gagcgcagta gtcgagggtc tcctggatga   6960
tgtcatactt gagctggccc ttttgtttcc acagctcgcg gttgagaagg aactcttcgc   7020
ggtccttcca gtactcttcg aggggggaacc cgtcctgatc tgcacggtaa gagcctagca   7080
tgtagaactg gttgacggcc ttgtaggcgc agcagcccct ctccacgggg agggcgtagg   7140
cctgggcggc cttgcgcagg gaggtgtgcg tgagggcgaa ggtgtccctg accatgacct   7200
tgaggaactg gtgcttgaaa tcgatatcgt cgcagccccc ctgctcccag agctggaagt   7260
ccgtgcgctt cttgtaggcg gggttgggca aagcgaaagt aacatcgttg aaaaggatct   7320
tgcccgcgcg gggcataaag ttgcgagtga tgccgaaagg ctggggcacc tcggcccggt   7380
tgttgatgac ctgggcggcg agcacgatct cgtcgaaacc gttgatgttg tgcccacga    7440
tgtagagttc cacgaatcgc gggcggccct tgacgtgggg cagcttcttg agctcctcgt   7500
aggtgagctc gtcggggtcg ctgagaccgt gctgctcgag cgcccagtcg gcgagatggg   7560
ggttggcgcg gaggaaggaa gtccagagat ccacggccag ggcggtttgc agacggtccc   7620
ggtactgacg gaactgctgc ccgacggcca ttttttcggg ggtgacgcag tagaaggtgc   7680
gggggtcccc gtgccagcgg tcccatttga gctggagggc gagatcgagg gcgagctcga   7740
cgaggcggtc gtcccctgag agtttcatga ccagcatgaa ggggacgagc tgcttgccga   7800
aggaccccat ccaggtgtag gtttccacat cgtaggtgag gaagagcctt tcggtgcgag   7860
gatgcgagcc gatggggaag aactggatct cctgccacca attggaggaa tggctgttga   7920
tgtgatggaa gtagaaatgc cgacggcgcg ccgaacactc gtgcttgtgt ttatacaagc   7980
ggccacagtg ctcgcaacgc tgcacgggat gcacgtgctg cacgagctgt acctgagttc   8040
ctttgacgag gaatttcagt gggaagtgga gtcgtggcgc ctgcatctcg tgctgtacta   8100
cgtcgtggtg gtcggcctgg ccctcttctg cctcgatggt ggtcatgctg acgagcccgc   8160
gcggaggca ggtccagacc tcggcgcgag cgggtcggag agcgaggacg agggcgcgca    8220
ggccggagct gtccagggtc ctgagacgct gcggagtcag gtcagtgggc agcggcggcg   8280
cgcggttgac ttgcaggagt ttttccaggg cgcgcgggag gtccagatgg tacttgatct   8340
ccaccgcgcc gttggtggcg acgtcgatgg cttgcagggt cccgtgcccc tggggtgtga   8400
ccaccgtccc ccgtttcttc ttgggcggct ggggcgacgg gggcggtgcc tcttccatgg   8460
ttagaagcgg cggcgaggac gcgcgccggg cggcagaggc ggctcgggc ccggaggcag    8520
gggcggcagg ggcacgtcgg cgccgcgcgc gggtaggttc tggtactgcg cccggagaag   8580
actggcgtga gcgacgacgc gacggttgac gtcctggatc tgacgcctct gggtgaaggc   8640
cacgggaccc gtgagtttga acctgaaaga gagttcgaca gaatcaatct cggtatcgtt   8700
gacggcggcc tgccgcagga tctcttgcac gtcgcccgag ttgtcctggt aggcgatctc   8760
ggtcatgaac tgctcgatct cctcctcctg aaggtctccg cgaccggcgc gctccacggt   8820
ggccgcgagg tcgttggaga tgcggcccat gagctgcgaa aaggcgttca tgcccgcctc   8880
gttccagacg cggctgtaga ccacgacgcc ctcgggatcg cgggcgcgca tgaccacctg   8940
ggcgaggttg agctccacgt ggcgcgtgaa gaccgcgtag ttgcagaggc gctggtagag   9000
gtagttgagc gtggtggcga tgtgctcggt gacgaagaaa tacatgatcc agcggcggag   9060
cggcatctcg ctgacgtcgc ccagcgcctc caagcgttcc atggcctcgt aaaagtccac   9120
ggcgaagttg aaaaactggg agttgcgcgc cgagacggtc aactcctcct ccagaagacg   9180
gatgagctcg gcgatggtgg cgcgcacctc gcgctcgaag gcccccggga gttcctccac   9240
```

```
ttcctcctct tcttcctcct ccactaacat ctcttctact tcctcctcag gcggtggtgg   9300
tggcggggga gggggcctgc gtcgccggcg gcgcacgggc agacggtcga tgaagcgctc   9360
gatggtctcg ccgcgccggc gtcgcatggt ctcggtgacg gcgcgcccgt cctcgcgggg   9420
ccgcagcgtg aagacgccgc cgcgcatctc caggtggccg ggggggtccc cgttgggcag   9480
ggagagggcg ctgacgatgc atcttatcaa ttgccccgta gggactccgc gcaaggacct   9540
gagcgtctcg agatccacgg gatctgaaaa ccgttgaacg aaggcttcga gccagtcgca   9600
gtcgcaaggt aggctgagca cggtttcttc tgccgggtca tgttggggag cggggcgggc   9660
gatgctgctg gtgatgaagt tgaaataggc ggttctgaga cggcggatgg tggcgaggag   9720
caccaggtct ttgggcccgg cttgctggat gcgcagacgg tcggccatgc cccaggcgtg   9780
gtcctgacac ctggccaggt ccttgtagta gtcctgcatg agccgctcca cgggcacctc   9840
ctcctcgccc gcgcggccgt gcatgcgcgt gagcccgaag ccgcgctggg gctggacgag   9900
cgccaggtcg gcgacgacgc gctcggcgag gatggcctgc tggatctggg tgagggtggt   9960
ctggaagtcg tcaaagtcga cgaagcggtg gtaggctccg gtgttgatgg tgtaggagca  10020
gttggccatg acggaccagt tgacggtctg gtggcccgga cgcacgagct cgtggtactt  10080
gaggcgcgag taggcgcgcg tgtcgaagat gtagtcgttg caggtgcgca ccaggtactg  10140
gtagccgatg aggaagtgcg gcggcggctg gcggtagagc ggccatcgct cggtggcggg  10200
ggcgccgggc gcgaggtcct cgagcatggt gcggtggtag ccgtagatgt acctggacat  10260
ccaggtgatg ccggcggcgg tggtggaggc gcgcgggaac tcgcggacgc ggttccagat  10320
gttgcgcagc ggcaggaagt agttcatggt gggcacggtc tggcccgtga ggcgcgcgca  10380
gtcgtggatg ctctatacgg gcaaaaacga aagcggtcag cggctcgact ccgtggcctg  10440
gaggctaagc gaacggggttg ggctgcgcgt gtaccccggt tcgaatctcg aatcaggctg  10500
gagccgcagc taacgtggta ctggcactcc cgtctcgacc caagcctgca ccaaccctcc  10560
aggatacgga ggcgggtcgt tttgcaactt ttttggagg ccggaaatga aactagtaag  10620
cgcggaaagc ggccgaccgc gatggctcgc tgccgtagtc tggagaagaa tcgccagggt  10680
tgcgttgcgt tgtgccccgg ttcgaggccg ccggattcc gcggctaacg agggcgtggc  10740
tgccccgtcg tttccaagac cccatagcca gccgacttct ccagttacgg agcgagcccc  10800
tcttttgttt tgtttgtttt tgccagatgc atcccgtact gcggcagatg cgcccccacc  10860
accctccacc gcaacaacag cccctcctc cacagccggc gcttctgccc ccgccccagc  10920
agcagcagca acttccagcc acgaccgccg cggccgccgt gagcggggct ggacagactt  10980
ctcagtatga tcacctggcc ttggaagagg gcgagggggct ggcgcgcctg ggggcgtcgt  11040
cgccggagcg gcaccgcgc gtgcagatga aaagggacgc tcgcgaggcc tacgtgccca  11100
agcagaacct gttcagagac aggagcggcg aggagcccga ggagatgcgc gcggcccggt  11160
tccacgcggg gcgggagctg cggcgcggcc tggaccgaaa gagggtgctg agggacgagg  11220
atttcgaggc ggacgagctg acggggatca gccccgcgcg cgcgcacgtg gccgcggcca  11280
acctggtcac ggcgtacgag cagaccgtga aggaggagag caacttccaa aaatccttca  11340
acaaccacgt gcgcacccctg atcgcgcgcg aggaggtgac cctgggcctg atgcacctgt  11400
gggacctgct ggaggccatc gtgcagaacc ccaccagcaa gccgctgacg gcgcagctgt  11460
tcctggtggt gcagcatagt cgggacaacg aggcgttcag ggaggcgctg ctgaatatca  11520
ccgagcccga gggccgctgg ctcctggacc tggtgaacat tctgcagagc atcgtggtgc  11580
aggagcgcgg gctgccgctg tccgagaagc tggcggccat caacttctcg gtgctgagtc  11640
```

```
tgggcaagta ctacgctagg aagatctaca agaccccgta cgtgcccata gacaaggagg   11700
tgaagatcga cgggttttac atgcgcatga ccctgaaagt gctgaccctg agcgacgatc   11760
tgggggtgta ccgcaacgac aggatgcacc gcgcggtgag cgccagcagg cggcgcgagc   11820
tgagcgacca ggagctgatg cacagcctgc agcgggccct gaccggggcc gggaccgagg   11880
gggagagcta ctttgacatg ggcgcggacc tgcactggca gcccagccgc cgggccttgg   11940
aggcggcagg cggtccccc tacatagaag aggtggacga tgaggtggac gaggaggggcg    12000 agtacctgga agactgatgg cgcgaccgta tttttgctag atgcaacaac agccacctcc   12060
tgatcccgcg atgcgggcgg cgctgcagag ccagccgtcc ggcattaact cctcggacga   12120
ttggacccag gccatgcaac gcatcatggc gctgacgacc cgcaaccccg aagcctttag   12180
acagcagccc caggccaacc ggctctcggc catcctggag gccgtggtgc cctcgcgctc   12240
caaccccacg cacgagaagg tcctggccat cgtgaacgcg ctggtggaga caaggccat    12300 ccgcggcgac gaggccggcc tggtgtacaa cgcgctgctg gagcgcgtgg cccgctacaa   12360
cagcaccaac gtgcagacca acctggaccg catggtgacc gacgtgcgcg aggccgtggc   12420
ccagcgcgag cggttccacc gcgagtccaa cctgggatcc atggtggcgc tgaacgcctt   12480
cctcagcacc cagcccgcca acgtgccccg ggccaggag gactacacca acttcatcag    12540
cgccctgcgc ctgatggtga ccgaggtgcc ccagagcgag gtgtaccagt ccgggccgga   12600
ctacttcttc cagaccagtc gccagggctt gcagaccgtg aacctgagcc aggcgttcaa   12660
gaacttgcag ggcctgtggg gcgtgcaggc cccggtcggg gaccgcgcga cggtgtcgag   12720
cctgctgacg ccgaactcgc gcctgctgct gctgctggtg gccccttca cggacagcgg    12780 cagcatcaac cgcaactcgt acctgggcta cctgattaac ctgtaccgcg aggccatcgg   12840
ccaggcgcac gtggacgagc agacctacca ggagatcacc cacgtgagcc gcgccctggg   12900
ccaggacgac ccgggcaatc tggaagccac cctgaactt ttgctgacca accggtcgca    12960
gaagatcccg ccccagtaca cgctcagcgc cgaggaggag cgcatcctgc gatacgtgca   13020
gcagagcgtg ggcctgttcc tgatgcagga gggggccacc cccagcgccg cgctcgacat   13080
gaccgcgcgc aacatggagc ccagcatgta cgccagcaac cgcccgttca tcaataaact   13140
gatggactac ttgcatcggg cggccgccat gaactctgac tatttcacca acgccatcct   13200 gaatcccac tggctcccgc cgccggggtt ctacacgggc gagtacgaca tgcccgaccc    13260
caatgacggg ttcctgtggg acgatgtgga cagcagcgtg ttctcccccc gaccgggtgc   13320
taacgagcgc cccttgtgga agaaggaagg cagcgaccga cgcccgtcct cggcgctgtc   13380
cggccgcgag ggtgctgccg cggcggtgcc cgaggccgcc agtccttcc cgagcttgcc    13440 cttctcgctg aacagtattc gcagcagcga gctgggcagg atcacgcgcc cgcgcttgct   13500
gggcgaggag gagtacttga atgactcgct gttgagaccc gagcgggaga agaacttccc   13560
caataacggg atagagagcc tggtggacaa gatgagccgc tggaagacgt atgcgcagga   13620
gcacagggac gatccgtcgc aggggggccac gagccggggc agcgccgccc gtaaacgccg   13680
gtggcacgac aggcagcggg gactgatgtg ggacgatgag gattccgccg acgacagcag   13740
cgtgttggac ttgggtggga gtggtaaccc gttcgctcac ctgcgcccc gcatcgggcg    13800 catgatgtaa gagaaaccga aaataaatga tactcaccaa ggccatggcg accagcgtgc   13860
gttcgtttct tctctgttgt tgtatctagt atgatgaggc gtgcgtaccc ggagggtcct   13920
cctccctcgt acgagagcgt gatgcagcag gcgatggcgg cggcggcggc gatgcagccc   13980
```

```
ccgctggagg ctccttacgt gccccccgcgg tacctggcgc ctacggaggg gcggaacagc    14040
attcgttact cggagctggc acccttgtac gataccaccc ggttgtacct ggtggacaac    14100
aagtcggcgg acatcgcctc gctgaactac cagaacgacc acagcaactt cctgaccacc    14160
gtggtgcaga acaatgactt cacccccacg gaggccagca cccagaccat caactttgac    14220
gagcgctcgc ggtggggcgg tcagctgaaa accatcatgc acaccaacat gcccaacgtg    14280
aacgagttca tgtacagcaa caagttcaag gcgcgggtga tggtctcccg caagacccccc   14340 aacggggtga cagtgacaga tggtagtcag gatatcttgg agtatgaatg ggtggagttt    14400
gagctgcccg aaggcaactt ctcggtgacc atgaccatcg acctgatgaa caacgccatc    14460
atcgacaatt acttggcggt ggggcggcag aacggggtcc tggagagcga tatcggcgtg    14520
aagttcgaca ctaggaactt caggctgggc tgggaccccg tgaccgagct ggtcatgccc    14580
ggggtgtaca ccaacgaggc cttccacccc gatattgtct tgctgcccgg ctgcggggtg    14640
gacttcaccg agagccgcct cagcaacctg ctgggcattc gcaagaggca gcccttccag    14700
gagggcttcc agatcatgta cgaggatctg gaggggggca acatcccccgc gctcctggat    14760 gtcgacgcct atgagaaaag caaggaggag agcgccgccg cggcgactgc agctgtagcc    14820
accgcctcta ccgaggtcag gggcgataat tttgccagcc ctgcagcagt ggcagcggcc    14880
gaggcggctg aaaccgaaag taagatagtc attcagccgg tggagaagga tagcaaggac    14940
aggagctaca acgtgctgcc ggacaagata aacaccgcct accgcagctg gtacctggcc    15000
tacaactatg gcgaccccga aagggcgtg cgctcctgga cgctgctcac cacctcggac    15060
gtcacctgcg cgtggagca agtctactgg tcgctgcccg acatgatgca agacccggtc    15120
accttccgct ccacgcgtca agttagcaac tacccggtgg tgggcgccga gctcctgccc    15180
gtctactcca agagcttctt caacgagcag gccgtctact cgcagcagct gcgcgccttc    15240
acctcgctca cgcacgtctt caaccgcttc cccgagaacc agatcctcgt ccgcccgccc    15300
gcgcccacca ttaccaccgt cagtgaaaac gttcctgctc tcacagatca cgggacccctg   15360 ccgctgcgca gcagtatccg gggagtccag cgcgtgaccg ttactgacgc cagacgccgc    15420
acctgcccct acgtctacaa ggccctgggc atagtcgcgc cgcgcgtcct ctcgagccgc    15480
accttctaaa aaatgtccat tctcatctcg cccagtaata acaccggttg gggcctgcgc    15540
gcgcccagca agatgtacgg aggcgctcgc caacgctcca cgcaacaccc cgtgcgcgtg    15600
cgcgggcact tccgcgctcc ctggggcgcc ctcaagggcc gcgtgcggtc gcgcaccacc    15660
gtcgacgacg tgatcgacca ggtggtggcc gacgcgcgca actacacccc cgccgccgcg    15720
cccgtctcca ccgtggacgc cgtcatcgac agcgtggtgg ccgacgcgcg ccggtacgcc    15780
cgcgccaaga gccggcggcg gcgcatcgcc cggcggcacc ggagcacccc cgccatgcgc    15840
gcggcgcgag ccttgctgcg cagggccagg cgcacgggac gcagggccat gctcagggcg    15900
gccagacgcg cggcttcagg cgccagcgcc ggcaggaccc ggagacgcgc ggccacggcg    15960
gcggcagcgg ccatcgccag catgtcccgc ccgcggcgag ggaacgtgta ctgggtgcgc    16020
gacgccgcca ccggtgtgcg cgtgcccgtg cgcacccgcc cccctcgcac ttgaagatgt    16080
tcacttcgcg atgttgatgt gtcccagcgg cgaggaggat gtccaagcgc aaattcaagg    16140
aagagatgct ccaggtcatc gcgcctgaga tctacggccc cgcggtggtg aaggaggaaa    16200
gaaagccccg caaatcaag cgggtcaaaa aggacaaaaa ggaagaagat gacgatctgg    16260
tggagtttgt gcgcgagttc gccccccggc ggcgcgtgca gtggcgcggg cggaaagtgc    16320
acccggtgct gagacccggc accaccgtgg tcttcacgcc cggcgagcgc tccggcagcg    16380
```

```
cttccaagcg ctcctacgac gaggtgtacg gggacgagga catcctcgag caggcggccg   16440
agcgcctggg cgagtttgct tacgcaagc gcagccgccc cgccctgaag gaagaggcgg    16500
tgtccatccc gctggaccac ggcaacccca cgccgagcct caagcccgtg accctgcagc   16560
aggtgctgcc gagcgcagcg ccgcgccggg ggttcaagcg cgagggcgag gatctgtacc   16620
ccaccatgca gctgatggtg cccaagcgcc agaagctgga agacgtgctg gagaccatga   16680
aggtggaccc ggacgtgcag cccgaggtca aggtgcggcc catcaagcag gtggcccgg    16740
gcctgggcgt gcagaccgtg gacatcaaga tccccacgga gcccatggaa acgcagaccg   16800
agcccatgat caagcccagc accagcacca tggaggtgca gacggatccc tggatgccat   16860
cggctcctag ccgaagaccc cggcgcaagt acggcgcggc cagcctgctg atgcccaact   16920
acgcgctgca tccttccatc atccccacgc cgggctaccg cggcacgcgc ttctaccgcg   16980
gtcatacaac cagccgccgc cgcaagacca ccacccgccg ccgccgtcgc cgcacagccg   17040
ctgcatctac ccctgccgcc ctggtgcgga gagtgtaccg ccgcggccgc gcgcctctga   17100
ccctaccgcg cgcgcgctac cacccgagca tcgccattta aactttcgcc tgctttgcag   17160
atggccctca catgccgcct ccgcgttccc attacgggct accgaggaag aaaaccgcgc   17220
cgtagaaggc tggcggggaa cgggatgcgt cgccaccacc atcggcggcg gcgcgccatc   17280
agcaagcggt tgggggagg cttcctgccc gcgctgatcc ccatcatcgc cgcggcgatc    17340
ggggcgatcc ccggcattgc ttccgtggcg gtgcaggcct ctcagcgcca ctgagacact   17400
tggaaaacat cttgtaataa accaatggac tctgacgctc ctggtcctgt gatgtgtttt   17460
cgtagacaga tggaagacat caattttttcg tccctggctc cgcgacacgg cacgcggccg   17520
ttcatgggca cctggagcga catcggcacc agccaactga acggggcgc cttcaattgg    17580
agcagtctct ggagcgggct taagaatttc gggtccacgc ttaaaaccta tggcagcaag   17640
gcgtggaaca gcaccacagg gcaggcgctg agggataagc tgaaagagca gaacttccag   17700
cagaaggtgg tcgatgggct cgcctcgggc atcaacgggg tggtggacct ggccaaccag   17760
gccgtgcagc ggcagatcaa cagccgcctg acccggtgc cgcccgccgg ctccgtggag    17820
atgccgcagg tggaggagga gctgcctccc ctggacaagc ggggcgagaa gcgacccccgc   17880
cccgacgcgg aggagacgct gctgacgcac acgacgagc cgcccccgta cgaggaggcg    17940
gtgaaactgg gtctgcccac cacgcggccc atcgcgcccc tggccaccgg ggtgctgaaa   18000
cccgaaagta ataagcccgc gaccctggac ttgcctcctc ccgcttcccg cccctctaca   18060
gtggctaagc cctgccgcc ggtggccgtg gcccgcgcgc gacccggggg ctccgcccgc    18120
cctcatgcga actggcagag cactctgaac agcatcgtgg gtctgggagt gcagagtgtg   18180
aagcgccgcc gctgctatta aacctaccgt agcgcttaac ttgcttgtct gtgtgtgtat   18240
gtattatgtc gccgctgtcc gccagaagga ggagtgaaga ggcgcgtcgc cgagttgcaa   18300
gatgccaccc ccatcgatgc tgccccagtg ggcgtacatg cacatcgccg gacaggacgc   18360
ttcggagtac ctgagtccgg gtctggtgca gttcgcccgc gccacagaca cctacttcag   18420
tctggggaac aagtttagga accccacggt ggcgcccacg cacgatgtga ccaccgaccg   18480
cagccagcgc ctgacgctgc gcttcgtgcc cgtggaccgc gaggacaaca cctactcgta   18540
caaagtgcgc tacacgctgg ccgtgggcga caaccgcgtg ctggacatgg ccagcaccta   18600
ctttgacatc cgcggcgtgc tggatcgggg ccctagcttc aaaccctact ccggcaccgc   18660
ctacaacagc ctggctccca agggagcgcc caattccagc cagtgggagc aaaaaaaggc   18720
```

```
aggcaatggt gacactatgg aaacacacac atttggtgtg gccccaatgg gcggtgagaa   18780
tattacaatc gacggattac aaattggaac tgacgctaca gctgatcagg ataaaccaat   18840
ttatgctgac aaaacattcc agcctgaacc tcaagtagga gaagaaaatt ggcaagaaac   18900
tgaaagcttt tatggcggta gggctcttaa aaaagacaca agcatgaaac cttgctatgg   18960
ctcctatgct agacccacca atgtaaaggg aggtcaagct aaacttaaag ttggagctga   19020
tggagttcct accaaagaat ttgacataga cctggctttc tttgatactc ccggtggcac   19080
agtgaatgga caagatgagt ataaagcaga cattgtcatg tataccgaaa acacgtatct   19140
ggaaactcca gacacgcatg tggtatacaa accaggcaag gatgatgcaa gttctgaaat   19200
taacctggtt cagcagtcca tgcccaatag acccaactat attgggttca gagacaactt   19260
tattgggctc atgtattaca acagtactgg caatatgggg gtgctggctg gtcaggcctc   19320
acagctgaat gctgtggtcg acttgcaaga cagaaacacc gagctgtcat accagctctt   19380
gcttgactct ttgggtgaca gaacccggta tttcagtatg tggaatcagg cggtggacag   19440
ttatgatcct gatgtgcgca ttattgaaaa ccatggtgtg gaagacgaac ttcccaacta   19500
ttgcttcccc ctggatgggt ctggcactaa tgccgcttac caaggtgtga agtaaaaaaa   19560
tggtaacgat ggtgatgttg agagcgaatg ggaaaatgat gatactgtcg cagctcgaaa   19620
tcaattatgc aagggcaaca tttttgccat ggaaattaac ctccaagcca acctgtggag   19680
aagtttcctc tactcgaacg tggccctgta cctgcccgac tcttacaagt acacgccagc   19740
caacatcacc ctgcccacca acaccaacac ttatgattac atgaacggga gagtggtgcc   19800
tccctcgctg gtggacgcct acatcaacat cggggcgcgc tggtcgctgg accccatgga   19860
caacgtcaat cccttcaacc accaccgcaa cgcgggcctg cgctaccgct ccatgctcct   19920
gggcaacggg cgctacgtgc ccttccacat ccaggtgccc cagaaatttt cgccatcaa   19980 gagcctcctg ctcctgcccg gtcctacac ctacgagtgg aacttccgca aggacgtcaa   20040
catgatcctg cagagctccc tcggcaacga cctgcgcacg gacggggcct ccatctcctt   20100
caccagcatc aacctctacg ccaccttctt ccccatggcg cacaacacgg cctccacgct   20160
cgaggccatg ctgcgcaacg acaccaacga ccagtccttc aacgactacc tctcggcggc   20220
caacatgctc taccccatcc cggccaacgc caccaacgtg cccatctcca tcccctcgcg   20280
caactgggcc gccttccgcg gctggtcctt cacgcgcctc aagaccaagg agacgccctc   20340
gctgggctcc gggttcgacc cctacttcgt ctactcgggc tccatcccct acctcgacgg   20400
caccttctac ctcaaccaca ccttcaagaa ggtctccatc accttcgact cctccgtcag   20460
ctggcccggc aacgaccggc tcctgacgcc caacgagttc gaaatcaagc gcaccgtcga   20520
cggcgaggga tacaacgtgg cccagtgcaa catgaccaag gactggttcc tggtccagat   20580
gctggcccac tacaacatcg gctaccaggg cttctacgtg cccgagggct acaaggaccg   20640
catgtactcc ttcttccgca acttccagcc catgagccgc caggtggtgg acgaggtcaa   20700
ctacaaggac taccaggccg tcaccctggc ctaccagcac aacaactcgg gcttcgtcgg   20760
ctacctcgcg cccaccatgc gccagggcca gccctacccc gccaactacc cgtacccgct   20820
catcggcaag agcgccgtca ccagcgtcac ccagaaaaag ttcctctgcg acagggtcat   20880
gtggcgcatc cccttctcca gcaacttcat gtccatgggc gcgctcaccg acctcggcca   20940
gaacatgctc tatgccaact ccgcccacgc gctagacatg aatttcgaag tcgacccat   21000 ggatgagtcc acccttctct atgttgtctt cgaagtcttc gacgtcgtcc gagtgcacca   21060
gccccaccgc ggcgtcatcg aggccgtcta cctgcgcacc cccttctcgg ccggtaacgc   21120
```

```
caccacctaa attgctactt gcatgatggc tgagcccaca ggctccggcg agcaggagct   21180
cagggccatc atccgcgacc tgggctgcgg gccctacttc ctgggcacct tcgataagcg   21240
cttcccggga ttcatggccc cgcacaagct ggcctgcgcc atcgtcaaca cggccggccg   21300
cgagaccggg ggcgagcact ggctggcctt cgcctggaac ccgcgctcga acacctgcta   21360
cctcttcgac cccttcgggt tctcggacga gcgcctcaag cagatctacc agttcgagta   21420
cgagggcctg ctgcgccgta gcgccctggc caccgaggac cgctgcgtca ccctggaaaa   21480
gtccacccag accgtgcagg gtccgcgctc ggccgcctgc gggctcttct gctgcatgtt   21540
cctgcacgcc ttcgtgcact ggcccgaccg ccccatggca aagaaccccc ccatgaactt   21600
gctgacgggg gtgcccaacg gcatgctcca gtcgccccag gtggaaccca ccctgcgccg   21660
caaccaggag gcgctctacc gcttcctcaa ctcccactcc gcctactttc gctcccaccg   21720
cgcgcgcatc gagaaggcca ccgccttcga ccgcatgaac aatcaagaca tgtaaaccgt   21780
gtgtgtatgt ttaaaatatc ttttaataaa cagcacttta atgttacaca tgcatctgag   21840
atgattttat tttagaaatc gaaagggttc tgccgggtct cggcatggcc cgcgggcagg   21900
gacacgttgc ggaactggta cttggccagc cacttgaact cggggatcag cagtttgggc   21960
agcggggtgt cggggaagga gtcggtccac agcttccgcg tcagctgcag ggcgcccagc   22020
aggtcgggcg cggagatctt gaaatcgcag ttgggacccg cgttctgcgc gcgagagttg   22080
cggtacacgg ggttgcagca ctggaacacc atcagggccg ggtgcttcac gctcgccagc   22140
accgccgcgt cggtgatgct ctccacgtcg aggtcctcgg cgttggccat cccgaagggg   22200
gtcatcttgc aggtctgcct tcccatggtg ggcacgcacc cgggcttgtg gttgcaatcg   22260
cagtgcaggg ggatcagcat catctgggcc tggtcggcgt tcatccccgg gtacatggcc   22320
ttcatgaaag cctccaattg cctgaacgcc tgctgggcct ggctccctc ggtgaagaag   22380 accccgcagg acttgctaga gaactggttg gtggcacagc cggcatcgtg cacgcagcag   22440
cgcgcgtcgt tgttggccag ctgcaccacg ctgcgcccc agcggttctg ggtgatcttg   22500
gcccggtcgg ggttctcctt cagcgcgcgc tgcccgttct cgctcgccac atccatctcg   22560
atcatgtgct ccttctggat catggtggtc ccgtgcaggc accgcagttt gccctcggcc   22620
tcggtgcacc cgtgcagcca cagcgcgcac ccggtgcact cccagttctt gtgggcgatc   22680
tgggaatgcg cgtgcacgaa cccttgcagg aagcggccca tcatggtcgt cagggtcttg   22740
ttgctagtga aggtcaacgg gatgccgcgg tgctcctcgt tgatgtacag gtggcagatg   22800
cggcggtaca cctcgccctg ctcgggcatc agttggaagt tggctttcag gtcggtctcc   22860
acgcggtagc ggtccatcag catagtcatg atttccatgc ccttctccca ggccgagacg   22920
atgggcaggc tcatagggtt cttcaccatc atcttagcac tagcagccgc ggccagggg   22980 tcgctctcat ccagggtctc aaagctccgc ttgccgtcct tctcggtgat ccgcaccggg   23040
gggtagctga agcccacggc cgccagctcc tcctcggcct gtctttcgtc ctcgctgtcc   23100
tggctgacgt cctgcatgac cacatgcttg gtcttgcggg gtttcttctt gggcggcagt   23160
ggcggcggag atgcttgtgg cgaggggag cgcgagttct cgctcaccac tactatctct   23220
tcctcttctt ggtccgaggc cacgcggcgg taggtatgtc tcttcggggg cagaggcgga   23280
ggcgacgggc tctcgccgcc gcgacttggc ggatggctgg cagagcccct ccgcgttcg   23340 ggggtgcgct cccggcggcg ctctgactga cttcctccgc ggccggccat tgtgttctcc   23400
tagggaggaa caacaagcat ggagactcag ccatcgccaa cctcgccatc tgcccccacc   23460
```

-continued

```
gccggcgacg agaagcagca gcagcagaat gaaagcttaa ccgccccgcc gcccagcccc   23520
gcctccgacg cagccgcggt cccagacatg caagagatgg aggaatccat cgagattgac   23580
ctgggctatg tgacgcccgc ggagcatgag gaggagctgg cagtgcgctt tcaatcgtca   23640
agccaggaag ataaagaaca gccagagcag gaagcagaga acgagcagag tcaggctggg   23700
ctcgagcatg gcgactacct ccacctgagc ggggaggagg acgcgctcat caagcatctg   23760
gcccggcagg ccaccatcgt caaggacgcg ctgctcgacc gcaccgaggt gcccctcagc   23820
gtggaggagc tcagccgcgc ctacgagctc aacctcttct cgccgcgcgt gccccccaag   23880
cgccagccca acggcacctg cgagcccaac ccccgcctca acttctaccc ggtcttcgcg   23940
gtgcccgagg ccctggccac ctaccacatc tttttcaaga accaaaagat ccccgtctcc   24000
tgccgcgcca accgcacccg cgccgacgcc ctcttcaacc tgggtcccgg cgcccgccta   24060
cctgatatcg cctccttgga agaggttccc aagatcttcg agggtctggg cagcgacgag   24120
actcgggccg cgaacgctct gcaaggagaa ggaggaggag agcatgagca ccacagcgcc   24180
ctggtcgagt tggaaggcga caacgcgcgg ctggcggtgc tcaaacgcac ggtcgagctg   24240
acccatttcg cctacccggc tctgaacctg cccccgaaag tcatgagcgc ggtcatggac   24300
caggtgctca tcaagcgcgc gtcgcccatc tccgaggacg agggcatgca agactccgag   24360
gagggcaagc ccgtggtcag cgacgagcag ctggcccggt ggctgggtcc taatgctacc   24420
cctcaaagtt tggaagagcg gcgcaagctc atgatggccg tggtcctggt gaccgtggag   24480
ctggagtgcc tgcgccgctt cttcgccgac gcggagaccc tgcgcaaggt cgaggagaac   24540
ctgcactacc tcttcaggca cggggttcgt cgccaggcct gcaagatctc caacgtggag   24600
ctgaccaacc tggtctccta catgggcatc ttgcacgaga accgcctggg gcagaacgtg   24660
ctgcacacca ccctgcgcgg ggaggcccgc cgcgactaca tccgcgactg cgtctacctc   24720
tacctctgcc acacctggca gacgggcatg ggcgtgtggc agcagtgtct ggaggagcag   24780
aacctgaaag agtctgcaa gctcctgcaa aagaacctca agggtctgtg gacccgggttc   24840 gacgagcgga ccaccgcctc ggacctggcc gacctcatct tccccgagcg cctcaggctg   24900
acgctgcgca acggcctgcc cgactttatg agccaaagca tgttgcaaaa ctttcgctct   24960
ttcatcctcg aacgctccgg aatcctgccc gccacctgct ccgcgctgcc ctcggacttc   25020
gtgccgctga ccttccgcga gtgccccccg ccgctgtgga gccactgcta cctgctgcgc   25080
ctggccaact acctggccta ccactcggac gtgatcgagg acgtcagcgg cgagggcctg   25140
ctcgagtgcc actgccgctg caacctctgc acgccgcacc gctccctggc ctgcaacccc   25200
cagctgctga gcgagaccca gatcatcggc accttcgagt tgcaagggcc cagcgagggc   25260
gagggagcca ggggggtct gaaactcacc ccggggctgt ggacctcggc ctacttgcgc   25320
aagttcgtgc ccgaggatta ccatcccttc gagatcaggt tctacgagga ccaatcccag   25380
ccgcccaagg ccgagctgtc ggcctgcgtc atcacccagg gggcgatcct ggcccaattg   25440
caagccatcc agaaatcccg ccaagaattc ttgctgaaaa agggccgcgg ggtctacctc   25500
gaccccagda ccggtgagga gctcaacccc ggcttccccc aggatgcccc gaggaaacaa   25560
gaagctgaaa gtggagctgc cgcccgtgga ggatttggag gaagactggg agaacagcag   25620
tcaggcagag gagatggagg aagactggga cagcactcag gcagaggagg acagcctgca   25680
agacagtctg gaggaagacg aggaggaggc agaggaggag gtggaagaag cagccgccgc   25740
cagaccgtca tcctcggcgg gggagaaagc aagcagcacg gataccatct ccgctccggg   25800
tcggggtccc gctcggcccc acagtagatg ggacgagacc gggcgattcc cgaaccccac   25860
```

```
cacccagacc ggtaagaagg agcggcaggg atacaagtcc tggcgggggc acaaaaacgc  25920
catcgtctcc tgcttgcagg cctgcggggg caacatctcc ttcacccggc gctacctgct  25980
cttccaccgc ggggtgaact tcccccgcaa catcttgcat tactaccgtc acctccacag  26040
cccctactac ttccaagaag aggcagcagc agcagaaaaa gaccagaaaa ccagctagaa  26100
aatccacagc ggcggcagcg gcaggtggac tgaggatcgc ggcgaacgag ccggcgcaga  26160
cccgggagct gaggaaccgg atctttccca ccctctatgc catcttccag cagagtcggg  26220
ggcaggagca ggaactgaaa gtcaagaacc gttctctgcg ctcgctcacc cgcagttgtc  26280
tgtatcacaa gagcgaagac caacttcagc gcactctcga ggacgccgag gctctcttca  26340
acaagtactg cgcgctcact cttaaagagt agcccgcgcc cgcccagtcg cagaaaaagg  26400
cgggaattac gtcacctgtg cccttcgccc tagccgcctc cacccagcac cgccatgagc  26460
aaagagattc ccacgcctta catgtggagc taccagcccc agatgggcct ggccgccggc  26520
gccgccagg actactccac ccgcatgaat tggctcagcg ccgggcccgc gatgatctca  26580
cgggtgaatg acatccgcgc ccaccgaaac cagatactcc tagaacagtc agcgctcacc  26640
gccacgcccc gcaatcacct caatccgcgt aattggcccg ccgccctggt gtaccaggaa  26700
attccccagc ccacgaccgt actacttccg cgagacgccc aggccgaagt ccagctgact  26760
aactcaggtg tccagctggc gggcggcgcc accctgtgtc gtcaccgccc cgctcagggt  26820
ataaagcggc tggtgatccg gggcagaggc acacagctca cgacgaggt ggtgagctct  26880
tcgctgggtc tgcgacctga cggagtcttc caactcgccg gatcggggag atcttccttc  26940
acgcctcgtc aggcggtcct gactttggag agttcgtcct cgcagcccg ctcgggcggc  27000
atcggcactc tccagttcgt ggaggagttc actccctcgg tctacttcaa cccttctcc  27060
ggctcccccg gccactaccc ggacgagttc atcccgaact ttgacgccat cagcgagtcg  27120
gtggacggct acgattgaat gtcccatggt ggcgcggctg acctagctcg gcttcgacac  27180
ctggaccact gccgccgctt tcgctgcttc gctcgggacc tcgccgagtt cacctacttt  27240
gagctgcccg aggagcatcc tcagggcccg gcccacggag tgcggatcgt cgtcgaaggg  27300
ggcctagact cccacctgct tcggatcttc agccagcgcc cgatcctggt cgagcgccaa  27360
cagggcaaca ccctcctgac cctctactgc atctgcgacc accccggcct gcatgaaagt  27420
ctttgttgtc tgctgtgtac tgagtataat aaaagctgag atcagcgact actccggact  27480
caactgtggt gtttctgcat ccatcaatcg gtctctgacc ttcaccggga acgagaccga  27540
gctccaggtc cagtgtaagc cccacaagaa gtacctcacc tggctgtacc agggctcccc  27600
gatcgccgtt gttaaccact gcgacgacga cggagtcctg ctgaacggcc ccgccaacct  27660
tacttttttcc acccgcagaa gcaagctact gctcttccga cccttcctcc ccggcaccta  27720
tcagtgcatc tcgggaccct gccatcacac cttccacctg atcccgaata ccacctcttc  27780
cccagcaccg ctccccacta acaaccaaac taaccaccac caacgctacc gacgcgacct  27840
cgtttctgaa tctaatacca cccacaccgg aggtgagctc cgaggtcgca aaccctctgg  27900
gatttattac ggcccctggg aggtggtggg gttaatagct ttaggcttag tggcgggtgg  27960
gcttttggct ctctgctacc tataccctcc ttgcttttcc tacttagtgg tgctttgttg  28020
ctggtttaag aaatggggaa gatcacccta gtgtgcggtg tgctggtgac ggtggtgctt  28080
tcgattctgg gagggggaag cgcggctgta gtgacggaga agaaggccga tcctgcttg  28140
actttcaacc ccgataaatg ccggctgagt tttcagcccg atggcaatcg gtgcgcggtg  28200
```

```
ttgatcaagt gcggatggga atgcgagagc gtgttggtcc agtataaaaa caagacctgg    28260
aacaatactc tcgcgtccac atggcagccc ggggacccg  agtggtacac cgtctctgtc    28320
cctggtgctg acggctccct ccgcacggtg aacaacactt tcattttga  gcacatgtgc    28380 gagaccgcca tgttcatgag caagcagtac ggtatgtggc ccccacgtaa agagaatatc    28440
gtggtcttct ccatcgctta cagcgcgtgc acggtgctaa tcaccgcgat cgtgtgcctg    28500
agcattcaca tgctcatcgc tattcgcccc agaaataatg ccgagaaaga gaaacagcca    28560
taacacactt ttcacatacc ttttcagac  catggcctct gttacaatcc ttatttattt    28620
tttgggactt gtgggcacta gcagcacttt tcagcatata aacaaaactg tttatgctgg    28680
ttcaaattct gtgttagctg acatcagtc  ataccagaaa gtttcatggt actggtatga    28740
taaaaatcaa acacccgtta cactctgcaa gggtccacaa cagcccgtaa accgtagtgg    28800
gatttttttt agctgtaatc ataataatat cacactactt tcaattacaa agcactatgc    28860
tggaacttac tatggaacca atttcaatat caaacatgac acttactata gtgtcagagt    28920
attggatcca actacccta  gaacaactac aaagcccacc acaactaaga agcccactac    28980
acctaagaag cctaccacgc ccaaaaccac taagacaact actaagacca ctaccacaga    29040
gccaaccaca accagcaccc acacttgcta taactcacaca cacacacaca cactgagctg    29100
acctcacagg caactactga aaatggtttt gccctgttac aaaagggga  aaacagtagc    29160 agcagtcctc tgcctaccac ccccagtgag gaaataccta aatccatggt tggcattatc    29220
gctgctgtag tggtgtgtat gctgattatc atcttgtgca tgatgtacta tgcctgctac    29280
tacagaaaac acaggctgaa caacaagctg accccctac  tgaatgttga ttttaatttt    29340
tttagaacca tgaagatcct aagccttttt tgtttttcta taattattac ctctgctatt    29400
tgtaactcag tggataagga cgttactgtc accactggct ctaattatac actgaaagga    29460
cctccctcag gtatgctttc gtggtattgc tattttggaa ctgatgtttc acaaactgaa    29520
ttgtgtaatt ttcaaaaagg caaaacccaa atcctaaaa  ttcataacta tcaatgcaat    29580
ggtactgatt tagtactgtt caatatcacg aaaacatatg ctggaagtta ttactgcccg    29640
ggagataatg ttgacaatat gattttttac gaattacaag tagttgatcc cactactcca    29700
gcaccaccca ccacaactac caaggcacat agcacagaca cacaggaaac cactccagag    29760
gcagaagtag cagagttagc aaaagcagatt catgaagatt cctttgttgc caataccccc    29820 acacacccg  gaccgcaatg tccagggcca ttagtcagcg gcattgtcgg tgtgctttgc    29880
gggttagcag ttataatcat ctgcatgttc atttttgctt gctgctacag aaggcttcac    29940
cgacaaaaat cagacccact gctgaacctc tatgtttaat ttttgatttt ccagagccat    30000
gaaggcactt agcactttag ttttttttgac cttgattggc attgttttta atagtaaaat    30060
taccagggtt agctttctca aacatgttaa tgttactgaa ggaaataata tcacactagt    30120
aggtgtagaa ggtgctcaaa acaccacctg gacaaaatac catctcgggt ggaaagatat    30180
ttgcacctgg aatgtcactt attttttgcat aggagttaat cttaccattg ttaatgctaa    30240
tcaatctcag aatggattaa ttaaagggca gagcgtgagt gttaccagtg atgggtacta    30300
tacccagcat aatttcaact acaacattac tgttataccaa ctgccaacac ctagcccacc    30360
tagcactact cagaccacac aaacaactca cactacacag agctccacaa ctaccatgca    30420
gaccactcag acaaccacat acactacttc ccctcagccc accaccacta cagcagaggc    30480
gagtagctca cccaccatca aagtggcatt tttaatgctg gccccatcta gcagtccac    30540 tgctagtacc aatgagcaga ctactgaatt tttgtccact attcagagca gcaccacagc    30600
```

```
tacctcgagt gccttctcta gcaccgccaa tctcacctcg ctttcctcta tgccaatcag   30660
taatgctact acctcccccg ctcctcttcc cactcctctg aagcaatccg agtccagcac   30720
gcagctgcag atcaccctgc tcattgtgat cggggtggtc atcctggcag tgctgctcta   30780
ctttatcttc tgccgtcgca tccccaacgc aaagccggcc tacaagccca ttgttatcgg   30840
gacgccggag ccgcttcagg tggagggagg tctaaggaat cttctcttct cttttacagt   30900
atggtgattt gaactatgat tcctagacat ttcattatca cttctctaat ctgtgtgctc   30960
caagtctgtg ccaccctcgc tctcgtggct aacgcgagtc cagactgcat tggagcgttc   31020
gcctcctacg tgctctttgc cttcatcacc tgcatctgct gctgtagcat agtctgcctg   31080
cttatcacct tcttccagtt cgttgactgg gtctttgtgc gcatcgccta cctgcgccac   31140
cacccccagt accgcgacca gagagtggcg caactgttga gactcatctg atgataagca   31200
tgcgggctct gctactactt ctcgcgcttc tgctagctcc cctcgccgcc ccctatccc    31260 tcaaatcccc cacccagtcc cctgaagagg ttcgaaaatg taaattccaa gaaccctgga   31320
aattcctttc atgctacaaa ctcaaatcag aaatgcaccc cagctggatc atgatcgttg   31380
gaatcgtgaa catccttgcc tgtaccctct tctcctttgt gatttacccc cgctttgact   31440
ttgggtggaa cgcacccgag gcgctctggc tcccgcctga tcccgacaca ccaccacagc   31500
agcagcagca aaatcaggca caggcacacg caccaccaca gcctaggcca caatacatgc   31560
ccatcttaaa ctatgaggcc gaggcacagc gagccatgct tcctgctatt agttacttca   31620
atctaaccgg cggagatgac tgaccccatg gccaacaaca ccgtcaacga cctcctggac   31680
atggacggcc gcgcctcgga gcagcgactc gcccaactcc gcatccgcca gcagcaggag   31740
agagccgtca aggagctgca ggatgcggtg gccatccacc agtgcaagag aggcatcttc   31800
tgcctggtga agcaggccaa gatctccttc gaggtcacgt ccaccgacca tcgcctctcc   31860
tacgagctcc tgcagcagcg ccagaagttc acctgcctgg tcggagtcaa ccccatcgtc   31920
atcacccagc agtctggcga taccaagggt tgcatccact gctcctgcga ctcccccgag   31980
tgcgttcaca ccctgatcaa gaccctctgc ggcctccgcg acctcctccc catgaactaa   32040
tcaactaacc ccctacccct ttaccctcca gtaaaaataa agattaaaaa tgattgaatt   32100
gatcaataaa gaatcactta cttgaaatct gaaaccaggt ctctgtccat gttttctgtc   32160
agcagcactt cactcccctc ttcccaactc tggtactgca ggccccggcg ggctgcaaac   32220
ttcctccaca ctctgaaggg gatgtcaaat tcctcctgtc cctcaatctt cattttatc    32280 ttctatcaga tgtccaaaaa gcgcgcgcgg gtggatgatg gcttcgaccc cgtgtacccc   32340
tacgatgcag acaacgcacc gactgtgccc ttcatcaacc ctcccttcgt ctcttcagat   32400
ggattccaag aaaagcccct gggggtgttg tccctgcgac tggccgaccc cgtcaccacc   32460
aagaatgggg ctgtcaccct caagctgggg gaggggtgg acctcgacga ctcgggaaaa    32520
ctcatctcca aaaatgccac caaggccact gcccctctca gtatttccaa cggcaccatt   32580
tcccttaaca tggctgcccc tttttacaac aacaatggaa cgttaagtct caatgtttct   32640
acaccattag cagtatttcc cacttttaac actttaggta tcagtcttgg aaacggtctt   32700
caaacttcta ataagttgct gactgtacag ttaactcatc ctcttacatt cagctcaaat   32760
agcatcacag taaaaacaga caaaggactc tatattaatt ctagtggaaa cagagggctt   32820
gaggctaaca taagcctaaa aagaggactg attttgatg gtaatgctat tgcaacatac    32880
cttggaagtg gtttagacta tggatcctat gatagcgatg gaaaaacaag acccatcatc   32940
```

```
accaaaattg gagcaggttt gaattttgat gctaataatg ccatggctgt gaagctaggc  33000
acaggtttaa gttttgactc tgccggtgcc ttaacagctg gaaacaaaga ggatgacaag  33060
ctaacacttt ggactacacc tgacccaagc cctaattgtc aattactttc agacagagat  33120
gccaaattta ccctatgtct tacaaaatgc ggtagtcaaa tactaggcac tgttgcagta  33180
gctgctgtta ctgtaggttc agcactaaat ccaattaatg acacagtaaa aagcgccata  33240
gtattcctta gatttgactc tgacggtgtg ctcatgtcaa actcatcaat ggtaggtgat  33300
tactggaact ttagggaagg acagaccacc caaagtgtgg cctatacaaa tgctgtggga  33360
ttcatgccca atctaggtgc atatcctaaa acccaaagca aaacaccaaa aaatagtata  33420
gtaagtcagg tatatttaaa tggagaaact actatgccaa tgacactgac ataactttc   33480 aatggcactg atgaaaaaga cacaacacct gtgagcactt actccatgac ttttacatgg  33540
cagtggactg gagactataa ggacaagaat attacctttg ctaccaactc ctttactttc  33600
tcctacatgg cccaagaata aaccctgcat gccaaccca ttgttccac cactatggaa    33660 aactctgaag cagaaaaaaa taaagttcaa gtgtttatt gattcaacag ttttcacaga   33720
attcgagtag ttattttccc tcctccctcc caactcatgg aatacaccac cctctcccca  33780
cgcacagcct taaacatctg aatgccattg gtaatgacca tggttttggt ctccacattc  33840
cacacagttt cagagcgagc cagtctcggg tcggtcaggg agatgaaacc ctccgggcac  33900
tcctgcatct gcacctcaaa gttcagtagc tgagggctgt cctcggtggt cgggatcaca  33960
gttatctgga agaagagcgg tgagagtcat aatccgcgaa cgggatcggg cggttgtggc  34020
gcatcaggcc ccgcagcagt cgctgtctgc gccgctccgt caagctgctg ctcaaggggt  34080
ctgggtccag ggactccctg cgcatgatgc cgatggccct gagcatcagt cgcctggtgc  34140
ggcgggcgca gcagcggatg cggatctcac tcaggtcgga gcagtacgtg cagcacagca  34200
ctaccaagtt gttcaacagt ccatagttca acgtgctcca gccaaaactc atctgtggaa  34260
ctatgctgcc cacatgtcca tcgtaccaga tcctgatgta aatcaggtgg cgccccctcc  34320
agaacacact gcccatgtac atgatctcct tgggcatgtg caggttcacc acctcccggt  34380
accacatcac ccgctggttg aacatgcagc cctggataat cctgcggaac cagatggcca  34440
gcaccgcccc gcccgccatg cagcgcaggg accccgggtc ctggcaatgg cagtggagca  34500
cccaccgctc acgccgtgg attaactggg agctgaacaa gtctatgttg cacagcaca    34560 ggcacacgct catgcatgtc ttcagcactc tcagttcctc gggggtcagg accatgtccc  34620
agggcacggg gaactcttgc aggacagtga acccggcaga acaggcagc cctcgcacac    34680 aacttacatt gtgcatggac agggtatcgc aatcaggcag caccggatga tcctccacca  34740
gagaagcgcg ggtctcggtc tcctcacagc gaggtaaggg ggccggcggt tggtacggat  34800
gatggcggga tgacgctaat cgtgttctgg atcgtgtcat gatggagctg tttcctgaca  34860
ttttcgtact tcacgaagca gaacctggta cgggcactgc acaccgctcg ccggcgacgg  34920
tctcggcgct tcgagcgctc ggtgttgaag ttatagaaca gccactccct cagagcgtgc  34980
agtatctcct gagcctcttg ggtgatgaaa atcccatccg ctctgatggc tctgatcaca  35040
tcggccacgg tggaatgggc cagacccagc cagatgatgc aattttgttg ggtttcggtg  35100
acggagggag agggaagaac aggaagaacc atgattaact ttattccaaa cggtctcgga  35160
gcacttcaaa atgcaggtcc cggaggtggc acctctcgcc cccactgtgt tggtggaaaa  35220
taacagccag gtcaaaggtg acacggttct cgagatgttc cacggtggct ccagcaaag   35280 cctccacgcg cacatccaga aacaagagga cagcgaaagc gggagcgttt tctaattcct  35340
```

```
caatcatcat attacactcc tgcaccatcc ccagataatt ttcattttc cagccttgaa   35400 tgattcgtat tagttcctga ggtaaatcca agccagccat gataaaaagc tcgcgcagag   35460
cgccctccac cggcattctt aagcacaccc tcataattcc aagagattct gctcctggtt   35520
cacctgcagc agattaacaa tgggaatatc aaaatctctg ccgcgatccc taagctcctc   35580
cctcaacaat aactgtatgt aatctttcat atcatctccg aaattttag ccatagggcc   35640 gccaggaata agagcagggc aagccacatt acagataaag cgaagtcctc cccagtgagc   35700
attgccaaat gtaagattga aataagcatg ctggctagac cctgtgatat cttccagata   35760
actggacaga aaatcaggca agcaattttt aagaaaatca acaaaagaaa agtcgtccag   35820
gtgcaggttt agagcctcag gaacaacgat ggaataagtg caaggagtgc gttccagcat   35880
ggttagtgtt tttttggtga tctgtagaac aaaaaataaa catgcaatat taaaccatgc   35940
tagcctggcg aacaggtggg taaatcactc tttccagcac caggcaggct acggggtctc   36000
cggcgcgacc ctcgtagaag ctgtcgccat gattgaaaag catcaccgag agaccttccc   36060
ggtggccggc atggatgatt cgagaagaag catacactcc gggaacattg catccgtga   36120 gtgaaaaaaa gcgacctata aagcctcggg gcactacaat gctcaatctc aattccagca   36180
aagccacccc atgcggatgg agcacaaaat tggcaggtgc gtaaaaaatg taattactcc   36240
cctcctgcac aggcagcaaa gcccccgctc cctccagaaa cacatacaaa gcctcagcgt   36300
ccatagctta ccgagcacgg caggcgcaag agtcagagaa aaggctgagc tctaacctga   36360
ctgcccgctc ctgtgctcaa tatatagccc taacctacac tgacgtaaag gccaaagtct   36420 aaaaatacc gccaaaatga cacacacgcc cagcacacgc ccagaaaccg gtgacacact   36480
caaaaaaata cgtgcgcttc ctcaaacgcc caaaccggcg tcatttccgg gttcccacgc   36540
tacgtcaccg ctcagcgact ttcaaattcc gtcgaccgtt aaaaacgtca ctcgccccgc   36600
ccctaacggt cgcccttctc tcggccaatc accttcctcc cttcccaaat tcaaacgcct   36660
catttgcata ttaacgcgca caaaaagttt gaggtatata tttgaatgat g         36711
```

<210> SEQ ID NO 7
<211> LENGTH: 114
<212> TYPE: PRT
<213> ORGANISM: Human adenovirus AdHu5

<400> SEQUENCE: 7

```
Met Val Leu Pro Ala Leu Pro Ala Pro Pro Val Cys Asp Ser Gln Asn
1               5                   10                  15

Glu Cys Val Gly Trp Leu Gly Val Ala Tyr Ser Ala Val Val Asp Val
                20                  25                  30

Ile Arg Ala Ala His Glu Gly Val Tyr Ile Glu Pro Glu Ala Arg
        35                  40                  45

Gly Arg Leu Asp Ala Leu Arg Glu Trp Ile Tyr Tyr Asn Tyr Tyr Thr
    50                  55                  60

Glu Arg Ser Lys Arg Arg Asp Arg Arg Arg Ser Val Cys His Ala
65                  70                  75                  80

Arg Thr Trp Phe Cys Phe Arg Lys Tyr Asp Tyr Val Arg Arg Ser Ile
                85                  90                  95

Trp His Asp Thr Thr Thr Asn Thr Ile Ser Val Val Ser Ala His Ser
                100                 105                 110

Val Gln
```

<210> SEQ ID NO 8
<211> LENGTH: 294
<212> TYPE: PRT
<213> ORGANISM: Human adenovirus AdHu5

<400> SEQUENCE: 8

Met Thr Thr Ser Gly Val Pro Phe Gly Met Thr Leu Arg Pro Thr Arg
1               5                   10                  15

Ser Arg Leu Ser Arg Arg Thr Pro Tyr Ser Arg Asp Arg Leu Pro Pro
            20                  25                  30

Phe Glu Thr Glu Thr Arg Ala Thr Ile Leu Glu Asp His Pro Leu Leu
        35                  40                  45

Pro Glu Cys Asn Thr Leu Thr Met His Asn Val Ser Tyr Val Arg Gly
    50                  55                  60

Leu Pro Cys Ser Val Gly Phe Thr Leu Ile Gln Glu Trp Val Val Pro
65                  70                  75                  80

Trp Asp Met Val Leu Thr Arg Glu Glu Leu Val Ile Leu Arg Lys Cys
                85                  90                  95

Met His Val Cys Leu Cys Cys Ala Asn Ile Asp Ile Met Thr Ser Met
            100                 105                 110

Met Ile His Gly Tyr Glu Ser Trp Ala Leu His Cys His Cys Ser Ser
        115                 120                 125

Pro Gly Ser Leu Gln Cys Ile Ala Gly Gly Gln Val Leu Ala Ser Trp
    130                 135                 140

Phe Arg Met Val Val Asp Gly Ala Met Phe Asn Gln Arg Phe Ile Trp
145                 150                 155                 160

Tyr Arg Glu Val Val Asn Tyr Asn Met Pro Lys Glu Val Met Phe Met
                165                 170                 175

Ser Ser Val Phe Met Arg Gly Arg His Leu Ile Tyr Leu Arg Leu Trp
            180                 185                 190

Tyr Asp Gly His Val Gly Ser Val Pro Ala Met Ser Phe Gly Tyr
        195                 200                 205

Ser Ala Leu His Cys Gly Ile Leu Asn Asn Ile Val Val Leu Cys Cys
    210                 215                 220

Ser Tyr Cys Ala Asp Leu Ser Glu Ile Arg Val Arg Cys Cys Ala Arg
225                 230                 235                 240

Arg Thr Arg Arg Leu Met Leu Arg Ala Val Arg Ile Ile Ala Glu Glu
                245                 250                 255

Thr Thr Ala Met Leu Tyr Ser Cys Arg Thr Glu Arg Arg Gln Gln
            260                 265                 270

Phe Ile Arg Ala Leu Leu Gln His His Arg Pro Ile Leu Met His Asp
    275                 280                 285

Tyr Asp Ser Thr Pro Met
    290

<210> SEQ ID NO 9
<211> LENGTH: 150
<212> TYPE: PRT
<213> ORGANISM: Human adenovirus AdHu5

<400> SEQUENCE: 9

Met Thr Thr Ser Gly Val Pro Phe Gly Met Thr Leu Arg Pro Thr Arg
1               5                   10                  15

Ser Arg Leu Ser Arg Arg Thr Pro Tyr Ser Arg Asp Arg Leu Pro Pro
            20                  25                  30

Phe Glu Thr Glu Thr Arg Ala Thr Ile Leu Glu Asp His Pro Leu Leu

```
                35                  40                  45
Pro Glu Cys Asn Thr Leu Thr Met His Asn Ala Trp Thr Ser Pro Ser
             50                  55                  60

Pro Pro Val Lys Gln Pro Gln Val Gly Gln Gln Pro Val Ala Gln Gln
 65                  70                  75                  80

Leu Asp Ser Asp Met Asn Leu Ser Glu Leu Pro Gly Glu Phe Ile Asn
                 85                  90                  95

Ile Thr Asp Glu Arg Leu Ala Arg Gln Glu Thr Val Trp Asn Ile Thr
                100                 105                 110

Pro Lys Asn Met Ser Val Thr His Asp Met Met Leu Phe Lys Ala Ser
            115                 120                 125

Arg Gly Glu Arg Thr Val Tyr Ser Val Cys Trp Glu Gly Gly Gly Arg
        130                 135                 140

Leu Asn Thr Arg Val Leu
145                 150

<210> SEQ ID NO 10
<211> LENGTH: 30842
<212> TYPE: DNA
<213> ORGANISM: Artificial
<220> FEATURE:
<223> OTHER INFORMATION: Viral vector based on Chimpanzee adenovirus C68

<400> SEQUENCE: 10
ccatcttcaa taatatacct caaactttt gtgcgcgtta atatgcaaat gaggcgtttg      60
aatttgggga ggaagggcgg tgattggtcg agggatgagc gaccgttagg ggcggggcga    120
gtgacgtttt gatgacgtgg ttgcgaggag gagccagttt gcaagttctc gtgggaaaag    180
tgacgtcaaa cgaggtgtgg tttgaacacg gaaatactca attttcccgc gctctctgac    240
aggaaatgag gtgtttctgg gcggatgcaa gtgaaaacgg gccattttcg cgcgaaaact    300
gaatgaggaa gtgaaaatct gagtaatttc gcgtttatgg cagggaggag tatttgccga    360
gggccgagta gactttgacc gattacgtgg gggtttcgat taccgtgttt ttcacctaaa    420
tttccgcgta cggtgtcaaa gtccggtgtt tttacgcgat cgctagcgac atcgatcaca    480
agtttgtaca aaaaagctga acgagaaacg taaaatgata taaatatcaa tatattaaat    540
tagattttgc ataaaaaaca gactacataa tactgtaaaa cacaacatat ccagtcacta    600
tggcggccgc cgattattc aacaaagcca cgttgtgtct caaaatctct gatgttacat    660
tgcacaagat aaaaatatat catcatgaac aataaaactg tctgcttaca taaacagtaa    720
tacaaggggt gttatgagcc atattcaacg ggaaacgtct gctcgaggc cgcgattaaa     780 ttccaacatg gatgctgatt tatatgggta taatgggct cgtgataatg tcgggcaatc    840
aggtgcgaca atctatcgat tgtatgggaa gcccgatgcg ccagagttgt ttctgaaaca    900
tggcaaaggt agcgttgcca atgatgttac agatgagatg gtcagactaa actggctgac    960
ggaatttatg cctcttccga ccatcaagca ttttatccgt actcctgatg atgcatggtt   1020
actcaccact gcgatcccg ggaaaacagc attccaggta ttagaagaat atcctgattc   1080
aggtgaaaat attgttgatg cgctggcagt gttcctgcgc cggttgcatt cgattcctgt   1140
ttgtaattgt ccttttaaca gcgatcgcgt atttcgtctc gctcaggcgc aatcacgaat   1200
gaataacggt ttggttgatg cgagtgattt tgatgacgag cgtaatggct ggcctgttga   1260
acaagtctgg aaagaaatgc ataagctttt gccattctca ccggattcag tcgtcactca   1320
tggtgatttc tcacttgata accttatttt tgacgagggg aaattaatag gttgtattga   1380
```

```
tgttggacga gtcggaatcg cagaccgata ccaggatctt gccatcctat ggaactgcct    1440
cggtgagttt tctccttcat tacagaaacg gcttttttcaa aaatatggta ttgataatcc   1500
tgatatgaat aaaattgcagt ttcatttgat gctcgatgag ttttttctaat cagaattggt  1560
taattggttg taacactggc acgcgtggat ccggcttact aaaagccaga taacagtatg    1620
cgtatttgcg cgctgatttt tgcggtataa gaatatatac tgatatgtat acccgaagta   1680
tgtcaaaaag aggtatgcta tgaagcagcg tattacagtg acagttgaca gcgacagcta   1740
tcagttgctc aaggcatata tgatgtcaat atctccggtc tggtaagcac aaccatgcag   1800
aatgaagccc gtcgtctgcg tgccgaacgc tggaaagcgg aaaatcagga agggatggct   1860
gaggtcgccc ggtttattga aatgaacggc tcttttgctg acgagaacag gggctggtga   1920
aatgcagttt aaggtttaca cctataaaag agagagccgt tatcgtctgt ttgtggatgt   1980
acagagtgat attattgaca cgcccgggcg acggatggta atcccctgg ccagtgcacg    2040
tctgctgtca gataaagtct cccgtgaact ttacccggtg gtgcatatcg gggatgaaag   2100
ctggcgcatg atgaccaccg atatggccag tgtgccggtc tccgttatcg gggaagaagt   2160
ggctgatctc agccaccgcg aaaatgacat caaaaacgcc attaacctga tgttctgggg  2220
aatataaatg tcaggctccc ttatacacag ccagtctgca ggtcgaccat agtgactgga   2280
tatgttgtgt tttacagtat tatgtagtct gttttttatg caaaatctaa tttaatatat   2340
tgatatttat atcattttac gtttctcgtt cagctttctt gtacaaagtg gtgatcgatt   2400
cgacagatcg cgatcgcaag tgagtagtgt tctggggcgg gggaggacct gcatgagggc   2460
cagaataact gaaatctgtg cttttctgtg tgttgcagca gcatgagcgg aagcggctcc   2520
tttgagggag gggtattcag cccttatctg acggggcgtc tcccctcctg ggcgggagtg   2580
cgtcagaatg tgatgggatc cacggtggac ggccggcccg tgcagcccgc gaactcttca   2640
accctgacct atgcaaccct gagctcttcg tcgttggacg cagctgccgc cgcagctgct   2700
gcatctgccg ccagcgccgt gcgcggaatg ccatgggcg ccggctacta cggcactctg    2760
gtggccaact cgagttccac caataatccc gccagcctga acgaggagaa gctgttgctg   2820
ctgatggccc agctcgaggc cttgacccag cgcctgggcg agctgaccca gcaggtggct   2880
cagctgcagg agcagacgcg ggccgcggtt gccacggtga aatccaaata aaaaatgaat   2940
caataaataa acgagacgg ttgttgattt taacacagag tctgaatctt tatttgattt    3000
ttcgcgcgcg gtaggccctg gaccaccggt ctcgatcatt gagcacccgg tggatctttt   3060
ccaggacccg gtagaggtgg gcttggatgt tgaggtacat gggcatgagc ccgtcccggg   3120
ggtggaggta gctccattgc agggcctcgt gctcgggggt ggtgttgtaa atcacccagt   3180
catagcaggg gcgcagggca tggtgttgca caatatcttt gaggaggaga ctgatggcca   3240
cgggcagccc tttggtgtag gtgtttacaa atctgttgag ctgggaggga tgcatgcggg   3300
gggagatgag gtgcatcttg gcctggatct tgagattggc gatgttaccg cccagatccc   3360
gcctgggggt catgttgtgc aggaccacca gcacggtgta tccggtgcac ttggggaatt   3420
tatcatgcaa cttggaaggg aaggcgtgaa agaatttggc gacgcctttg tgcccgccca   3480
ggttttccat gcactcatcc atgatgatgg cgatgggccc gtgggcggcg gcctgggcaa   3540
agacgtttcg ggggtcggac acatcatagt tgtggtcctg ggtgaggtca tcataggcca   3600
ttttaatgaa tttggggcgg agggtgccgg actgggggac aaaggtaccc tcgatcccgg   3660
gggcgtagtt cccctcacag atctgcatct cccaggcttt gagctcggag ggggggatca   3720
tgtccacctg cggggcgata aagaacacgg tttccggggc gggggagatg agctgggccg   3780
```

```
aaagcaagtt ccggagcagc tgggacttgc cgcagccggt ggggccgtag atgacccga      3840 tgaccggctg caggtggtag ttgagggaga cacagctgcc gtcctcccgg aggagggggg      3900
ccacctcgtt catcatctcg cgcacgtgca tgttctcgcg caccagttcc gccaggaggc      3960 gctctcccc cagggatagg agctcctgga gcgaggcgaa gtttttcagc ggcttgagtc       4020
cgtcggccat gggcattttg gagagggttt gttgcaagag ttccaggcgg tcccagagct      4080
cggtgatgtg ctctacggca tctcgatcca gcagacctcc tcgtttcgcg ggttgggacg      4140
gctgcgggag tagggcacca gacgatgggc gtccagcgca gccagggtcc ggtccttcca      4200
gggtcgcagc gtccgcgtca gggtggtctc cgtcacggtg aagggtgcg cgccgggctg       4260 ggcgcttgcg agggtgcgct tcaggctcat ccggctggtc gaaaaccgct cccgatcggc      4320
gccctgcgcg tcgccaggt agcaattgac catgagttcg tagttgagcg cctcggccgc       4380
gtggcctttg gcgcggagct tacctttgga agtctgcccg caggcgggac agaggaggga     4440
cttgagggcg tagagcttgg gggcgaggaa gacggactcg ggggcgtagg cgtccgcgcc     4500
gcagtgggcg cagacggtct cgcactccac gagccaggtg aggtcgggct ggtcggggtc     4560
aaaaaccagt ttcccgccgt tcttttgat gcgtttctta cctttggtct ccatgagctc       4620
gtgtccccgc tgggtgacaa agaggctgtc cgtgtccccg tagaccgact ttatgggccg     4680
gtcctcgagc ggtgtgccgc ggtcctcctc gtagaggaac cccgcccact ccgagacgaa     4740
agcccgggtc caggccagca cgaaggaggc cacgtgggac gggtagcggt cgttgtccac     4800
cagcgggtcc acctttcca gggtatgcaa acacatgtcc ccctcgtcca catccaggaa      4860
ggtgattggc ttgtaagtgt aggccacgtg accggggtc ccggccgggg gggtataaaa       4920
gggtgcgggt ccctgctcgt cctcactgtc ttccggatcg ctgtccagga gcgccagctg     4980
ttggggtagg tattccctct cgaaggcggg catgacctcg gcactcaggt tgtcagtttc      5040
tagaaacgag gaggatttga tattgacggt gccggcggag atgcctttca agagcccctc     5100
gtccatctgg tcagaaaaga cgatctttt gttgtcgagc ttggtggcga aggagccgta      5160
gagggcgttg gagaggagct tggcgatgga gcgcatggtc tggttttttt ccttgtcggc     5220
gcgctccttg gcggcgatgt tgagctgcac gtactcgcgc gccacgcact tccattcggg    5280
gaagacggtg gtcagctcgt cgggcacgat tctgacctgc cagccccgat tatgcagggt     5340
gatgaggtcc acactggtgg ccacctcgcc gcgcagggc tcattagtcc agcagaggcg     5400
tccgcccttg cgcgagcaga agggggcag ggggtccagc atgacctcgt cgggggggtc       5460
ggcatcgatg tgaagatgc cgggcaggag gtcggggtca agtagctga tggaagtggc        5520 cagatcgtcc agggcagctt gccattcgcg cacggccagc gcgcgctcgt agggactgag     5580
gggcgtgccc cagggcatgg gatgggtaag cgcggaggcg tacatgccgc agatgtcgta     5640
gacgtagagg ggctcctcga ggatgccgat gtaggtgggg tagcagcgcc cccgcggat     5700 gctggcgcgc acgtagtcat acagctcgtg cgaggggcg aggagccccg gcccaggtt       5760 ggtgcgactg ggcttttcgg cgcggtagac gatctggcgg aaaatggcat gcgagttgga    5820
ggagatggtg ggcctttgga agatgttgaa gtgggcgtgg ggcagtccga ccgagtcgcg     5880
gatgaagtgg gcgtaggagt cttgcagctt ggcgacgagc tcggcggtga ctaggacgtc     5940
cagagcgcag tagtcgaggg tctcctggat gatgtcatac ttgagctgtc ccttttgttt     6000
ccacagctcg cggttgagaa ggaactcttc gcggtcttc cagtactctt cgagggggaa       6060
cccgtcctga tctgcacggt aagagcctag catgtagaac tggttgacgg ccttgtaggc     6120
```

```
gcagcagccc ttctccacgg ggagggcgta ggcctgggcg gccttgcgca gggaggtgtg    6180
cgtgagggcg aaagtgtccc tgaccatgac cttgaggaac tggtgcttga agtcgatatc    6240
gtcgcagccc ccctgctccc agagctggaa gtccgtgcgc ttcttgtagg cggggttggg    6300
caaagcgaaa gtaacatcgt tgaagaggat cttgcccgcg cggggcataa agttgcgagt    6360
gatgcggaaa ggttggggca cctcggcccg gttgttgatg acctgggcgg cgagcacgat    6420
ctcgtcgaag ccgttgatgt tgtggcccac gatgtagagt tccacgaatc gcggacggcc    6480
cttgacgtgg ggcagtttct tgagctcctc gtaggtgagc tcgtcggggt cgctgagccc    6540
gtgctgctcg agcgcccagt cggcgagatg ggggttggcg cggaggaagg aagtccagag    6600
atccacggcc agggcggttt gcagacggtc ccggtactga cggaactgct gcccgacggc    6660
cattttttcg ggggtgacgc agtagaaggt gcggggtcc ccgtgccagc gatcccattt    6720
gagctggagg gcgagatcga gggcgagctc gacgagccgg tcgtccccgg agagtttcat    6780
gaccagcatg aaggggacga gctgcttgcc gaaggacccc atccaggtgt aggtttccac    6840
atcgtaggtg aggaagagcc tttcggtgcg aggatgcgag ccgatgggga agaactggat    6900
ctcctgccac caattggagg aatggctgtt gatgtgatgg aagtagaaat gccgacggcg    6960
cgccgaacac tcgtgcttgt gtttatacaa gcggccacag tgctcgcaac gctgcacggg    7020
atgcacgtgc tgcacgagct gtacctgagt tcctttgacg aggaatttca gtgggaagtg    7080
gagtcgtggc gcctgcatct cgtgctgtac tacgtcgtgg tggtcggcct ggccctcttc    7140
tgcctcgatg gtggtcatgc tgacgagccc gcgcgggagg caggtccaga cctcggcgcg    7200
agcgggtcgg agagcgagga cgagggcgcg caggccggag ctgtccaggg tcctgagacg    7260
ctgcggagtc aggtcagtgg gcagcggcgg cgcgcggttg acttgcagga gttttttccag    7320
ggcgcgcggg aggtccagat ggtacttgat ctccaccgcg ccattggtgg cgacgtcgat    7380
ggcttgcagg gtcccgtgcc cctggggtgt gaccaccgtc ccccgtttct tcttgggcgg    7440
ctggggcgac gggggcggtg cctcttccat ggttagaagc ggcggcgagg acgcgcgccg    7500
ggcggcaggg gcggctcggg gcccggaggc aggggcggca ggggcacgtc ggcgccgcgc    7560
gcgggtaggt tctggtactg cgcccggaga agactggcgt gagcgacgac gcgacgttg     7620
acgtcctgga tctgacgcct ctgggtgaag gccacgggac ccgtgagttt gaacctgaaa    7680
gagagttcga cagaatcaat ctcggtatcg ttgacggcgg cctgccgcag gatctcttgc    7740
acgtcgcccg agttgtcctg gtaggcgatc tcggtcatga actgctcgat ctcctcctct    7800
tgaaggtctc cgcggccggc gcgctccacg gtgccgcgca ggtcgttgga gatgcggccc    7860
atgagctgcg agaaggcgtt catgcccgcc tcgttccaga cgcggctgta gaccacgacg    7920
ccctcgggat cgccggcgcg catgaccacc tgggcgaggt tgagctccac gtggcgcgtg    7980
aagaccgcgt agttgcagag gcgctggtag aggtagttga gcgtggtggc gatgtgctcg    8040
gtgacgaaga aatacatgat ccagcggcgg agcggcatct cgctgacgtc gcccagcgcc    8100
tccaaacgtt ccatggcctc gtaaaagtcc acggcgaagt tgaaaaactg ggagttgcgc    8160
gccgagacgg tcaactcctc ctccagaaga cggatgagct cggcgatggt ggcgcgcacc    8220
tcgcgctcga aggcccccgg gagttcctcc acttcctctt cttcctcctc cactaacatc    8280
tcttctactt cctcctcagg cggcagtggt ggcggggag ggggcctgcg tcgccggcgg    8340
cgcacgggca gacggtcgat gaagcgctcg atggtctcgc cgcgccgcg tcgcatggtc    8400
tcggtgacgg cgcgccgtc ctcgcggggc cgcagcgtga agacgccgcc gcgcatctcc    8460
aggtggccgg gggggtcccc gttgggcagg gagagggcgc tgacgatgca tcttatcaat    8520
```

```
tgccccgtag ggactccgcg caaggacctg agcgtctcga gatccacggg atctgaaaac   8580
cgctgaacga aggcttcgag ccagtcgcag tcgcaaggta ggctgagcac ggtttcttct   8640
ggcgggtcat gttggttggg agcggggcgg gcgatgctgc tggtgatgaa gttgaaatag   8700
gcggttctga gacggcggat ggtggcgagg agcaccaggt ctttgggccc ggcttgctgg   8760
atgcgcagac ggtcggccat gccccaggcg tggtcctgac acctggccag gtccttgtag   8820
tagtcctgca tgagccgctc cacgggcacc tcctcctcgc ccgcgcgcc gtgcatgcgc    8880 gtgagcccga agccgcgctg gggctggacg agcgccaggt cggcgacgac gcgctcggcg   8940
aggatggctt gctggatctg ggtgagggtg gtctggaagt catcaaagtc gacgaagcgg   9000
tggtaggctc cggtgttgat ggtgtaggag cagttggcca tgacggacca gttgacggtc   9060
tggtggcccg gacgcacgag ctcgtggtac ttgaggcgcg agtaggcgcg cgtgtcgaag   9120
atgtagtcgt tgcaggtgcg caccaggtac tggtagccga tgaggaagtg cggcggcggc   9180
tggcggtaga gcggccatcg ctcggtggcg ggggcgccgg gcgcgaggtc ctcgagcatg   9240
gtgcggtggt agccgtagat gtacctggac atccaggtga tgccggcggc ggtggtggag   9300
gcgcgcggga actcgcggac gcggttccag atgttgcgca gcggcaggaa gtagttcatg   9360
gtgggcacgg tctggcccgt gaggcgcgcg cagtcgtgga tgctctatac gggcaaaaac   9420
gaaagcggtc agcggctcga ctccgtggcc tggaggctaa gcaacgggt tgggctgcgc    9480 gtgtaccccg gttcgaatct cgaatcaggc tggagccgca gctaacgtgg tattggcact   9540
cccgtctcga cccaagcctg caccaaccct ccaggatacg gaggcgggtc gttttgcaac   9600 tttttttttgg aggccggatg agactagtaa gcgcggaaag cggccgaccg cgatggctcg   9660
ctgccgtagt ctggagaaga atcgccaggg ttgcgttgcg gtgtgccccg gttcgaggcc   9720
ggccggattc cgcggctaac gagggcgtgg ctgccccgtc gtttccaaga ccccatagcc   9780
agccgacttc tccagttacg gagcgagccc ctcttttgtt ttgtttgttt ttgccagatg   9840
catcccgtac tgcggcagat gcgcccccac caccctccac cgcaacaaca gccccctcca   9900
cagccggcgc ttctgccccc gccccagcag caacttccag ccacgaccgc gcggccgcc    9960 gtgagcgggg ctgacagag ttatgatcac cagctggcct tggaagaggg cgaggggctg    10020
gcgcgcctgg gggcgtcgtc gccggagcgg caccccgcgcg tgcagatgaa aagggacgct   10080
cgcgaggcct acgtgcccaa gcagaacctg ttcagagaca ggagcggcga ggagcccgag   10140
gagatgcgcg cggcccggtt ccacgcgggg cgggagctgc ggcgcggcct ggaccgaaag   10200
agggtgctga gggacgagga tttcgaggcg gacgagctga cggggatcag ccccgcgcgc   10260
gcgcacgtgg ccgcggccaa cctggtcacg gcgtacgagc agaccgtgaa ggaggagagc   10320
aacttccaaa aatccttcaa caaccacgtg cgcaccctga tcgcgcgcga ggaggtgacc   10380
ctgggcctga tgcacctgtg ggacctgctg gaggccatcg tgcagaaccc caccagcaag   10440
ccgctgacgg cgcagctgtt cctggtggtg cagcatagtc gggacaacga agcgttcagg   10500
gaggcgctgc tgaatatcac cgagcccgag ggccgctggc tcctggacct ggtgaacatt   10560
ctgcagagca tcgtggtgca ggagcgcggg ctgccgctgt ccgagaagct ggcggccatc   10620
aacttctcgg tgctgagttt gggcaagtac tacgctagga agatctacaa gaccccgtac   10680
gtgcccatag acaaggaggt gaagatcgac gggttttaca tgcgcatgac cctgaaagtg   10740
ctgaccctga gcgacgatct gggggtgtac cgcaacgaca ggatgcaccg tgcggtgagc   10800
gccagcaggc ggcgcgagct gagcgaccag gagctgatgc atagtctgca gcgggccctg   10860
```

| | | | | | |
|---|---|---|---|---|---|
| accggggccg | ggaccgaggg | ggagagctac | tttgacatgg | gcgcggacct | gcactggcag | 10920 |
| cccagccgcc | gggccttgga | ggcggcggca | ggaccctacg | tagaagaggt | ggacgatgag | 10980 |
| gtggacgagg | agggcgagta | cctggaagac | tgatggcgcg | accgtatttt | tgctagatgc | 11040 |
| aacaacaaca | gccacctcct | gatcccgcga | tgcgggcggc | gctgcagagc | cagccgtccg | 11100 |
| gcattaactc | ctcggacgat | tggacccagg | ccatgcaacg | catcatggcg | ctgacgaccc | 11160 |
| gcaaccccga | agcctttaga | cagcagcccc | aggccaaccg | gctctcggcc | atcctggagg | 11220 |
| ccgtggtgcc | ctcgcgctcc | aaccccacgc | acgagaaggt | cctggccatc | gtgaacgcgc | 11280 |
| tggtggagaa | caaggccatc | cgcggcgacg | aggccggcct | ggtgtacaac | gcgctgctgg | 11340 |
| agcgcgtggc | ccgctacaac | agcaccaacg | tgcagaccaa | cctggaccgc | atggtgaccg | 11400 |
| acgtgcgcga | ggccgtggcc | cagcgcgagc | ggttccaccg | cgagtccaac | ctgggatcca | 11460 |
| tggtggcgct | gaacgccttc | ctcagcaccc | agcccgccaa | cgtgccccgg | ggccaggagg | 11520 |
| actacaccaa | cttcatcagc | gccctgcgcc | tgatggtgac | cgaggtgccc | cagagcgagg | 11580 |
| tgtaccagtc | cgggccggac | tacttcttcc | agaccagtcg | ccaggccttg | cagaccgtga | 11640 |
| acctgagcca | ggctttcaag | aacttgcagg | gcctgtgggg | cgtgcaggcc | ccggtcgggg | 11700 |
| accgcgcgac | ggtgtcgagc | ctgctgacgc | cgaactcgcg | cctgctgctg | ctgctggtgg | 11760 |
| cccccttcac | ggacagcggc | agcatcaacc | gcaactcgta | cctgggctac | ctgattaacc | 11820 |
| tgtaccgcga | ggccatcggc | caggcgcacg | tggacgagca | gacctaccag | gagatcaccc | 11880 |
| acgtgagccg | cgccctgggc | caggacgacc | cgggcaacct | ggaagccacc | ctgaactttt | 11940 |
| tgctgaccaa | ccggtcgcag | aagatcccgc | cccagtacgc | gctcagcacc | gaggaggagc | 12000 |
| gcatcctgcg | ttacgtgcag | cagagcgtgg | gcctgttcct | gatgcaggag | ggggccaccc | 12060 |
| ccagcgccgc | gctcgacatg | accgcgcgca | acatggagcc | cagcatgtac | gccagcaacc | 12120 |
| gcccgttcat | caataaactg | atggactact | tgcatcgggc | ggccgccatg | aactctgact | 12180 |
| atttcaccaa | cgccatcctg | aatccccact | ggctcccgcc | gccggggttc | tacacgggcg | 12240 |
| agtacgacat | gcccgacccc | aatgacgggt | tcctgtggga | cgatgtggac | agcagcgtgt | 12300 |
| tctcccccccg | accgggtgct | aacgagcgcc | ccttgtggaa | gaaggaaggc | agcgaccgac | 12360 |
| gcccgtcctc | ggcgctgtcc | ggcgcgagg | gtgctgccgc | ggcggtgccc | gaggccgcca | 12420 |
| gtcctttccc | gagcttgccc | ttctcgctga | acagtatccg | cagcagcgag | ctgggcagga | 12480 |
| tcacgcgccc | gcgcttgctg | ggcgaagagg | agtacttgaa | tgactcgctg | ttgagacccg | 12540 |
| agcgggagaa | gaacttcccc | aataacggga | tagaaagcct | ggtggacaag | atgagccgct | 12600 |
| ggaagacgta | tgcgcaggag | cacagggacg | atccccgggc | gtcgcagggg | gccacgagcc | 12660 |
| ggggcagcgc | cgcccgtaaa | cgccggtggc | acgacaggca | gcgggacag | atgtgggacg | 12720 |
| atgaggactc | cgccgacgac | agcagcgtgt | tggacttggg | tgggagtggt | aacccgttcg | 12780 |
| ctcacctgcg | cccccgtatc | gggcgcatga | tgtaagagaa | accgaaaata | aatgatactc | 12840 |
| accaaggcca | tggcgaccag | cgtgcgttcg | tttcttctct | gttgttgttg | tatctagtat | 12900 |
| gatgaggcgt | gcgtacccgg | agggtcctcc | tccctcgtac | gagagcgtga | tgcagcaggc | 12960 |
| gatgcggcg | gcgcgatgc | agccccgct | ggaggctcct | tacgtgcccc | gcggtacct | 13020 |
| ggcgcctacg | gaggggcgga | acagcattcg | ttactcggag | ctggcacccct | tgtacgatac | 13080 |
| cacccggttg | tacctggtgg | acaacaagtc | ggcggacatc | gcctcgctga | actaccagaa | 13140 |
| cgaccacagc | aacttcctga | ccaccgtggt | gcagaacaat | gacttcaccc | ccacggaggc | 13200 |
| cagcacccag | accatcaact | ttgacgagcg | ctcgcggtgg | ggcggccagc | tgaaaaccat | 13260 |

```
catgcacacc aacatgccca acgtgaacga gttcatgtac agcaacaagt tcaaggcgcg    13320
ggtgatggtc tcccgcaaga cccccaatgg ggtgacagtg acagaggatt atgatggtag    13380
tcaggatgag ctgaagtatg aatgggtgga atttgagctg cccgaaggca acttctcggt    13440
gaccatgacc atcgacctga tgaacaacgc catcatcgac aattacttgg cggtggggcg    13500
gcagaacggg gtgctggaga gcgacatcgg cgtgaagttc gacactagga acttcaggct    13560
gggctgggac cccgtgaccg agctggtcat gcccggggtg tacaccaacg aggctttcca    13620
tcccgatatt gtcttgctgc ccggctgcgg ggtggacttc accgagagcc gcctcagcaa    13680
cctgctgggc attcgcaaga ggcagccctt ccaggaaggc ttccagatca tgtacgagga    13740
tctggagggg ggcaacatcc ccgcgctcct ggatgtcgac gcctatgaga aagcaagga    13800 ggatgcagca gctgaagcaa ctgcagccgt agctaccgcc tctaccgagg tcaggggcga    13860
taattttgca agcgccgcag cagtggcagc ggccgaggcg gctgaaaccg aaagtaagat    13920
agtcattcag ccggtggaga aggatagcaa gaacaggagc tacaacgtac taccggacaa    13980
gataaacacc gcctaccgca gctggtacct agcctacaac tatggcgacc ccgagaaggg    14040
cgtgcgctcc tggacgctgc tcaccacctc ggacgtcacc tgcggcgtgg agcaagtcta    14100
ctggtcgctg cccgacatga tgcaagaccc ggtcaccttc cgctccacgc gtcaagttag    14160
caactacccg gtggtgggcg ccgagctcct gcccgtctac tccaagagct tcttcaacga    14220
gcaggccgtc tactcgcagc agctgcgcgc cttcacctcg cttacgcacg tcttcaaccg    14280
cttccccgag aaccagatcc tcgtccgccc gccgcgcccc accattacca ccgtcagtga    14340
aaacgttcct gctctcacag atcacgggac cctgccgctg cgcagcagta tccggggagt    14400
ccagcgcgtg accgttactg acgccagacg ccgcacctgc ccctacgtct acaaggccct    14460
gggcatagtc gcgccgcgcg tcctctcgag ccgcaccttc taaatgtcca ttctcatctc    14520
gcccagtaat aacaccggtt ggggcctgcg cgcgcccagc aagatgtacg gaggcgctcg    14580
ccaacgctcc acgcaacacc ccgtgcgcgt gcgcgggcac ttccgcgctc cctggggcgc    14640
cctcaagggc cgcgtgcggt cgcgcaccac cgtcgacgac gtgatcgacc aggtggtggc    14700
cgacgcgcgc aactacaccc ccgccgccgc gcccgtctcc accgtggacg ccgtcatcga    14760
cagcgtggtg gcggacgcgc gccggtacgc ccgcgccaag agccggcggc ggcgcatcgc    14820
ccggcggcac cggagcaccc ccgccatgcg cgcggcgcga gccttgctgc gcagggccag    14880
gcgcacggga cgcagggcca tgctcagggc ggccagacgc gcggcttcag gcgccagcgc    14940
cggcaggacc cggagacgcg cggccacggc ggcgcagcg gccatcgcca gcatgtcccg    15000
cccgcggcga gggaacgtgt actgggtgcg cgacgccgcc accggtgtgc gcgtgcccgt    15060
gcgcacccgc cccctcgca cttgaagatg ttcacttcgc gatgttgatg tgtcccagcg    15120
gcgaggagga tgtccaagcg caaattcaag gaagagatgc tccaggtcat cgcgcctgag    15180
atctacggcc ctgcggtggt gaaggaggaa agaaagcccc gcaaaatcaa gcgggtcaaa    15240
aaggacaaaa aggaagaaga aagtgatgtg gacggattgg tggagtttgt gcgcgagttc    15300 gcccccggc ggcgcgtgca gtggcgcggg cggaaggtgc aaccggtgct gagacccggc    15360
accaccgtgg tcttcacgcc cggcgagcgc tccggcaccc cttccaagcg ctcctacgac    15420
gaggtgtacg gggatgatga tattctggag caggcggccg agcgcctggg cgagtttgct    15480
tacggcaagc gcagccgttc cgcaccgaag gaagaggcgg tgtccatccc gctgaccac    15540 ggcaaccccca cgccgagcct caagcccgtg accttgcagc aggtgctgcc gaccgcggcg    15600
```

```
ccgcgccggg ggttcaagcg cgagggcgag gatctgtacc ccaccatgca gctgatggtg   15660
cccaagcgcc agaagctgga agacgtgctg gagaccatga aggtggaccc ggacgtgcag   15720
cccgaggtca aggtgcggcc catcaagcag gtggcccggg gcctgggcgt gcagaccgtg   15780
gacatcaaga ttcccacgga gcccatggaa acgcagaccg agcccatgat caagcccagc   15840
accagcacca tggaggtgca gacggatccc tggatgccat cggctcctag tcgaagaccc   15900
cggcgcaagt acgqcgcggc cagcctgctg atgcccaact acgcgctgca tccttccatc   15960
atccccacgc cgggctaccg cggcacgcgc ttctaccgcg gtcataccag cagccgccgc   16020
cgcaagacca ccactcgccg ccgccgtcgc cgcaccgccg ctgcaaccac ccctgccgcc   16080
ctggtgcgga gagtgtaccg ccgcggccgc gcacctctga ccctgccgcg cgcgcgctac   16140
cacccgagca tcgccattta aactttcgcc agctttgcag atcaatggcc ctcacatgcc   16200
gccttcgcgt tcccattacg ggctaccgag gaagaaaacc gcgccgtaga aggctggcgg   16260
ggaacgggat gcgtcgccac caccaccggc ggcggcgcgc catcagcaag cggttggggg   16320
gaggcttcct gcccgcgctg atccccatca tcgccgcggc gatcggggcg atccccggca   16380
ttgcttccgt ggcggtgcag gcctctcagc gccactgaga cacacttgga aacatcttgt   16440
aataaaccca tggactctga cgctcctggt cctgtgatgt gttttcgtag acagatggaa   16500
gacatcaatt tttcgtccct ggctccgcga cacggcacgc ggccgttcat gggcacctgg   16560
agcgacatcg gcaccagcca actgaacggg ggcgccttca attggagcag tctctggagc   16620
gggcttaaga atttcgggtc cacgcttaaa acctatggca gcaaggcgtg gaacagcacc   16680
acagggcagg cgctgaggga taagctgaaa gagcagaact tccagcagaa ggtggtcgat   16740
gggctcgcct cgggcatcaa cggggtggtg gacctggcca accaggccgt gcagcggcag   16800
atcaacagcc gcctggaccc ggtgccgccc gccggctccg tggagatgcc gcaggtggag   16860
gaggagctgc ctcccctgga caagcggggc gagaagcgac cccgccccga tgcggaggag   16920
acgctgctga cgcacacgga cgagccgccc cgtacgaggg aggcggtgaa actgggtctg   16980
cccaccacgc ggcccatcgc gcccctggcc accggggtgc tgaaacccga aaagcccgcg   17040
accctggact gcctcctcc ccagccttcc cgccctcta cagtggctaa gcccctgccg   17100
ccggtggccg tggcccgcgc gcgacccggg ggcaccgccc gccctcatgc gaactggcag   17160
agcactctga acagcatcgt gggtctggga gtgcagagtg tgaagcgccg ccgctgctat   17220
taaacctacc gtagcgctta acttgcttgt ctgtgtgtgt atgtattatg tcgccgccgc   17280
cgctgtccac cagaaggagg agtgaagagg cgcgtcgccg agttgcaaga tggccacccc   17340
atcgatgctg ccccagtggg cgtacatgca catcgccgga caggacgctt cggagtacct   17400
gagtccgggt ctggtgcagt ttgcccgcgc cacagacacc tacttcagtc tggggaacaa   17460
gtttaggaac cccacggtgg cgcccacgca cgatgtgacc accgaccgca gccagcggct   17520
gacgctgcgc ttcgtgcccg tggaccgcga ggacaacacc tactcgtaca agtgcgccta   17580
cacgctggcc gtgggcgaca accgcgtgct ggacatggcc agcacctact ttgacatccg   17640
cggcgtgctg gatcggggcc ctagcttcaa accctactcc ggcaccgcct acaacagtct   17700
ggcccccaag ggagcaccca acacttgtca gtggacatat aaagccgatg gtgaaactgc   17760
cacagaaaaa acctatacat atggaaatgc acccgtgcag ggcattaaca tcacaaaaga   17820
tggtattcaa cttggaactg acaccgatga tcagccaatc tacgcagata aacctatca   17880 gcctgaacct caagtgggtg atgctgaatg gcatgacatc actggtactg atgaaaagta   17940
tggaggcaga gctcttaagc ctgataccaa aatgaagcct tgttatggtt cttttgccaa   18000
```

```
gcctactaat aaagaaggag gtcaggcaaa tgtgaaaaca ggaacaggca ctactaaaga    18060
atatgacata gacatggctt tctttgacaa cagaagtgcg gctgctgctg gcctagctcc    18120
agaaattgtt ttgtatactg aaaatgtgga tttggaaact ccagatacc atattgtata    18180 caaagcaggc acagatgaca gcagctcttc tattaatttg ggtcagcaag ccatgcccaa    18240
cagacctaac tacattggtt tcagagacaa ctttatcggg ctcatgtact acaacagcac    18300
tggcaatatg ggggtgctgg ccggtcaggc ttctcagctg aatgctgtgg ttgacttgca    18360
agacagaaac accgagctgt cctaccagct cttgcttgac tctctgggtg acagaacccg    18420
gtatttcagt atgtggaatc aggcggtgga cagctatgat cctgatgtgc gcattattga    18480
aaatcatggt gtggaggatg aacttcccaa ctattgtttc cctctggatg ctgttggcag    18540
aacagatact tatcagggaa ttaaggctaa tggaactgat caaaccacat ggaccaaaga    18600
tgacagtgtc aatgatgcta atgagatagg caagggtaat ccattcgcca tggaaatcaa    18660
catccaagcc aacctgtgga ggaacttcct ctacgccaac gtggccctgt acctgcccga    18720
ctcttacaag tacacgccgg ccaatgttac cctgcccacc aacaccaaca cctacgatta    18780
catgaacggc cgggtggtgg cgccctcgct ggtggactcc tacatcaaca tcggggcgcg    18840
ctggtcgctg gatcccatgg acaacgtgaa ccccttcaac caccaccgca atgcggggct    18900
gcgctaccgc tccatgctcc tgggcaacgg gcgctacgtg cccttccaca tccaggtgcc    18960
ccagaaattt ttcgccatca agagcctcct gctcctgccc gggtcctaca cctacgagtg    19020
gaacttccgc aaggacgtca acatgatcct gcagagctcc ctcggcaacg acctgcgcac    19080
ggacggggcc tccatctcct tcaccagcat caacctctac gccaccttct tccccatggc    19140
gcacaacacg gcctccacgc tcgaggccat gctgcgcaac gacaccaacg accagtcctt    19200
caacgactac ctctcggcgg ccaacatgct ctaccccatc ccggccaacg ccaccaacgt    19260
gcccatctcc atccctcgc gcaactgggc cgccttccgc ggctggtcct tcacgcgtct    19320
caagaccaag gagacgccct cgctgggctc cgggttcgac ccctacttcg tctactcggg    19380
ctccatcccc tacctcgacg gcaccttcta cctcaaccac accttcaaga aggtctccat    19440
caccttcgac tcctccgtca gctggccgg caacgaccgg ctcctgacgc ccaacgagtt    19500
cgaaatcaag cgcaccgtcg acggcgaggg ctacaacgtg gcccagtgca acatgaccaa    19560
ggactggttc ctggtccaga tgctggccca ctacaacatc ggctaccagg gcttctacgt    19620
gcccgagggc tacaaggacc gcatgtactc cttcttccgc aacttccagc ccatgagccg    19680
ccaggtggtg gacgaggtca actacaagga ctaccaggcc gtcaccctgg cctaccagca    19740
caacaactcg ggcttcgtcg gctacctcgc gccaccatg cgccagggcc agccctaccc    19800
cgccaactac ccctacccgc tcatcggcaa gagcgccgtc accagcgtca cccagaaaaa    19860
gttcctctgc gacagggtca tgtggcgcat ccccttctcc agcaacttca tgtccatggg    19920
cgcgctcacc gacctcggcc agaacatgct ctatgccaac tccgcccacg cgctagacat    19980
gaatttcgaa gtcgacccca tggatgagtc caccttctc tatgttgtct tcgaagtctt    20040
cgacgtcgtc cgagtgcacc agccccaccg cggcgtcatc gaggccgtct acctgcgcac    20100 cccttctcg gccggtaacg ccaccaccta agctcttgct tcttgcaagc catgccgcg    20160 ggctccggcg agcaggagct cagggccatc atccgcgacc tgggctgcgg gccctacttc    20220
ctgggcacct tcgataagcg cttcccggga ttcatggccc cgcacaagct ggcctgcgcc    20280
atcgtcaaca cggccggccg cgagaccggg ggcgagcact ggctggcctt cgcctggaac    20340
```

```
ccgcgctcga acacctgcta cctcttcgac cccttcgggt tctcggacga gcgcctcaag    20400
cagatctacc agttcgagta cgagggcctg ctgcgccgca gcgccctggc caccgaggac    20460
cgctgcgtca ccctggaaaa gtccacccag accgtgcagg gtccgcgctc ggccgcctgc    20520
gggctcttct gctgcatgtt cctgcacgcc ttcgtgcact ggcccgaccg ccccatggac    20580
aagaacccca ccatgaactt gctgacgggg gtgcccaacg gcatgctcca gtcgcccag    20640 gtggaaccca ccctgcgccg caaccaggag gcgctctacc gcttcctcaa ctcccactcc    20700
gcctactttc gctcccaccg cgcgcgcatc gagaaggcca ccgccttcga ccgcatgaat    20760
caagacatgt aaaccgtgtg tgtatgttaa atgtctttaa taaacagcac tttcatgtta    20820
cacatgcatc tgagatgatt tatttagaaa tcgaagggt tctgccgggt ctcggcatgg    20880
cccgcgggca gggacacgtt gcggaactgg tacttggcca gccacttgaa ctcggggatc    20940
agcagtttgg gcagcggggt gtcggggaag gagtcggtcc acagcttccg cgtcagttgc    21000
agggcgccca gcaggtcggg cgcggagatc ttgaaatcgc agttgggacc cgcgttctgc    21060
gcgcgggagt tgcggtacac gggggttgcag cactggaaca ccatcagggc cgggtgcttc    21120
acgctcgcca gcaccgtcgc gtcggtgatg ctctccacgt cgaggtcctc ggcgttggcc    21180
atcccgaagg gggtcatctt gcaggtctgc cttcccatgg tgggcacgca cccgggcttg    21240
tggttgcaat cgcagtgcag ggggatcagc atcatctggg cctggtcggc gttcatcccc    21300
gggtacatgg ccttcatgaa agcctccaat tgcctgaacg cctgctgggc cttggctccc    21360
tcggtgaaga agaccccgca ggacttgcta gagaactggt tggtggcgca cccggcgtcg    21420
tgcacgcagc agcgcgcgtc gttgttggcc agctgcacca cgctgcgccc ccagcggttc    21480
tgggtgatct tggcccggtc ggggttctcc ttcagcgcgc gctgcccgtt ctcgctcgcc    21540
acatccatct cgatcatgtg ctccttctgg atcatggtgg tcccgtgcag gcaccgcagc    21600
ttgccctcgg cctcggtgca cccgtgcagc cacagcgcgc acccggtgca ctcccagttc    21660
ttgtgggcga tctgggaatg cgcgtgcacg aagccctgca ggaagcggcc catcatggtg    21720
gtcagggtct tgttgctagt gaaggtcagc ggaatgccgc ggtgctcctc gttgatgtac    21780
aggtggcaga tgcggcggta cacctcgccc tgctcgggca tcagctggaa gttggctttc    21840
aggtcggtct ccacgcggta gcggtccatc agcatagtca tgatttccat acccttctcc    21900
caggccgaga cgatgggcag gctcataggg ttcttcacca tcatcttagc gctagcagcc    21960
gcggccaggg ggtcgctctc gtccagggtc tcaaagctcc gcttgccgtc cttctcggtg    22020
atccgcaccg gggggtagct gaagcccacg gccgccagct cctcctcggc ctgtctttcg    22080
tcctcgctgt cctggctgac gtcctgcagg accacatgct tggtcttgcg gggtttcttc    22140
ttgggcggca gcgcggcgg agatgttgga gatggcgagg gggagcgcga gttctcgctc    22200
accactacta tctcttcctc ttcttggtcc gaggccacgc ggcggtaggt atgtctcttc    22260
gggggcagag gcggaggcga cgggctctcg ccgccgcgac ttggcggatg gctggcagag    22320 cccccttccgc gttcgggggt gcgctcccgg cggcgctctg actgacttcc tccgcggccg    22380
gccattgtgt tctcctaggg aggaacaaca agcatggaga ctcagccatc gccaacctcg    22440
ccatctgccc ccaccgccga cgagaagcag cagcagcaga atgaaagctt aaccgccccg    22500
ccgcccagcc ccgccaccct cgacgcggcc gtcccagaca tgcaagagat ggaggaatcc    22560
atcgagattg acctgggcta tgtgacgccc gcggagcacg aggaggagct ggcagtgcgc    22620
ttttcacaag aagagataca ccaagaacag ccagagcagg aagcagagaa tgagcagagt    22680
caggctgggc tcgagcatga cggcgactac ctccacctga gcgggggga ggacgcgctc    22740
```

```
atcaagcatc tggcccggca ggccaccatc gtcaaggatg cgctgctcga ccgcaccgag    22800
gtgcccctca gcgtggagga gctcagccgc gcctacgagt tgaacctctt ctcgccgcgc    22860
gtgcccccca agcgccagcc caatggcacc tgcgagccca acccgcgcct caacttctac    22920
ccggtcttcg cggtgcccga ggccctggcc acctaccaca tcttttttcaa gaaccaaaag   22980 atccccgtct cctgccgcgc caaccgcacc cgcgccgacg ccctttttcaa cctgggtccc   23040 ggcgcccgcc tacctgatat cgcctccttg gaagaggttc ccaagatctt cgagggtctg    23100
ggcagcgacg agactcgggc cgcgaacgct ctgcaaggag aaggaggaga gcatgagcac    23160
cacagcgccc tggtcgagtt ggaaggcgac aacgcgcggc tggcggtgct caaacgcacg    23220
gtcgagctga cccatttcgc ctacccggct ctgaacctgc cccccaaagt catgagcgcg    23280
gtcatggacc aggtgctcat caagcgcgcg tcgcccatct ccgaggacga gggcatgcaa    23340
gactccgagg agggcaagcc cgtggtcagc gacgagcagc tggcccggtg gctgggtcct    23400
aatgctagtc cccagagttt ggaagagcgg cgcaaactca tgatggccgt ggtcctggtg    23460
accgtggagc tggagtgcct gcgccgcttc ttcgccgacg cggagaccct gcgcaaggtc    23520
gaggagaacc tgcactacct cttcaggcac gggttcgtgc gccaggcctg caagatctcc    23580
aacgtggagc tgaccaacct ggtctcctac atgggcatct tgcacgagaa ccgcctgggg    23640
cagaacgtgc tgcacaccac cctgcgcggg gaggcccggc gcgactacat ccgcgactgc    23700
gtctacctct acctctgcca cacctggcag acgggcatgg gcgtgtggca gcagtgtctg    23760
gaggagcaga acctgaaaga gctctgcaag ctcctgcaga agaacctcaa gggtctgtgg    23820
accgggttcg acgagcgcac caccgcctcg gacctggccg acctcatttt ccccgagcgc    23880
ctcaggctga cgctgcgcaa cggcctgccc gactttatga gccaaagcat gttgcaaaac    23940
tttcgctctt tcatcctcga acgctccgga atcctgcccg ccacctgctc cgcgctgccc    24000
tcggacttcg tgccgctgac cttcgcgag tgccccccgc cgctgtggag ccactgctac    24060
ctgctgcgcc tggccaacta cctggcctac cactcggacg tgatcgagga cgtcagcggc    24120
gagggcctgc tcgagtgcca ctgccgctgc aacctctgca cgccgcaccg ctccctggcc    24180
tgcaaccccc agctgctgag cgagacccag atcatcggca ccttcgagtt gcaagggccc    24240
agcgaaggcg agggttcagc cgccaagggg ggtctgaaac tcaccccggg gctgtggacc    24300
tcggcctact tgcgcaagtt cgtgcccgag gactaccatc ccttcgagat caggttctac    24360
gaggaccaat cccatccgcc caaggccgag ctgtcggcct gcgtcatcac ccaggggggcg   24420 atcctggccc aattgcaagc catccagaaa tcccgccaag aattcttgct gaaaaagggc    24480 cgcgggggtct acctcgaccc ccagaccggt gaggagctca accccggctt cccccaggat    24540
gccccgagga aacaagaagc tgaaagtgga gctgccgccc gtggaggatt tggaggaaga    24600
ctgggagaac agcagtcagg cagaggagga ggagatggag gaagactggg acagcactca    24660
ggcagaggag gacagcctgc aagacagtct ggaggaagac gaggaggagg cagaggagga    24720
ggtggaagaa gcagccgccg ccagaccgtc gtcctcggcg ggggagaaag caagcagcac    24780
ggataccatc tccgctccgg gtcggggtcc cgctcgacca cacagtagat gggacgagac    24840
cggacgattc ccgaacccca ccacccagac cggtaagaag gagcggcagg gatacaagtc    24900
ctggcggggg cacaaaaacg ccatcgtctc ctgcttgcag gcctgcgggg gcaacatctc    24960
cttcacccgg cgctacctgc tcttccaccg cggggtgaac tttccccgca acatcttgca    25020
ttactaccgt cacctccaca gcccctacta cttccaagaa gaggcagcag cagcagaaaa    25080
```

```
agaccagcag aaaaccagca gctagaaaat ccacagcggc ggcagcaggt ggactgagga    25140
tcgcggcgaa cgagccggcg caaacccggg agctgaggaa ccggatcttt cccaccctct    25200
atgccatctt ccagcagagt cgggggcagg agcaggaact gaaagtcaag aaccgttctc    25260
tgcgctcgct cacccgcagt tgtctgtatc acaagagcga agaccaactt cagcgcactc    25320
tcgaggacgc cgaggctctc ttcaacaagt actgcgcgct cactcttaaa gagtagcccg    25380
cgcccgccca gtcgcagaaa aaggcgggaa ttacgtcacc tgtgcccttc gcccctagccg    25440 cctccaccca tcatcatgag caaagagatt cccacgcctt acatgtggag ctaccagccc    25500
cagatgggcc tggccgccgg tgccgcccag gactactcca cccgcatgaa ttggctcagc    25560
gccgggcccg cgatgatctc acgggtgaat gacatccgcg cccaccgaaa ccagatactc    25620
ctagaacagt cagcgctcac cgccacgccc cgcaatcacc tcaatccgcg taattggccc    25680
gccgccctgg tgtaccagga aattccccag cccacgaccg tactacttcc gcgagacgcc    25740
caggccgaag tccagctgac taactcaggt gtccagctgg cgggcggcgc caccctgtgt    25800
cgtcaccgcc ccgctcaggg tataaagcgg ctggtgatcc ggggcagagg cacacagctc    25860
aacgacgagg tggtgagctc ttcgctgggt ctgcgacctg acggagtctt ccaactcgcc    25920
ggatcgggga gatcttcctt cacgcctcgt caggccgtcc tgactttgga gagttcgtcc    25980
tcgcagcccc gctcgggtgg catcggcact ctccagttcg tggaggagtt cactccctcg    26040
gtctacttca accccttctc cggctccccc ggccactacc cggacgagtt catcccgaac    26100
ttcgacgcca tcagcgagtc ggtggacggc tacgattgag tttaaactca ccccccttatc    26160 cagtgaaata aagatcatat tgatgatgat tttacagaaa taaaaaataa tcatttgatt    26220
tgaaataaag atacaatcat attgatgatt tgagtttaac aaaaaaataa agaatcactt    26280
acttgaaatc tgataccagg tctctgtcca tgttttctgc caacaccact tcactcccct    26340
cttcccagct ctggtactgc aggccccggc gggctgcaaa cttcctccac acgctgaagg    26400
ggatgtcaaa ttcctcctgt ccctcaatct tcattttatc ttctatcaga tgtccaaaaa    26460
gcgcgtccgg gtggatgatg acttcgaccc cgtctacccc tacgatgcag acaacgcacc    26520
gaccgtgccc ttcatcaacc ccccccttcgt ctcttcagat ggattccaag agaagccccct    26580 gggggtgttg tccctgcgac tggccgaccc cgtcaccacc aagaacgggg aaatcaccct    26640
caagctggga gaggggtgg acctcgattc ctcgggaaaa ctcatctcca acacggccac    26700
caaggccgcc gcccctctca gttttttccaa caacaccatt tcccttaaca tggatcaccc    26760
cttttacact aaagatggaa aattatcctt acaagtttct ccaccattaa atatactgag    26820
aacaagcatt ctaaacacac tagctttagg ttttggatca ggtttaggac tccgtggctc    26880
tgccttggca gtcagttag tctctccact tacatttgat actgatgaa acataaagct    26940 taccttagac agaggtttgc atgttacaac aggagatgca attgaaagca acataagctg    27000
ggctaaaggt ttaaaatttg aagatggagc catagcaacc aacattggaa atgggttaga    27060
gtttggaagc agtagtacag aaacaggtgt tgatgatgct tacccaatcc aagttaaact    27120
tggatctggc cttagctttg acagtacagg agccataatg gctggtaaca agaagacga    27180 taaactcact ttgtggacaa cacctgatcc atcaccaaac tgtcaaatac tcgcagaaaa    27240
tgatgcaaaa ctaacacttt gcttgactaa atgtggtagt caaatactgg ccactgtgtc    27300
agtcttagtt gtaggaagtg gaaacctaaa ccccattact ggcaccgtaa gcagtgctca    27360
ggtgttccta cgttttgatg caaacggtgt tcttttaaca gaacattcta cactaaaaaa    27420
atactggggg tataggcagg gagatagcat agatggcact ccatataccca atgctgtagg    27480
```

```
attcatgccc aatttaaaag cttatccaaa gtcacaaagt tctactacta aaaataatat   27540
agtagggcaa gtatacatga atggagatgt ttcaaaacct atgcttctca ctataaccct   27600
caatggtact gatgacagca acagtacata ttcaatgtca ttttcataca cctggactaa   27660
tggaagctat gttggagcaa catttggggc taactcttat accttctcat acatcgccca   27720
agaatgaaca ctgtatccca ccctgcatgc caacccttcc caccccactc tgtggaacaa   27780
actctgaaac acaaaataaa ataaagttca agtgttttat tgattcaaca gtttcacaga   27840
accctagtat tcaacctgcc acctccctcc aacacacag agtacacagt cctttctccc   27900
cggctggcct taaaaagcat catatcatgg gtaacagaca tattcttagg tgttatattc   27960
cacacggttt cctgtcgagc caaacgctca tcagtgatat taataaactc cccgggcagc   28020
tcacttaagt tcatgtcgct gtccagctgc tgagccacag gctgctgtcc aacttgcggt   28080
tgcttaacgg gcggcgaagg agaagtccac gcctacatgg gggtagagtc ataatcgtgc   28140
atcaggatag ggcggtggtg ctgcagcagc gcgcgaataa actgctgccg ccgccgctcc   28200
gtcctgcagg aatacaacat ggcagtggtc tcctcagcga tgattcgcac cgcccgcagc   28260
ataaggcgcc ttgtcctccg ggcacagcag cgcaccctga tctcacttaa atcagcacag   28320
taactgcagc acagcaccac aatattgttc aaaatcccac agtgcaaggc gctgtatcca   28380
aagctcatgg cggggaccac agaacccacg tggccatcat accacaagcg caggtagatt   28440
aagtggcgac ccctcataaa cacgctggac ataaacatta cctcttttgg catgttgtaa   28500
ttcaccacct cccggtacca tataaacctc tgattaaaca tggcgccatc caccaccatc   28560
ctaaaccagc tggccaaaac ctgcccgccg gctatacact gcagggaacc gggactggaa   28620
caatgacagt ggagagccca ggactcgtaa ccatggatca tcatgctcgt catgatatca   28680
atgttggcac aacacaggca cacgtgcata cacttcctca ggattacaag ctcctcccgc   28740
gttagaacca tatcccaggg aacaacccat tcctgaatca gcgtaaatcc cacactgcag   28800
ggaagacctc gcacgtaact cacgttgtgc attgtcaaag tgttacattc gggcagcagc   28860
ggatgatcct ccagtatggt agcgcgggtt tctgtctcaa aaggaggtag acgatcccta   28920
ctgtacggag tgcgccgaga caaccgagat cgtgttggtc gtagtgtcat gccaaatgga   28980
acgccggacg tagtcatatt tcctgaagca aaaccaggtg cgggcgtgac aaacagatct   29040
gcgtctccgg tctcgccgct tagatcgctc tgtgtagtag ttgtagtata tccactctct   29100
caaagcatcc aggcgccccc tggcttcggg ttctatgtaa actccttcat gcgccgctgc   29160
cctgataaca tccaccaccg cagaataagc cacacccagc caacctacac attcgttctg   29220
cgagtcacac acgggaggag cgggaagagc tggaagaacc atgattaact ttattccaaa   29280
cggtctcgga gcacttcaaa atgcaggtcc cggaggtggc acctctcgcc cccactgtgt   29340
tggtggaaaa taacagccag gtcaaaggtg acacggttct cgagatgttc cacggtggct   29400
tccagcaaag cctccacgcg cacatccaga aacaagagga cagcgaaagc gggagcgttt   29460
tctaattcct caatcatcat attacactcc tgcaccatcc ccagataatt ttcattttc    29520 cagccttgaa tgattcgtat tagttcctga ggtaaatcca agccagccat gataaaaagc   29580
tcgcgcagag cgccctccac cggcattctt aagcacaccc tcataattcc aagagattct   29640
gctcctggtt cacctgcagc agattaacaa tgggaatatc aaaatctctg ccgcgatccc   29700
taagctcctc cctcaacaat aactgtatgt aatctttcat atcatctccg aaattttag   29760 ccatagggcc gccaggaata agagcagggc aagccacatt acagataaag cgaagtcctc   29820
```

| | |
|---|---:|
| cccagtgwgc attgccaaat gtaagattga aataagcatg ctggctagac cctgtgatat | 29880 |
| cttccagata actggacaga aaatcaggca agcaattttt aagaaaatca acaaaagaaa | 29940 |
| agtcgtccag gtgcaggttt agagcctcag gaacaacgat ggaataagtg caaggagtgc | 30000 |
| gttccagcat ggttagtgtt tttttggtga tctgtagaac aaaaaataaa catgcaatat | 30060 |
| taaaccatgc tagcctggcg aacaggtggg taaatcactc tttccagcac caggcaggct | 30120 |
| acggggtctc cggcgcgacc ctcgtagaag ctgtcgccat gattgaaaag catcaccgag | 30180 |
| agaccttccc ggtggccggc atggatgatt cgagaagaag catacactcc gggaacattg | 30240 |
| gcatccgtga gtgaaaaaaa gcgacctata aagcctcggg gcactacaat gctcaatctc | 30300 |
| aattccagca aagccacccc atgcggatgg agcacaaaat tggcaggtgc gtaaaaaatg | 30360 |
| taattactcc cctcctgcac aggcagcaaa gcccccgctc cctccagaaa cacatacaaa | 30420 |
| gcctcagcgt ccatagctta ccgagcacgg caggcgcaag agtcagagaa aaggctgagc | 30480 |
| tctaacctga ctgcccgctc ctgtgctcaa tatatagccc taacctacac tgacgtaaag | 30540 |
| gccaaagtct aaaatacccc gccaaataat cacacacgcc cagcacacgc ccagaaaccg | 30600 |
| gtgacacact caaaaaaata cgcgcacttc ctcaaacgcc caaaactgcc gtcatttccg | 30660 |
| ggttcccacg ctacgtcatc aaaacacgac tttcaaattc cgtcgaccgt taaaaacgtc | 30720 |
| acccgccccg cccctaacgg tcgcccgtct ctcagccaat cagcgccccg catcccaaa | 30780 |
| ttcaaacacc tcatttgcat attaacgcgc acaaaaagtt tgaggtatat tattgatgat | 30840 |
| gg | 30842 |

<210> SEQ ID NO 11
<211> LENGTH: 1107
<212> TYPE: DNA
<213> ORGANISM: Mycobacterium tuberculosis

<400> SEQUENCE: 11

| | |
|---|---:|
| atggacgcca tgaagagggg cctgctgctg gtgctgctgc tgtgtggcgc cgtgttcgtg | 60 |
| tcccccagcc aggaaatcca cgcccggttc agacggggca gcatgcagct ggtggacaga | 120 |
| gtcagaggcg ccgtgaccgg catgagcaga cggctggtcg tgggagctgt cggagccgct | 180 |
| ctggtgtctg gactcgtggg agccgtgggc ggaacagcta cagccggcgc tttcagcaga | 240 |
| cccggcctgc ccgtggaata tctgcaggtc cccagcccca gcatgggccg ggacatcaag | 300 |
| gtgcagttcc agtctggcgg agccaacagc cctgctctgt acctgctgga cggcctgaga | 360 |
| gcccaggacg acttcagcgg ctgggacatc aacaccccg ccttcgagtg gtacgaccag | 420 |
| agcggcctgt ctgtggtcat gcctgtgggc ggccagagca gcttctacag cgactggtat | 480 |
| cagcccgctt gtggcaaggc cggctgccag acctacaagt gggagacatt cctgaccagc | 540 |
| gagctgcccg gctggctgca ggccaacaga cacgtgaagc ccaccggctc tgccgtcgtg | 600 |
| ggctgtctcta tggctgccag ctctgccctg accctggcca tctaccaccc ccagcagttc | 660 |
| gtgtacgctg gcgccatgtc tggcctgctg atccttctc aggccatggg acccaccctg | 720 |
| atcggactgg ctatgggaga tgccggcgga tacaaggcca gcgacatgtg ggcccctaaa | 780 |
| gaggaccccg cctggcagag aaacgacccc ctgctgaacg tgggcaagct gatcgccaac | 840 |
| aacaccagag tgtgggtgta ctgcggcaac ggcaagctga gcgacctggg cggcaacaac | 900 |
| ctgcccgcca agttcctgga aggcttcgtg cggaccagca acatcaagtt ccaggacgcc | 960 |
| tacaacgctg gcggcggaca caacggcgtg ttcgacttcc ccgacagcgg cacccacagc | 1020 |
| tgggagtatt ggggagccca gctgaatgcc atgaagcccg acctgcagag aggcagcatc | 1080 | cctaatcctc tgctgggcct ggactga                                                1107

<210> SEQ ID NO 12
<211> LENGTH: 368
<212> TYPE: PRT
<213> ORGANISM: Mycobacterium tuberculosis

<400> SEQUENCE: 12

Met Asp Ala Met Lys Arg Gly Leu Cys Cys Val Leu Leu Cys Gly
1               5                   10                  15

Ala Val Phe Val Ser Pro Ser Gln Glu Ile His Ala Arg Phe Arg
                20                  25                  30

Gly Ser Met Gln Leu Val Asp Arg Val Arg Gly Ala Val Thr Gly Met
                35                  40                  45

Ser Arg Arg Leu Val Val Gly Ala Val Gly Ala Ala Leu Val Ser Gly
50                  55                  60

Leu Val Gly Ala Val Gly Gly Thr Ala Thr Ala Gly Ala Phe Ser Arg
65                  70                  75                  80

Pro Gly Leu Pro Val Glu Tyr Leu Gln Val Pro Ser Pro Ser Met Gly
                85                  90                  95

Arg Asp Ile Lys Val Gln Phe Gln Ser Gly Gly Ala Asn Ser Pro Ala
                100                 105                 110

Leu Tyr Leu Leu Asp Gly Leu Arg Ala Gln Asp Asp Phe Ser Gly Trp
            115                 120                 125

Asp Ile Asn Thr Pro Ala Phe Glu Trp Tyr Asp Gln Ser Gly Leu Ser
        130                 135                 140

Val Val Met Pro Val Gly Gly Gln Ser Ser Phe Tyr Ser Asp Trp Tyr
145                 150                 155                 160

Gln Pro Ala Cys Gly Lys Ala Gly Cys Gln Thr Tyr Lys Trp Glu Thr
                165                 170                 175

Phe Leu Thr Ser Glu Leu Pro Gly Trp Leu Gln Ala Asn Arg His Val
            180                 185                 190

Lys Pro Thr Gly Ser Ala Val Val Gly Leu Ser Met Ala Ala Ser Ser
        195                 200                 205

Ala Leu Thr Leu Ala Ile Tyr His Pro Gln Gln Phe Val Tyr Ala Gly
    210                 215                 220

Ala Met Ser Gly Leu Leu Asp Pro Ser Gln Ala Met Gly Pro Thr Leu
225                 230                 235                 240

Ile Gly Leu Ala Met Gly Asp Ala Gly Gly Tyr Lys Ala Ser Asp Met
                245                 250                 255

Trp Gly Pro Lys Glu Asp Pro Ala Trp Gln Arg Asn Asp Pro Leu Leu
            260                 265                 270

Asn Val Gly Lys Leu Ile Ala Asn Asn Thr Arg Val Trp Val Tyr Cys
        275                 280                 285

Gly Asn Gly Lys Leu Ser Asp Leu Gly Gly Asn Asn Leu Pro Ala Lys
    290                 295                 300

Phe Leu Glu Gly Phe Val Arg Thr Ser Asn Ile Lys Phe Gln Asp Ala
305                 310                 315                 320

Tyr Asn Ala Gly Gly His Asn Gly Val Phe Asp Phe Pro Asp Ser
                325                 330                 335

Gly Thr His Ser Trp Glu Tyr Trp Gly Ala Gln Leu Asn Ala Met Lys
            340                 345                 350

Pro Asp Leu Gln Arg Gly Ser Ile Pro Asn Pro Leu Leu Gly Leu Asp
        355                 360                 365

<210> SEQ ID NO 13
<211> LENGTH: 2274
<212> TYPE: DNA
<213> ORGANISM: Unknown
<220> FEATURE:
<223> OTHER INFORMATION: Influenza A virus nucleoprotein and matrix protein 1
<220> FEATURE:
<221> NAME/KEY: misc_feature
<222> LOCATION: 1495..1515
<223> OTHER INFORMATION: Linker
<220> FEATURE:
<221> NAME/KEY: misc_feature
<222> LOCATION: 1..1494
<223> OTHER INFORMATION: Nucleoprotein sequence
<220> FEATURE:
<221> NAME/KEY: misc_feature
<222> LOCATION: 1516..2274
<223> OTHER INFORMATION: Matrix protein 1 sequence

<400> SEQUENCE: 13

```
atggccagcc agggcaccaa gcggagctac gagcagatgg aaaccgacgg cgaccggcag     60
aacgccaccg agatccgggc cagcgtgggc aagatgatcg acggcatcgg ccggttctac    120
atccagatgt gcaccgagct gaagctgtcc gactacgagg gccggctgat ccagaacagc    180
ctgaccatcg agaagatggt gctgtccgcc ttcgacgagc ggcggaacag atacctggaa    240
gagcacccca gcgccggcaa ggaccccaag aaaaccggcg gacccatcta ccggcgggtg    300
gacggcaagt ggatgcggga gctggtgctg tacgacaaag aggaaatccg gcggatctgg    360
cggcaggcca acaacggcga ggacgccaca gccggcctga cccacatgat gatctggcac    420
agcaacctga acgacaccac ctaccagcgg accagggccc tcgtgcggac cggcatggac    480
ccccggatgt gcagcctgat gcagggcagc acactgccca gaagaagcgg agctgccgga    540
gccgccgtga agggcatcgg caccatggtg atggaactga tccggatggt gaagcggggc    600
atcaacgacc ggaatttttg gaggggcgag aacggcagaa agactagaag cgcctacgag    660
cggatgtgca acatcctgaa gggcaagttc cagacagccg cccagcgggc catggtggac    720
caggtccggg agagccggaa ccccggcaac gccgagatcg aggacctgat cttcctggcc    780
cggtccgccc tgatcctgcg gggcagcgtg gcccacaaga gctgcctgcc cgcctgcgtg    840
tacggccctg ccgtgagcag cggctacgac ttcgagaaag agggctacag cctggtcggc    900
atcgacccct tcaagctgct gcagaacagc caggtgtaca gcctgatccg gcccaacgag    960
aaccccgccc acaagtccca gctggtctgg atggcctgcc acagcgccgc cttcgaggat   1020
ctgcggctgc tgtccttcat ccggggcacc aaggtgtccc ccaggggcaa gctgtccacc   1080
agaggcgtgc agatcgccag caacgagaac atggacaaca tgggcagcag caccctggaa   1140
ctgcggagcg gctactgggc catccggacc cggtccggcg gcaacaccaa ccagcagcgg   1200
gccagcgccg gacagatcag cgtgcagccc accttctccg tgcagcggaa cctgcccttc   1260
gagaagagca ccgtgatggc cgccttcacc ggcaacaccg agggccggac cagcgacatg   1320
cgggccgaga ttatccggat gatggaaggc gccaagcccg aggaagtgag cttccggggc   1380
aggggcgtgt tcgagctgtc cgatgagaag gccaccaacc ccatcgtgcc cagcttcgag   1440
atgagcaacg agggcagcta cttcttcggc gacaacgccg aggaatacga caatggcggc   1500
ggaccaggcg gcggaatgag cctgctgacc gaggtggaga cctacgtgct gtccatcgtg   1560
cctagcggcc ctctgaaggc cgagatcgcc cagcggctgg aagatgtgtt cgccggcaag   1620
aacaccgacc tggaagccct gatggaatgg ctgaaaaccc ggcccatcct gagccccctg   1680
```

-continued

```
accaagggca tcctgggctt cgtgttcacc ctgaccgtgc ccagcgagcg gggcctgcag   1740
cggcggagat tcgtgcagaa cgccctgaac ggcaacggcg accccaacaa catggataag   1800
gccgtgaagc tgtaccggaa gctgaagcgg gagatcacct tccacggcgc caaagagatc   1860
gccctgagct acagcgccgg agccctggcc agctgcatgg gcctgatcta caaccggatg   1920
ggcgccgtga ccaccgaggt ggccttcggc ctggtctgcg ccacctgcga gcagatcgcc   1980
gacagccagc acagatccca ccggcagatg gtggccacaa ccaaccctct gatcaagcac   2040
gagaaccgga tggtgctggc tagcaccacc gccaaggcca tggaacagat ggccggcagc   2100
agcgagcagg ccgccgaagc catggaaatc gccagccagg ccagacagat ggtgcaggcc   2160
atgcggaccg tgggcaccca ccccagcagc tccaccggcc tgcgggacga cctgctggaa   2220
aacctgcaga cctaccagaa acggatgggg gtgcagatgc agcggttcaa gtga         2274


<210> SEQ ID NO 14
<211> LENGTH: 757
<212> TYPE: PRT
<213> ORGANISM: Unknown
<220> FEATURE:
<223> OTHER INFORMATION: Influenza A virus nucleoprotein and matrix
      protein 1

<400> SEQUENCE: 14

Met Ala Ser Gln Gly Thr Lys Arg Ser Tyr Glu Gln Met Glu Thr Asp
1               5                   10                  15

Gly Asp Arg Gln Asn Ala Thr Glu Ile Arg Ala Ser Val Gly Lys Met
            20                  25                  30

Ile Asp Gly Ile Gly Arg Phe Tyr Ile Gln Met Cys Thr Glu Leu Lys
        35                  40                  45

Leu Ser Asp Tyr Glu Gly Arg Leu Ile Gln Asn Ser Leu Thr Ile Glu
    50                  55                  60

Lys Met Val Leu Ser Ala Phe Asp Glu Arg Arg Asn Arg Tyr Leu Glu
65                  70                  75                  80

Glu His Pro Ser Ala Gly Lys Asp Pro Lys Lys Thr Gly Gly Pro Ile
                85                  90                  95

Tyr Arg Arg Val Asp Gly Lys Trp Met Arg Glu Leu Val Leu Tyr Asp
            100                 105                 110

Lys Glu Glu Ile Arg Arg Ile Trp Arg Gln Ala Asn Asn Gly Glu Asp
        115                 120                 125

Ala Thr Ala Gly Leu Thr His Met Met Ile Trp His Ser Asn Leu Asn
    130                 135                 140

Asp Thr Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Ile Gly Thr Met Val Met Glu
            180                 185                 190

Leu Ile Arg Met Val Lys Arg Gly Ile Asn Asp Arg Asn Phe Trp Arg
        195                 200                 205

Gly Glu Asn Gly Arg Lys Thr Arg Ser Ala Tyr Glu Arg Met Cys Asn
    210                 215                 220

Ile Leu Lys Gly Lys Phe Gln Thr Ala Ala Gln Arg Ala Met Val Asp
225                 230                 235                 240

Gln Val Arg Glu Ser Arg Asn Pro Gly Asn Ala Glu Ile Glu Asp Leu
                245                 250                 255
```

```
Ile Phe Leu Ala Arg Ser Ala Leu Ile Leu Arg Gly Ser Val Ala His
            260                 265                 270

Lys Ser Cys Leu Pro Ala Cys Val Tyr Gly Pro Ala Val Ser Ser Gly
            275                 280                 285

Tyr Asp Phe Glu Lys Glu Gly Tyr Ser Leu Val Gly Ile Asp Pro Phe
290                 295                 300

Lys Leu Leu Gln Asn Ser Gln Val Tyr Ser Leu Ile Arg Pro Asn Glu
305                 310                 315                 320

Asn Pro Ala His Lys Ser Gln Leu Val Trp Met Ala Cys His Ser Ala
                325                 330                 335

Ala Phe Glu Asp Leu Arg Leu Leu Ser Phe Ile Arg Gly Thr Lys Val
            340                 345                 350

Ser Pro Arg Gly Lys Leu Ser Thr Arg Gly Val Gln Ile Ala Ser Asn
            355                 360                 365

Glu Asn Met Asp Asn Met Gly Ser Ser Thr Leu Glu Leu Arg Ser Gly
            370                 375                 380

Tyr Trp Ala Ile Arg Thr Arg Ser Gly Gly Asn Thr Asn Gln Gln Arg
385                 390                 395                 400

Ala Ser Ala Gly Gln Ile Ser Val Gln Pro Thr Phe Ser Val Gln Arg
            405                 410                 415

Asn Leu Pro Phe Glu Lys Ser Thr Val Met Ala Ala Phe Thr Gly Asn
            420                 425                 430

Thr Glu Gly Arg Thr Ser Asp Met Arg Ala Glu Ile Ile Arg Met Met
            435                 440                 445

Glu Gly Ala Lys Pro Glu Glu Val Ser Phe Arg Gly Arg Gly Val Phe
            450                 455                 460

Glu Leu Ser Asp Glu Lys Ala Thr Asn Pro Ile Val Pro Ser Phe Glu
465                 470                 475                 480

Met Ser Asn Glu Gly Ser Tyr Phe Phe Gly Asp Asn Ala Glu Glu Tyr
            485                 490                 495

Asp Asn Gly Gly Gly Pro Gly Gly Gly Met Ser Leu Leu Thr Glu Val
            500                 505                 510

Glu Thr Tyr Val Leu Ser Ile Val Pro Ser Gly Pro Leu Lys Ala Glu
            515                 520                 525

Ile Ala Gln Arg Leu Glu Asp Val Phe Ala Gly Lys Asn Thr Asp Leu
            530                 535                 540

Glu Ala Leu Met Glu Trp Leu Lys Thr Arg Pro Ile Leu Ser Pro Leu
545                 550                 555                 560

Thr Lys Gly Ile Leu Gly Phe Val Phe Thr Leu Thr Val Pro Ser Glu
                565                 570                 575

Arg Gly Leu Gln Arg Arg Phe Val Gln Asn Ala Leu Asn Gly Asn
            580                 585                 590

Gly Asp Pro Asn Asn Met Asp Lys Ala Val Lys Leu Tyr Arg Lys Leu
            595                 600                 605

Lys Arg Glu Ile Thr Phe His Gly Ala Lys Glu Ile Ala Leu Ser Tyr
            610                 615                 620

Ser Ala Gly Ala Leu Ala Ser Cys Met Gly Leu Ile Tyr Asn Arg Met
625                 630                 635                 640

Gly Ala Val Thr Thr Glu Val Ala Phe Gly Leu Val Cys Ala Thr Cys
            645                 650                 655

Glu Gln Ile Ala Asp Ser Gln His Arg Ser His Arg Gln Met Val Ala
            660                 665                 670
```

```
Thr Thr Asn Pro Leu Ile Lys His Glu Asn Arg Met Val Leu Ala Ser
            675                 680                 685
Thr Thr Ala Lys Ala Met Glu Gln Met Ala Gly Ser Ser Glu Gln Ala
        690                 695                 700
Ala Glu Ala Met Glu Ile Ala Ser Gln Ala Arg Gln Met Val Gln Ala
705                 710                 715                 720
Met Arg Thr Val Gly Thr His Pro Ser Ser Ser Thr Gly Leu Arg Asp
                725                 730                 735
Asp Leu Leu Glu Asn Leu Gln Thr Tyr Gln Lys Arg Met Gly Val Gln
            740                 745                 750
Met Gln Arg Phe Lys
        755

<210> SEQ ID NO 15
<211> LENGTH: 9
<212> TYPE: PRT
<213> ORGANISM: Artificial
<220> FEATURE:
<223> OTHER INFORMATION: Polypeptide linker sequence

<400> SEQUENCE: 15

Ile Pro Asn Pro Leu Leu Gly Leu Asp
1               5

<210> SEQ ID NO 16
<211> LENGTH: 2948
<212> TYPE: DNA
<213> ORGANISM: Chimpanzee adenovirus Ch68

<400> SEQUENCE: 16
gtaggtgtca gctgatcgcc agggtattta aacctgcgct ctccagtcaa gaggccactc      60
ttgagtgcca gcgagaagag ttttctcctc cgcgccgcga gtcagatcta cactttgaaa     120
gatgaggcac ctgagagacc tgcccgatga gaaaatcatc atcgcttccg ggaacgagat     180
tctggaactg gtggtaaatg ccatgatggg cgacgaccct ccggagcccc ccaccccatt     240
tgagacacct tcgctgcacg atttgtatga tctggaggtg gatgtgcccg aggacgatcc     300
caatgaggag gcggtaaatg atttttttag cgatgccgcg ctgctagctg ccgaggaggc     360
ttcgagctct agctcagaca gcgactcttc actgcatacc cctagacccg gcagaggtga     420
gaaaagatc cccgagctta aggggaaga gatggacttg cgctgctatg aggaatgctt      480
gccccccgagc gatgatgagg acgagcaggc gatccagaac gcagcgagcc agggagtgca     540
agccgccagc gagagctttg cgctggactg cccgcctctg cccggacacg gctgtaagtc     600
ttgtgaattt catcgcatga atactggaga taaagctgtg ttgtgtgcac tttgctatat     660
gagagcttac aaccattgtg tttacagtaa gtgtgattaa gttgaacttt agagggaggc     720
agagagcagg gtgactgggc gatgactggt ttatttatgt atatatgttc tttatatagg     780
tcccgtctct gacgcagatg atgagacccc cactacaaag tccacttcgt cacccccaga     840
aattggcaca tctccacctg agaatattgt tagaccagtt cctgttagag ccactgggag     900
gagagcagct gtggaatgtt tggatgactt gctacagggt ggggttgaac ctttggactt     960
gtgtacccgg aaacgcccca ggcactaagt gccacacatg tgtgtttact tgaggtgatg    1020
tcagtattta agggtgtgg agtgcaataa aaaatgtgtt gactttaagt gcgtggttta     1080
tgactcaggg gtggggactg tgagtatata agcaggtgca gacctgtgtg ttagctcag      1140
agcggcatgg agatttggac ggtcttggaa gactttcaca agactagaca gctgctagag    1200
```

| | |
|---|---:|
| aacgcctcga acggagtctc ttacctgtgg agattctgct tcggtggcga cctagctagg | 1260 |
| ctagtctaca gggccaaaca ggattatagt gaacaatttg aggttatttt gagagagtgt | 1320 |
| tctggtctttt ttgacgctct taacttgggc catcagtctc actttaacca gaggatttcg | 1380 |
| agagcccttg attttactac tcctggcaga accactgcag cagtagcctt ttttgctttt | 1440 |
| attcttgaca aatggagtca agaaacccat ttcagcaggg attaccagct ggatttctta | 1500 |
| gcagtagctt tgtggagaac atggaagtgc cagcgcctga atgcaatctc cggctacttg | 1560 |
| ccggtacagc cgctagacac tctgaggatc ctgaatctcc aggagagtcc cagggcacgc | 1620 |
| caacgtcgcc agcagcagca gcaggaggag gatcaagaag agaacccgag agccggcctg | 1680 |
| gaccctccgg cggaggagga ggagtagctg acctgtttcc tgaactgcgc cgggtgctga | 1740 |
| ctaggtcttc gagtggtcgg gagagggggga ttaagcggga gaggcatgat gagactaatc | 1800 |
| acagaactga actgactgtg ggtctgatga gtcgcaagcg cccagaaaca gtgtggtggc | 1860 |
| atgaggtgca gtcgactggc acagatgagg tgtcggtgat gcatgagagg ttttctctag | 1920 |
| aacaagtcaa gacttgttgg ttagagcctg aggatgattg ggaggtagcc atcaggaatt | 1980 |
| atgccaagct ggctctgagg ccagacaaga agtacaagat tactaagctg ataaatatca | 2040 |
| gaaatgcctc ctacatctca gggaatgggg ctgaagtgga gatctgtctc caggaaaggg | 2100 |
| tggctttcag atgctgcatg atgaaatatgt acccgggagt ggtgggcatg gatggggtta | 2160 |
| cctttatgaa catgaggttc aggggagatg ggtataatgg cacggtcttt atggccaata | 2220 |
| ccaagctgac agtccatggc tgctccttct ttgggtttaa taacacctgc atcgaggcct | 2280 |
| gggggtcaggt cggtgtgagg ggctgcagtt tttcagccaa ctggatgggg gtcgtgggca | 2340 |
| ggaccaagag tatgctgtcc gtgaagaaat gcttgtttga gaggtgccac ctgggggtga | 2400 |
| tgagcgaggg cgaagccaga atccgccact gcgcctctac cgagacgggc tgctttgtgc | 2460 |
| tgtgcaaggg caatgctaag atcaagcata atatgatctg tggagcctcg acgagcgcg | 2520 |
| gctaccagat gctgacctgc gccggcggga acagccatat gctggccacc gtacatgtgg | 2580 |
| cttcccatgc tcgcaagccc tggcccgagt tcgagcacaa tgtcatgacc aggtgcaata | 2640 |
| tgcatctggg gtcccgccga ggcatgttca tgccctacca gtgcaacctg aattatgtga | 2700 |
| aggtgctgct ggagcccgat gccatgtcca gagtgagcct gacgggggtg tttgacatga | 2760 |
| atgtggaggt gtgaagatt ctgagatatg atgaatccaa gaccaggtgc cgagcctgcg | 2820 |
| agtgcggagg gaagcatgcc aggttccagc ccgtgtgtgt ggatgtgacg gaggacctgc | 2880 |
| gacccgatca tttggtgttg ccctgcaccg ggacggagtt cggttccagc ggggaagaat | 2940 |
| ctgactag | 2948 |

<210> SEQ ID NO 17
<211> LENGTH: 4707
<212> TYPE: DNA
<213> ORGANISM: Chimpanzee adenovirus C68

<400> SEQUENCE: 17

| | |
|---|---:|
| atgtcccatg gtggcgcagc tgacctagct cggcttcgac acctggacca ctgccgccgc | 60 |
| ttccgctgct tcgctcggga tctcgccgag tttgcctact ttgagctgcc cgaggagcac | 120 |
| cctcagggcc cggcccacgg agtgcggatc gtcgtcgaag ggggcctcga ctcccacctg | 180 |
| cttcggatct tcagccagcg tccgatcctg tcgagcgcg agcaaggaca gacccttctg | 240 |
| actctgtact gcatctgcaa ccaccccggc ctgcatgaaa gtctttgttg tctgctgtgt | 300 |
| actgagtata ataaaagctg agatcagcga ctactccgga cttccgtgtg ttcctgaatc | 360 |

```
catcaaccag tctttgttct tcaccgggaa cgagaccgag ctccagctcc agtgtaagcc      420
ccacaagaag tacctcacct ggctgttcca gggctccccg atcgccgttg tcaaccactg      480
cgacaacgac ggagtcctgc tgagcggccc tgccaacctt acttttcca cccgcagaag       540 caagctccag ctcttccaac ccttcctccc cgggacctat cagtgcgtct cgggaccctg      600
ccatcacacc ttccacctga tcccgaatac acagcgtcg ctccccgcta ctaacaacca       660
aactaacctc caccaacgcc accgtcgcga cctttctgaa tctaatacta cacccacac       720 cggaggtgag ctccgaggtc aaccaacctc tgggatttac tacggcccct gggaggtggt     780
tgggttaata gcgctaggcc tagttgcggg tgggcttttg gttctctgct acctatacct      840
cccttgctgt tcgtacttag tggtgctgtg ttgctggttt aagaaatggg gaagatcacc      900
ctagtgagct gcggtgcgct ggtggcgtg ttgctttcga ttgtgggact gggcggtgcg       960
gctgtagtga aggagaaggc cgatccctgc ttgcatttca atcccaacaa atgccagctg     1020
agttttcagc ccgatggcaa tcggtgcgcg gtactgatca agtgcggatg ggaatgcgag     1080
aacgtgagaa tcgagtacaa taacaagact cggaacaata ctctcgcgtc cgtgtggcag     1140
cccggggacc ccgagtggta caccgtctct gtccccggtg ctgacggctc cccgcgcacc     1200
gtgaataata ctttcatttt tgcgcacatg tgcgacacgg tcatgtggat gagcaagcag     1260
tacgatatgt ggccccccac gaaggagaac atcgtggtct tctccatcgc ttacagcctg     1320
tgcacggcgc taatcaccgc tatcgtgtgc ctgagcattc acatgctcat cgctattcgc     1380
cccagaaata atgccgaaaa agaaaaacag ccataacgtt tttttcaca ccttttttcag      1440 accatggcct ctgttaaatt tttgctttta tttgccagtc tcattgccgt cattcatgga     1500
atgagtaatg agaaaattac tatttacact ggcactaatc acacattgaa aggtccagaa     1560
aaagccacag aagtttcatg gtattgttat tttaatgaat cagatgtatc tactgaactc     1620
tgtggaaaca ataacaaaaa aaatgagagc attactctca tcaagtttca atgtggatct     1680
gacttaaccc taattaacat cactagagac tatgtaggta tgtattatgg aactacagca     1740
ggcatttcgg acatggaatt ttatcaagtt tctgtgtctg aacccaccac gcctagaatg     1800
accacaacca caaaaactac acctgttacc actatgcagc tcactaccaa taacattttt     1860
gccatgcgtc aaatggtcaa caatagcact caacccaccc cacccagtga ggaaattccc     1920
aaatccatga ttggcattat tgttgctgta gtggtgtgca tgttgatcat cgccttgtgc     1980
atggtgtact atgccttctg ctacagaaag cacagactga cgacaagct ggaacactta       2040 ctaagtgttg aattttaatt ttttagaacc atgaagatcc taggcctttt aattttttct     2100
atcattacct ctgctctatg caattctgac aatgaggacg ttactgtcgt tgtcggatca     2160
aattatacac tgaaaggtcc agcgaagggt atgctttcgt ggtattgcta ttttggatct     2220
gacactacag aaactgaatt atgcaatctt aagaatggca aaattcaaaa ttctaaaatt     2280
aacaattata tatgcaatgg tactgatctg atactcctca atatcacgaa atcatatgct     2340
ggcagttaca cctgccctgg agatgatgct gacagtatga tttttacaa agtaactgtt      2400 gttgatccca ctactccacc tccacccacc acaactactc acaccacaca cacagatcaa     2460
accgcagcag aggaggcagc aaagttagcc ttgcaggtcc aagacagttc atttgttggc     2520 attacccctca cacctgatca gcggtgtccg gggctgctag tcagcggcat tgtcggtgtg     2580
ctttcgggat tagcagtcat aatcatctgc atgttcattt ttgcttgctg ctatagaagg     2640
ctttaccgac aaaaatcaga cccactgctg aacctctatg tttaatttt tccagagtca     2700
```

```
tgaaggcagt tagcgctcta gttttttgtt ctttgattgg cattgttttt tgcaatccta      2760
ttcctaaagt tagctttatt aaagatgtga atgttactga gggggggcaat gtgacactgg    2820 taggtgtaga gggtgctgaa acaccaccct ggacaaaata ccacctcaat gggtggaaag     2880
atatttgcaa ttggagtgta ttagtttata catgtgaggg agttaatctt accattgtca     2940
atgccacctc agctcaaaat ggtagaattc aaggacaaag tgtcagtgta tctaatgggt    3000 attttacccca acatactttt atctatgacg ttaaagtcat accactgcct acgcctagcc   3060
cacctagcac taccacacag acaacccaca ctacacagac aaccacatac agtacattaa    3120
atcagcctac caccactaca gcagcagagg ttgccagctc gtctgggggtc cgagtggcat   3180 ttttgatgtg ggcccccatct agcagtccca ctgctagtac caatgagcag actactgaat  3240
ttttgtccac tgtcgagagc cacaccacag ctacctccag tgccttctct agcaccgcca   3300
atctctcctc gctttcctct acaccaatca gtcccgctac tactcctagc cccgctcctc   3360
ttcccactcc cctgaagcaa acagacggcg gcatgcaatg gcagatcacc ctgctcattg   3420
tgatcgggtt ggtcatcctg gccgtgttgc tctactacat cttctgccgc cgcattccca   3480
acgcgcaccg caagccggtc tacaagccca tcattgtcgg gcagccggag ccgcttcagg   3540
tggaaggggg tctaaggaat cttctcttct cttttacagt atggtgattg aactatgatt    3600
cctagacaat tcttgatcac tattcttatc tgcctcctcc aagtctgtgc caccctcgct   3660
ctggtggcca acgccagtcc agactgtatt gggcccttcg cctcctacgt gctctttgcc   3720
ttcaccacct gcatctgctg ctgtagcata gtctgcctgc ttatcacctt cttccagttc   3780
attgactgga tctttgtgcg catcgcctac ctgcgccacc accccagta ccgcgaccag    3840 cgagtggcgc ggctgctcag gctcctctga taagcatgcg ggctctgcta cttctcgcgc   3900
ttctgctgtt agtgctcccc cgtcccgtcg acccccggtc ccccacccag tccccccgagg  3960 aggtccgcaa atgcaaattc caagaaccct ggaaattcct caaatgctac cgccaaaaat   4020
cagacatgca tcccagctgg atcatgatca ttgggatcgt gaacattctg gcctgcaccc   4080
tcatctcctt tgtgatttac ccctgcttttg actttggttg gaactcgcca gaggcgctct   4140
atctcccgcc tgaacctgac acaccaccac agcaacctca ggcacacgca ctaccaccac   4200
tacagcctag gccacaatac atgcccatat tagactatga ggccgagcca cagcgaccca   4260
tgctccccgc tattagttac ttcaatctaa ccggcggaga tgactgaccc actgccaac    4320 aacaacgtca acgaccttct cctggacatg gacggccgcg cctcggagca gcgactcgcc   4380
caacttcgca ttcgccagca gcaggagaga gccgtcaagg agctgcagga tgcggtggcc   4440
atccaccagt gcaagagagg catcttctgc ctggtgaaac aggccaagat ctcctacgag   4500
gtcactccaa acgaccatcg cctctcctac gagctcctgc agcagcgcca gaagttcacc   4560
tgcctggtcg gagtcaaccc catcgtcatc acccagcagt ctggcgatac caagggggtgc  4620 atccactgct cctgcgactc ccccgactgc gtccacactc tgatcaagac cctctgcggc   4680
ctccgcgacc tcctccccat gaactaa                                        4707
```

<210> SEQ ID NO 18
<211> LENGTH: 933
<212> TYPE: PRT
<213> ORGANISM: Chimpanzee adenovirus C68

<400> SEQUENCE: 18

Met Ala Thr Pro Ser Met Leu Pro Gln Trp Ala Tyr Met His Ile Ala
1               5                   10                  15

-continued

```
Gly Gln Asp Ala Ser Glu Tyr Leu Ser Pro Gly Leu Val Gln Phe Ala
             20                  25                  30

Arg Ala Thr Asp Thr Tyr Phe Ser Leu Gly Asn Lys Phe Arg Asn Pro
         35                  40                  45

Thr Val Ala Pro Thr His Asp Val Thr Thr Asp Arg Ser Gln Arg Leu
     50                  55                  60

Thr Leu Arg Phe Val Pro Val Asp Arg Glu Asp Asn Thr Tyr Ser Tyr
 65                  70                  75                  80

Lys Val Arg Tyr Thr Leu Ala Val Gly Asp Asn Arg Val Leu Asp Met
                 85                  90                  95

Ala Ser Thr Tyr Phe Asp Ile Arg Gly Val Leu Asp Arg Gly Pro Ser
            100                 105                 110

Phe Lys Pro Tyr Ser Gly Thr Ala Tyr Asn Ser Leu Ala Pro Lys Gly
        115                 120                 125

Ala Pro Asn Thr Cys Gln Trp Thr Tyr Lys Ala Asp Gly Glu Thr Ala
    130                 135                 140

Thr Glu Lys Thr Tyr Thr Tyr Gly Asn Ala Pro Val Gln Gly Ile Asn
145                 150                 155                 160

Ile Thr Lys Asp Gly Ile Gln Leu Gly Thr Asp Thr Asp Gln Pro
                165                 170                 175

Ile Tyr Ala Asp Lys Thr Tyr Gln Pro Glu Pro Gln Val Gly Asp Ala
                180                 185                 190

Glu Trp His Asp Ile Thr Gly Thr Asp Glu Lys Tyr Gly Gly Arg Ala
            195                 200                 205

Leu Lys Pro Asp Thr Lys Met Lys Pro Cys Tyr Gly Ser Phe Ala Lys
    210                 215                 220

Pro Thr Asn Lys Glu Gly Gln Ala Asn Val Lys Thr Gly Thr Gly
225                 230                 235                 240

Thr Thr Lys Glu Tyr Asp Ile Asp Met Ala Phe Phe Asp Asn Arg Ser
                245                 250                 255

Ala Ala Ala Ala Gly Leu Ala Pro Glu Ile Val Leu Tyr Thr Glu Asn
            260                 265                 270

Val Asp Leu Glu Thr Pro Asp Thr His Ile Val Tyr Lys Ala Gly Thr
    275                 280                 285

Asp Asp Ser Ser Ser Ile Asn Leu Gly Gln Gln Ala Met Pro Asn
290                 295                 300

Arg Pro Asn Tyr Ile Gly Phe Arg Asp Asn Phe Ile Gly Leu Met Tyr
305                 310                 315                 320

Tyr Asn Ser Thr Gly Asn Met Gly Val Leu Ala Gly Gln Ala Ser Gln
                325                 330                 335

Leu Asn Ala Val Val Asp Leu Gln Asp Arg Asn Thr Glu Leu Ser Tyr
            340                 345                 350

Gln Leu Leu Leu Asp Ser Leu Gly Asp Arg Thr Arg Tyr Phe Ser Met
        355                 360                 365

Trp Asn Gln Ala Val Asp Ser Tyr Asp Pro Asp Val Arg Ile Ile Glu
    370                 375                 380

Asn His Gly Val Glu Asp Glu Leu Pro Asn Tyr Cys Phe Pro Leu Asp
385                 390                 395                 400

Ala Val Gly Arg Thr Asp Thr Tyr Gln Gly Ile Lys Ala Asn Gly Thr
                405                 410                 415

Asp Gln Thr Thr Trp Thr Lys Asp Asp Ser Val Asn Asp Ala Asn Glu
            420                 425                 430

Ile Gly Lys Gly Asn Pro Phe Ala Met Glu Ile Asn Ile Gln Ala Asn
```

```
            435                 440                 445
Leu Trp Arg Asn Phe Leu Tyr Ala Asn Val Ala Leu Tyr Leu Pro Asp
450                 455                 460

Ser Tyr Lys Tyr Thr Pro Ala Asn Val Thr Leu Pro Thr Asn Thr Asn
465                 470                 475                 480

Thr Tyr Asp Tyr Met Asn Gly Arg Val Val Ala Pro Ser Leu Val Asp
                    485                 490                 495

Ser Tyr Ile Asn Ile Gly Ala Arg Trp Ser Leu Asp Pro Met Asp Asn
                500                 505                 510

Val Asn Pro Phe Asn His His Arg Asn Ala Gly Leu Arg Tyr Arg Ser
            515                 520                 525

Met Leu Leu Gly Asn Gly Arg Tyr Val Pro Phe His Ile Gln Val Pro
530                 535                 540

Gln Lys Phe Phe Ala Ile Lys Ser Leu Leu Leu Pro Gly Ser Tyr
545                 550                 555                 560

Thr Tyr Glu Trp Asn Phe Arg Lys Asp Val Asn Met Ile Leu Gln Ser
                565                 570                 575

Ser Leu Gly Asn Asp Leu Arg Thr Asp Gly Ala Ser Ile Ser Phe Thr
                580                 585                 590

Ser Ile Asn Leu Tyr Ala Thr Phe Phe Pro Met Ala His Asn Thr Ala
            595                 600                 605

Ser Thr Leu Glu Ala Met Leu Arg Asn Asp Thr Asn Asp Gln Ser Phe
610                 615                 620

Asn Asp Tyr Leu Ser Ala Ala Asn Met Leu Tyr Pro Ile Pro Ala Asn
625                 630                 635                 640

Ala Thr Asn Val Pro Ile Ser Ile Pro Ser Arg Asn Trp Ala Ala Phe
                645                 650                 655

Arg Gly Trp Ser Phe Thr Arg Leu Lys Thr Lys Glu Thr Pro Ser Leu
                660                 665                 670

Gly Ser Gly Phe Asp Pro Tyr Phe Val Tyr Ser Gly Ser Ile Pro Tyr
            675                 680                 685

Leu Asp Gly Thr Phe Tyr Leu Asn His Thr Phe Lys Lys Val Ser Ile
690                 695                 700

Thr Phe Asp Ser Ser Val Ser Trp Pro Gly Asn Asp Arg Leu Leu Thr
705                 710                 715                 720

Pro Asn Glu Phe Glu Ile Lys Arg Thr Val Asp Gly Glu Gly Tyr Asn
                725                 730                 735

Val Ala Gln Cys Asn Met Thr Lys Asp Trp Phe Leu Val Gln Met Leu
                740                 745                 750

Ala His Tyr Asn Ile Gly Tyr Gln Gly Phe Tyr Val Pro Glu Gly Tyr
            755                 760                 765

Lys Asp Arg Met Tyr Ser Phe Arg Asn Phe Gln Pro Met Ser Arg
770                 775                 780

Gln Val Val Asp Glu Val Asn Tyr Lys Asp Tyr Gln Ala Val Thr Leu
785                 790                 795                 800

Ala Tyr Gln His Asn Asn Ser Gly Phe Val Gly Tyr Leu Ala Pro Thr
                805                 810                 815

Met Arg Gln Gly Gln Pro Tyr Pro Ala Asn Tyr Pro Tyr Pro Leu Ile
                820                 825                 830

Gly Lys Ser Ala Val Thr Ser Val Thr Gln Lys Lys Phe Leu Cys Asp
            835                 840                 845

Arg Val Met Trp Arg Ile Pro Phe Ser Ser Asn Phe Met Ser Met Gly
850                 855                 860
```

```
Ala Leu Thr Asp Leu Gly Gln Asn Met Leu Tyr Ala Asn Ser Ala His
865                 870                 875                 880

Ala Leu Asp Met Asn Phe Glu Val Asp Pro Met Asp Glu Ser Thr Leu
            885                 890                 895

Leu Tyr Val Val Phe Glu Val Phe Asp Val Val Arg Val His Gln Pro
            900                 905                 910

His Arg Gly Val Ile Glu Ala Val Tyr Leu Arg Thr Pro Phe Ser Ala
        915                 920                 925

Gly Asn Ala Thr Thr
        930

<210> SEQ ID NO 19
<211> LENGTH: 425
<212> TYPE: PRT
<213> ORGANISM: Chimpanzee adenovirus C68

<400> SEQUENCE: 19

Met Ser Lys Lys Arg Val Arg Val Asp Asp Asp Phe Asp Pro Val Tyr
1               5                   10                  15

Pro Tyr Asp Ala Asp Asn Ala Pro Thr Val Pro Phe Ile Asn Pro Pro
            20                  25                  30

Phe Val Ser Ser Asp Gly Phe Gln Glu Lys Pro Leu Gly Val Leu Ser
        35                  40                  45

Leu Arg Leu Ala Asp Pro Val Thr Thr Lys Asn Gly Glu Ile Thr Leu
50                  55                  60

Lys Leu Gly Glu Gly Val Asp Leu Asp Ser Ser Gly Lys Leu Ile Ser
65                  70                  75                  80

Asn Thr Ala Thr Lys Ala Ala Ala Pro Leu Ser Phe Ser Asn Asn Thr
                85                  90                  95

Ile Ser Leu Asn Met Asp His Pro Phe Tyr Thr Lys Asp Gly Lys Leu
            100                 105                 110

Ser Leu Gln Val Ser Pro Pro Leu Asn Ile Leu Arg Thr Ser Ile Leu
        115                 120                 125

Asn Thr Leu Ala Leu Gly Phe Gly Ser Gly Leu Gly Leu Arg Gly Ser
130                 135                 140

Ala Leu Ala Val Gln Leu Val Ser Pro Leu Thr Phe Asp Thr Asp Gly
145                 150                 155                 160

Asn Ile Lys Leu Thr Leu Asp Arg Gly Leu His Val Thr Thr Gly Asp
                165                 170                 175

Ala Ile Glu Ser Asn Ile Ser Trp Ala Lys Gly Leu Lys Phe Glu Asp
            180                 185                 190

Gly Ala Ile Ala Thr Asn Ile Gly Asn Gly Leu Glu Phe Gly Ser Ser
        195                 200                 205

Ser Thr Glu Thr Gly Val Asp Asp Ala Tyr Pro Ile Gln Val Lys Leu
210                 215                 220

Gly Ser Gly Leu Ser Phe Asp Ser Thr Gly Ala Ile Met Ala Gly Asn
225                 230                 235                 240

Lys Glu Asp Asp Lys Leu Thr Leu Trp Thr Thr Pro Asp Pro Ser Pro
                245                 250                 255

Asn Cys Gln Ile Leu Ala Glu Asn Asp Ala Lys Leu Thr Leu Cys Leu
            260                 265                 270

Thr Lys Cys Gly Ser Gln Ile Leu Ala Thr Val Ser Val Leu Val Val
        275                 280                 285

Gly Ser Gly Asn Leu Asn Pro Ile Thr Gly Thr Val Ser Ser Ala Gln
```

```
            290                 295                 300
Val Phe Leu Arg Phe Asp Ala Asn Gly Val Leu Leu Thr Glu His Ser
305                 310                 315                 320

Thr Leu Lys Lys Tyr Trp Gly Tyr Arg Gln Gly Asp Ser Ile Asp Gly
                325                 330                 335

Thr Pro Tyr Thr Asn Ala Val Gly Phe Met Pro Asn Leu Lys Ala Tyr
                340                 345                 350

Pro Lys Ser Gln Ser Ser Thr Thr Lys Asn Asn Ile Val Gly Gln Val
                355                 360                 365

Tyr Met Asn Gly Asp Val Ser Lys Pro Met Leu Leu Thr Ile Thr Leu
        370                 375                 380

Asn Gly Thr Asp Asp Ser Asn Ser Thr Tyr Ser Met Ser Phe Ser Tyr
385                 390                 395                 400

Thr Trp Thr Asn Gly Ser Tyr Val Gly Ala Thr Phe Gly Ala Asn Ser
                405                 410                 415

Tyr Thr Phe Ser Tyr Ile Ala Gln Glu
                420                 425

<210> SEQ ID NO 20
<211> LENGTH: 534
<212> TYPE: PRT
<213> ORGANISM: Chimpanzee adenovirus C68

<400> SEQUENCE: 20

Met Met Arg Arg Ala Tyr Pro Glu Gly Pro Pro Ser Tyr Glu Ser
1               5                   10                  15

Val Met Gln Gln Ala Met Ala Ala Ala Met Gln Pro Pro Leu Glu
                20                  25                  30

Ala Pro Tyr Val Pro Pro Arg Tyr Leu Ala Pro Thr Glu Gly Arg Asn
                35                  40                  45

Ser Ile Arg Tyr Ser Glu Leu Ala Pro Leu Tyr Asp Thr Thr Arg Leu
        50                  55                  60

Tyr Leu Val Asp Asn Lys Ser Ala Asp Ile Ala Ser Leu Asn Tyr Gln
65                  70                  75                  80

Asn Asp His Ser Asn Phe Leu Thr Thr Val Val Gln Asn Asn Asp Phe
                85                  90                  95

Thr Pro Thr Glu Ala Ser Thr Gln Thr Ile Asn Phe Asp Glu Arg Ser
                100                 105                 110

Arg Trp Gly Gly Gln Leu Lys Thr Ile Met His Thr Asn Met Pro Asn
        115                 120                 125

Val Asn Glu Phe Met Tyr Ser Asn Lys Phe Lys Ala Arg Val Met Val
130                 135                 140

Ser Arg Lys Thr Pro Asn Gly Val Thr Val Thr Glu Asp Tyr Asp Gly
145                 150                 155                 160

Ser Gln Asp Glu Leu Lys Tyr Glu Trp Val Glu Phe Glu Leu Pro Glu
                165                 170                 175

Gly Asn Phe Ser Val Thr Met Thr Ile Asp Leu Met Asn Asn Ala Ile
                180                 185                 190

Ile Asp Asn Tyr Leu Ala Val Gly Arg Gln Asn Gly Val Leu Glu Ser
        195                 200                 205

Asp Ile Gly Val Lys Phe Asp Thr Arg Asn Phe Arg Leu Gly Trp Asp
        210                 215                 220

Pro Val Thr Glu Leu Val Met Pro Gly Val Tyr Thr Asn Glu Ala Phe
225                 230                 235                 240
```

```
His Pro Asp Ile Val Leu Leu Pro Gly Cys Gly Val Asp Phe Thr Glu
                245                 250                 255

Ser Arg Leu Ser Asn Leu Leu Gly Ile Arg Lys Arg Gln Pro Phe Gln
            260                 265                 270

Glu Gly Phe Gln Ile Met Tyr Glu Asp Leu Glu Gly Gly Asn Ile Pro
        275                 280                 285

Ala Leu Leu Asp Val Asp Ala Tyr Glu Lys Ser Lys Glu Asp Ala Ala
    290                 295                 300

Ala Glu Ala Thr Ala Ala Val Ala Thr Ala Ser Thr Glu Val Arg Gly
305                 310                 315                 320

Asp Asn Phe Ala Ser Ala Ala Val Ala Ala Glu Ala Ala Glu
                325                 330                 335

Thr Glu Ser Lys Ile Val Ile Gln Pro Val Glu Lys Asp Ser Lys Asn
                340                 345                 350

Arg Ser Tyr Asn Val Leu Pro Asp Lys Ile Asn Thr Ala Tyr Arg Ser
            355                 360                 365

Trp Tyr Leu Ala Tyr Asn Tyr Gly Asp Pro Glu Lys Gly Val Arg Ser
        370                 375                 380

Trp Thr Leu Leu Thr Thr Ser Asp Val Thr Cys Gly Val Glu Gln Val
385                 390                 395                 400

Tyr Trp Ser Leu Pro Asp Met Met Gln Asp Pro Val Thr Phe Arg Ser
                405                 410                 415

Thr Arg Gln Val Ser Asn Tyr Pro Val Val Gly Ala Glu Leu Leu Pro
            420                 425                 430

Val Tyr Ser Lys Ser Phe Phe Asn Glu Gln Ala Val Tyr Ser Gln Gln
        435                 440                 445

Leu Arg Ala Phe Thr Ser Leu Thr His Val Phe Asn Arg Phe Pro Glu
    450                 455                 460

Asn Gln Ile Leu Val Arg Pro Pro Ala Pro Thr Ile Thr Thr Val Ser
465                 470                 475                 480

Glu Asn Val Pro Ala Leu Thr Asp His Gly Thr Leu Pro Leu Arg Ser
                485                 490                 495

Ser Ile Arg Gly Val Gln Arg Val Thr Val Thr Asp Ala Arg Arg Arg
            500                 505                 510

Thr Cys Pro Tyr Val Tyr Lys Ala Leu Gly Ile Val Ala Pro Arg Val
        515                 520                 525

Leu Ser Ser Arg Thr Phe
    530

<210> SEQ ID NO 21
<211> LENGTH: 524
<212> TYPE: PRT
<213> ORGANISM: Rabies virus

<400> SEQUENCE: 21

Met Val Pro Gln Ala Leu Leu Phe Val Pro Leu Leu Val Phe Pro Leu
1               5                   10                  15

Cys Phe Gly Lys Phe Pro Ile Tyr Thr Ile Pro Asp Lys Leu Gly Pro
                20                  25                  30

Trp Ser Pro Ile Asp Ile His His Leu Ser Cys Pro Asn Asn Leu Val
            35                  40                  45

Val Glu Asp Glu Gly Cys Thr Asn Leu Ser Gly Phe Ser Tyr Met Glu
        50                  55                  60

Leu Lys Val Gly Tyr Ile Leu Ala Ile Lys Met Asn Gly Phe Thr Cys
65                  70                  75                  80
```

```
Thr Gly Val Val Thr Glu Ala Glu Thr Tyr Thr Asn Phe Val Gly Tyr
                85                  90                  95

Val Thr Thr Thr Phe Lys Arg Lys His Phe Arg Pro Thr Pro Asp Ala
                100                 105                 110

Cys Arg Ala Ala Tyr Asn Trp Lys Met Ala Gly Asp Pro Arg Tyr Glu
                115                 120                 125

Glu Ser Leu His Asn Pro Tyr Pro Asp Tyr Arg Trp Leu Arg Thr Val
        130                 135                 140

Lys Thr Thr Lys Glu Ser Leu Val Ile Ile Ser Pro Ser Val Ala Asp
145                 150                 155                 160

Leu Asp Pro Tyr Asp Arg Ser Leu His Ser Arg Val Phe Pro Ser Gly
                165                 170                 175

Lys Cys Ser Gly Val Ala Val Ser Ser Thr Tyr Cys Ser Thr Asn His
                180                 185                 190

Asp Tyr Thr Ile Trp Met Pro Glu Asn Pro Arg Leu Gly Met Ser Cys
                195                 200                 205

Asp Ile Phe Thr Asn Ser Arg Gly Lys Arg Ala Ser Lys Gly Ser Glu
        210                 215                 220

Thr Cys Gly Phe Val Asp Glu Arg Gly Leu Tyr Lys Ser Leu Lys Gly
225                 230                 235                 240

Ala Cys Lys Leu Lys Leu Cys Gly Val Leu Gly Leu Arg Leu Met Asp
                245                 250                 255

Gly Thr Trp Val Ala Met Gln Thr Ser Asn Glu Thr Lys Trp Cys Pro
                260                 265                 270

Pro Asp Gln Leu Val Asn Leu His Asp Phe Arg Ser Asp Glu Ile Glu
        275                 280                 285

His Leu Val Val Glu Glu Leu Val Arg Lys Arg Glu Glu Cys Leu Asp
        290                 295                 300

Ala Leu Glu Ser Ile Met Thr Thr Lys Ser Val Ser Phe Arg Arg Leu
305                 310                 315                 320

Ser His Leu Arg Lys Leu Val Pro Gly Phe Gly Lys Ala Tyr Thr Ile
                325                 330                 335

Phe Asn Lys Thr Leu Met Glu Ala Asp Ala His Tyr Lys Ser Val Arg
                340                 345                 350

Thr Trp Asn Glu Ile Leu Pro Ser Lys Gly Cys Leu Arg Val Gly Gly
                355                 360                 365

Arg Cys His Pro His Val Asn Gly Val Phe Phe Asn Gly Ile Ile Leu
        370                 375                 380

Gly Pro Asp Gly Asn Val Leu Ile Pro Glu Met Gln Ser Ser Leu Leu
385                 390                 395                 400

Gln Gln His Met Glu Leu Leu Glu Ser Ser Val Ile Pro Leu Val His
                405                 410                 415

Pro Leu Ala Asp Pro Ser Thr Val Phe Lys Asp Gly Asp Glu Ala Glu
                420                 425                 430

Asp Phe Val Glu Val His Leu Pro Asp Val His Asn Gln Val Ser Gly
        435                 440                 445

Val Asp Leu Gly Leu Pro Asn Trp Gly Lys Tyr Val Leu Leu Ser Ala
450                 455                 460

Gly Ala Leu Thr Ala Leu Met Leu Ile Ile Phe Leu Met Thr Cys Cys
465                 470                 475                 480

Arg Arg Val Asn Arg Ser Glu Pro Thr Gln His Asn Leu Arg Gly Thr
                485                 490                 495
```

```
Gly Arg Glu Val Ser Val Thr Pro Gln Ser Gly Lys Ile Ile Ser Ser
            500                 505                 510

Trp Glu Ser His Lys Ser Gly Gly Glu Thr Arg Leu
            515                 520
```

ADENOVIRAL VECTOR

The present invention relates to novel adenoviral vectors, immunogenic compositions thereof and their use in medicine.

All publications, patents and patent applications cited herein are incorporated in full by reference.

BACKGROUND

Traditionally, vaccines have been based on whole inactivated or attenuated pathogens. However, for many infectious diseases such as malaria, this approach is impractical and the focus of research has changed to the development of 'subunit vaccines' expressing only those pathogen-derived antigens that induce immune correlates of protection.

Subunit vaccines present an antigen to the immune system without introducing a whole infectious organism. One such method involves the administration of a specific, isolated protein from an infectious organism. However, this technique often induces only a weak immune response and the isolated proteins may have a different three-dimensional structure than the protein in its normal context, resulting in the production of antibodies that may not recognize the infectious organism.

An alternative method has therefore been developed which utilizes viral vectors for the delivery of antigens. Viruses are obligate intracellular parasites which replicate by transfecting their DNA into a host cell, and inducing the host cell to express the viral genome. This reproductive strategy has been harnessed to create vectored vaccines by creating recombinant, non-replicating viral vectors which carry one or more heterologous transgenes. Transfection or transduction of the recombinant viral genome into the host cell results in the expression of the heterologous transgene in the host cell. When the heterologous transgene encodes an antigen, for example, expression of the antigen within the host cell can elicit a protective or therapeutic immune response by the host immune system. As such, the viral vectors may function as effective vaccines. Alternatively, the heterologous transgene may encode a functional allele of a gene, expression of which can be used to counteract the effects of a deleterious mutant allele of the gene, in a process known as gene therapy.

Particularly suitable for use as viral vectors are adenoviruses. Adenoviruses are non-enveloped viruses, approximately 90-100 nm in diameter, comprising a nucleocapsid and a linear double stranded DNA genome. The viral nucleocapsid comprises penton and hexon capsomers. A unique fibre is associated with each penton base and aids in the attachment of the virus to the host cell via the Coxsackie-adenovirus receptor on the surface of the host cell. Over 50 serotype strains of adenoviruses have been identified, most of which cause respiratory tract infections, conjunctivitis and gastroentiritus in humans. Rather than integrating into the host genome, adenoviruses normally replicate as episomal elements in the nucleus of the host cell. The genome of adenoviruses comprises 4 early transcriptional units (E1, E2, E3 and E4), which have mainly regulatory functions and prepare the host cell for viral replication. The genome also comprises 5 late transcriptional units (L1, L2, L3, L4 and L5), which encode structural proteins including the penton (L2), the hexon (L3), the scaffolding protein (L4) and the fiber protein (L5), which are under the control of a single promoter. Each extremity of the genome comprises an Inverted Terminal Repeat (ITR) which is necessary for viral replication.

Recombinant adenoviruses were originally developed for gene therapy, but the strong and sustained transgene-specific immune responses elicited by these gene delivery agents prompted their use as vaccine carriers. In addition to being highly immunogenic, adenoviruses offer many other advantages for clinical vaccine development. The adenoviral genome is relatively small (between 26 and 45 kbp), well characterised and easy to manipulate. The deletion of a single transcriptional unit, E1, renders the virus replication-incompetent which increases its predictability and reduces side effects in clinical applications. Recombinant adenoviruses can accommodate relatively large transgenes, in some cases up to 8 kb, allowing flexibility in subunit design, and have a relatively broad tropism facilitating transgene delivery to a wide variety of cells and tissues. Importantly for clinical applications, methods for scaled-up production and purification of recombinant adenoviruses to high titre are well established. Thus far, subgroup C serotypes AdHu2 or AdHu5 have predominantly been used as vectors.

However, the first generation of vaccine vectors based on the archetypal human adenovirus AdHu5 showed poor efficacy in clinical trials, despite encouraging pre-clinical data[1]. It was subsequently discovered that a large proportion of human adults harbour significant titres of neutralising antibodies to common human serotypes such as AdHu2 and AdHu5, as a result of natural infection. Neutralising antibodies could reduce the potency of viral vector vaccines by blocking viral entry into host cells and hence delivery of the target transgene.

The occurrence of pre-existing anti-vector immunity is being addressed through the development of new adenoviral vectors based on serotypes to which the human population is less likely to have been exposed, including those of chimpanzee origin[2,3]. However, some such chimpanzee adenoviral vectors have limited efficacy on the grounds of unexplained immunity in human populations, varying levels of cross-reactivity with human adenoviruses, and sub-optimal growth in transformed cell lines. In addition, it is advantageous to have a range of different adenoviral vectors available for use in immunising against different diseases, on the grounds that induction of neutralising antibodies against a vector may prevent its re-administration for another indication.

WO2012/172277 describes an adenovirus vector derived from chimpanzee adenovirus AdY25, which addresses some of the above-described problems in the art. This vector is termed ChAdOx1.

However, there continues to be a need in the art for highly immunogenic, non-human adenoviral vectors which effectively deliver the target transgene, minimize the effect of pre-existing immunity to adenovirus serotypes and replicate efficiently in transformed cell lines.

SUMMARY OF INVENTION

In a first aspect, the present invention provides an adenoviral vector comprising the genome of an adenovirus other than AdHu5 and AdY25, wherein the genome of the adenovirus has been modified such that the vector lacks the native E4 locus of the adenovirus and comprises heterologous E4Orf1, E4Orf2 and E4Orf3 coding regions from AdY25.

In a preferred embodiment, the adenoviral vector further comprises heterologous E4Orf4, E4Orf6 and E4Orf6/7 coding regions from AdHu5 in the E4 locus of the adenovirus.

In a preferred embodiment, said adenovirus is C68.

In a preferred embodiment, said adenoviral vector lacks a functional E1 locus and/or lacks an E3 locus.

In a second aspect, the present invention provides an immunogenic composition comprising the adenovirus vector according to the first aspect of the invention and, optionally, one or more additional active ingredients, a pharmaceutically acceptable carrier, diluent, excipient or adjuvant.

Preferably the adjuvant is an oil-in-water adjuvant. For example the adjuvant may comprise squalene. Preferably the adjuvant is selected from MF59®, AS03, AF03 or Addavax.

A third aspect provides the use of the adenoviral vector according to the first aspect or the immunogenic composition according to the second aspect in medicine. In particular, the adenoviral vector and immunogenic compositions are provided for delivery of a transgene into a host cell, elicitation of an immune response in an animal, boosting an immune response in an animal, treating or preventing at least one disease, inducing an immune response in an animal that will break tolerance to a self-antigen and gene therapy.

A fourth aspect provides a polynucleotide sequence encoding the adenoviral vector according to the first aspect of the present invention.

A fifth aspect of the present invention provides a host cell transduced with the viral vector according to the first aspect of the present invention.

A sixth aspect of the present invention provides a method of producing the viral vector according to the first aspect of the present invention by incorporating the polynucleotide sequence according to the fourth aspect into a Bacterial Artificial Chromosome (BAC).

A seventh aspect of the present invention provides a Bacterial Artificial Chromosome (BAC) clone comprising the polynucleotide sequence according to the fourth aspect of the present invention.

An eighth aspect of the present invention provides a packaging cell line producing the viral vector according to the first aspect of the present invention.

FIGURES

The present invention is described with reference to the following figures:

FIG. 1. Generation of a molecular clone of chimpanzee adenovirus 68 (ChAd68). a) Insertion of ChAd68 genomic DNA into the pBAC 'rescue vector' by gap repair. The E1 left flanking regions 1 (LF1) and 2 (LF2) and terminal right hand side region (RF) are amplified from Chad68 genomic DNA and cloned into pBACe3.6 to produce a BAC adenovirus rescue clone. Recombination occurs between LF1 and LF2 of the isolated ChAd68 genome and the BAC rescue clone and the RF of ChAd68 genome and the BAC rescue clone. The resulting product is a BAC containing an E1 deleted ChAd68 genome. b) Excision of the E3 region of ChAd68 by recombineering. Firstly, the galactokinase gene (GalK) is amplified from pGalK using primers containing sequences homologous to the flanking region of E3 (E3LF and E3RF). The E3 region is replaced by the GalK gene using A red recombination. The GalK gene is subsequently replaced by a PCR product consisting of E3LF and E3RF, again using A red recombination. The resulting product is a BAC containing an E1E3 deleted ChAd68 genome. c) Insertion of an antigen cassette at the E1 locus. Firstly, the galactokinase gene (GalK) is amplified from pGalK using primers containing sequences homologous to the flanking region of E1 (LF1 and LF2). The E1 region is replaced by the GalK gene using A red recombination. The GalK gene is subsequently replaced by a PCR product consisting of LF1-antigen expression cassette-LF2 using A red recombination. The resulting product is a BAC containing an E1E3 deleted ChAd68 genome with an antigen expression cassette at the E1 locus.

FIG. 2. Insertion of an antigen expression cassette into adenovirus vector using att recombination sites. A universal cassette expressing a bacteria antibiotic resistance gene and ccdB suicide gene flanked by the specific recombination sequences, attR1 and attR2 is located at the E1 locus and/or the E3 locus of the BAC-adenovirus genome clone. Shuttle plasmids containing an antigen expression cassette flanked by specific recombination sites paired with those present in the genome (attL1/L2) allow site specific recombination in the presence of an enzyme mixture containing bacteriophage λ integrase, integration host factor and excisionase.

FIG. 3. Growth of ChAdOx2 compared to ChAd68. E1 complementing Human embryonic kidney 293 cells were infected with a multiplicity of infection (MOI) of 1 virus vector per cell. Samples were taken at 48 and 96 hours post infection. Virus yield was determined by titration in triplicate on HEK293 cells and GFP positive cells counted 48 hours post infection. Results are expressed as the mean $Log_{10}$ fluorescent units (FU) per ml from two separate experiments with standard deviation depicted.

FIG. 4. Immunogenicity of ChAdOx1-eGFP compared to ChAdOx2-eGFP. Female BALB/c mice (4 per group) were injected intramuscularly with $10^8$ infectious units of vector and spleens harvested 2 weeks later to measure the response to GFP by interferon-gamma enyzyme-linked immunosorbent spot (IFN-γ ELISPOT). Results are expressed as spot-forming units (SFUs) per million splenocytes. Mann-Whitney test was used to statistically analyse the results and the Mean with SEM is depicted.

FIG. 5. The study groups (table 1) and current progress of enrollment (table 2) of a phase I clinical trial to determine the safety and immunogenicity of the candidate *Mycobacterium avium* subspecies paratuberculosis (MAP) vaccine ChAdOx2 HAV in healthy adult volunteers.

FIGS. 6 to 11. The proportions of volunteers presenting adverse events (AEs) at different dose groups in the phase I clinical trial investigating the candidate *Mycobacterium avium* subspecies paratuberculosis (MAP) vaccine ChAdOx2 HAV in healthy adult volunteers. Dose of $5 \times 10^9$ vp for FIGS. 6 and 7 and a dose of $2.5 \times 10^{10}$ vp for FIGS. 8, 9, 10 and 11.

FIG. 12. Median summed response to all pools of antigens in the HAV vaccine stratified by dose. * p=0.01 Kruskall-Wallis test, with Dunn's multiple comparison test for the $2.5 \times 10^{10}$ dose group. Lines represent medians.

FIG. 13 shows the tabulated responses for each individual at day 0, day 28 and day 56 in participants immunised with different dosages of the HAV vaccine.

Figure 16:
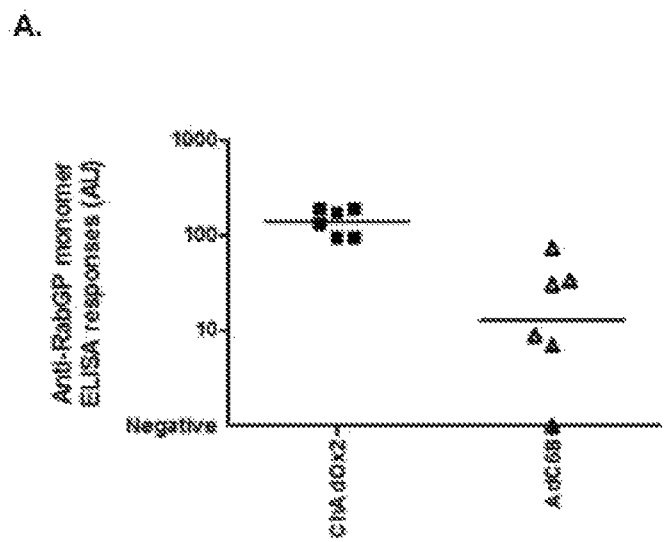

FIG. 16 shows the high immunogenicity of the ChAdOx2 RabGP vaccine construct. p=0.005 comparing ELISA responses (measured in arbitrary antibody units [AU]) by Mann-Whitney test. Immunogenicity of ChAdOx2-RabGP compares favourably to that of AdC68. CD-1 outbred mice were vaccinated intramuscularly with 107 infectious units of either ChAdOx2 or AdC68 expressing rabies glycoprotein. Serum was collected 4 weeks after vaccination. Antibody responses were assessed by ELISA against recombinant rabies glycoprotein, and the result shown in graph A and table B.

DETAILED DESCRIPTION

The present invention relates to novel adenoviral vectors derived from an adenovirus other than AdHu5 and AdY25, immunogenic compositions thereof and their use in medicine.

The invention provides an adenoviral vector comprising the genome of an adenovirus other than AdHu5 and AdY25, wherein the genome of the adenovirus has been modified such that the vector lacks the native E4 locus of the adenovirus and comprises heterologous E4Orf1, E4Orf2, and E4Orf3 coding regions from AdY25.

The adenovirus E4 region comprises at least six Open Reading Frames (ORFs or Orfs). Preferably, the native E4 locus of the adenovirus is deleted.

In a preferred embodiment, the adenovirus is a chimpanzee adenovirus, C68 (also known as C9, Pan6 and sAd25). The nucleotide sequence of C68 is provided as SEQ ID NO. 1. The complete genome of simian adenovirus 25 (i.e. C68) has been deposited and assigned GenBank accession number AC_000011.

According to the invention, the genome of the adenovirus has been modified such that the vector lacks the native E4 locus of the adenovirus. The E4 region of C68 is provided herein as SEQ ID NO. 2.

Furthermore, according to the invention, the genome of the adenovirus is modified such that the vector and comprises heterologous E4Orf1, E4Orf2, and E4Orf3 coding regions from AdY25. AdY25 is a chimpanzee adenovirus described in detail in WO2012/172277.

The complete nucleotide sequence of AdY25 is provided in SEQ ID NO. 6.

The amino acid sequence of E4Orf1 from AdY25 is provided herein as SEQ ID NO. 3. The corresponding nucleotide sequence is nucleotides 35930 to 36304 of SEQ ID NO. 6.

The amino acid sequence of E4Orf2 from AdY25 is provided herein as SEQ ID NO. 4. The corresponding nucleotide sequence is nucleotides 35491 to 35880 of SEQ ID NO. 6.

The amino acid sequence of E4Orf3 from AdY25 is provided herein as SEQ ID NO. 5. The corresponding nucleotide sequence is nucleotides 35141 to 35494 of SEQ ID NO. 6.

In a preferred embodiment, the adenoviral vector further comprises heterologous E4Orf4, E4Orf6, and E4Orf6/7 coding regions from AdHu5.

AdHu5 is human serotype 5 adenovirus. The amino acid sequence of E4Orf4 from AdHu5 is provided herein as SEQ ID NO. 7. The amino acid sequence of E4Orf6 from AdHu5 is provided herein as SEQ ID NO. 8. The amino acid sequence of E4Orf6/7 from AdHu5 is provided herein as SEQ ID NO. 9.

As the skilled person will be aware, adenoviral vectors based on the adenovirus C68 are referred to in the art by various names, including AdCh68, AdC68, ChAd68 and sAdV25 (see, for example, Abbink et al., J Virol. 2015 February; 89(3):1512-22 (PubMed ID: 25410856) and Jeyanathan et al., Mucosal Immunol. 2015 November; 8(6): 1373-87 (PubMed ID: 25872483). These names are also used interchangeably herein.

The vector of the present invention preferably comprises a capsid derived from chimpanzee adenovirus C68. Preferably, the capsid comprises the native or wild-type C68 capsid proteins, including penton proteins, hexon proteins, fibre proteins and/or scaffolding proteins. However, one of skill in the art will readily appreciate that small modifications can be made to the capsid proteins without adversely altering vector tropism.

In a particularly preferred embodiment, the vector capsid comprises one or more capsid proteins selected from the group consisting of:
(a) a hexon protein encoded by the coding sequence corresponding to nucleotides 18315 to 21116 of SEQ ID NO. 1 or a sequence substantially identical thereto;
(b) a penton protein encoded by the coding sequence corresponding to nucleotides 13884 to 15488 of SEQ ID NO. 1, or a sequence substantially identical thereto; and
(c) a fibre protein encoded by the coding sequence corresponding to nucleotides 32134 to 33411 of SEQ ID NO. 1, or a sequence substantially identical thereto.

Preferably, the hexon protein comprises the amino acid sequence of SEQ ID NO. 18, or an amino acid sequence substantially identical to SEQ ID NO. 18.

Preferably, the penton protein comprises the amino acid sequence of SEQ ID NO. 19, or an amino acid sequence substantially identical to SEQ ID NO. 19.

Preferably, the fiber protein comprises the amino acid sequence of SEQ ID NO. 20, or an amino acid sequence substantially identical to SEQ ID NO. 20.

The adenoviral vector of the present invention may comprise one of the hexon, penton and fibre proteins as described above, any combination of two of said proteins, or all three of said proteins.

The adenoviral vector of the invention is referred to herein as ChAdOx2. The nucleotide sequence of the ChAdOx2 vector (with a Gateway™ cassette in the E1 locus) is shown in SEQ ID NO. 10.

The person skilled in the art will appreciate that there are homologues, equivalents and derivatives of all of the nucleic acid sequences described herein. Thus, the invention also encompasses nucleic acid molecules having a sequence substantially identical to the nucleic acid sequences described herein over their entire length.

One of skill in the art will appreciate that the present invention can also include variants of those particular nucleic acid molecules which are exemplified herein. These may occur in nature, for example because of strain variation. For example, additions, substitutions and/or deletions are included. One of skill in the art will also appreciate that variation from the particular nucleic acid molecules exemplified herein will be possible in view of the degeneracy of the genetic code. Preferably, the variants have substantial identity to the nucleic acid sequences described herein over their entire length.

As used herein, nucleic acid sequences which have "substantial identity" preferably have at least 80%, 90%, 91%, 92%, 93%, 94%, 95% 96%, 97%, 98%, 98.1%, 98.2%, 98.3%, 98.4%, 98.5%, 98.6%, 98.7%, 98.8%, 98.9%, 99%, 99.1%, 99.2%, 99.3%, 99.4% 99.5%, 99.6%, 99.7%, 99.8% or 99.9% identity with said sequences.

Desirably, the term "substantial identity" indicates that said sequence has a greater degree of identity with any of the sequences described herein than with prior art nucleic acid sequences.

When comparing nucleic acid sequences for the purposes of determining the degree of homology or identity one can use programs such as BESTFIT and GAP (both from the Wisconsin Genetics Computer Group (GCG) software package). BESTFIT, for example, compares two sequences and produces an optimal alignment of the most similar segments. GAP enables sequences to be aligned along their whole length and finds the optimal alignment by inserting spaces in either sequence as appropriate. Suitably, in the context of the present invention, when discussing identity of nucleic acid sequences, the comparison is made by alignment of the sequences along their whole length. The above applied mutatis mutandis to all nucleic acid sequences disclosed in the present application.

References herein to "nucleic acid" can be DNA, including cDNA, RNA including mRNA or PNA (peptide nucleic acid) or a mixture thereof.

Merely for the convenience of those of skill in the art, a sample of E. coli strain Stellar containing bacterial artificial chromosomes (BACs) containing the ChAdOx2-GFP was deposited by Isis Innovation Limited on 13 Jun. 2016 with the European Collection of Cell Cultures (ECACC) at the Health Protection Agency Culture Collections, Health Protection Agency, Porton Down, Salisbury SP4 0JG, United Kingdom under the Budapest Treaty and designated by provisional accession no. 16061301.

The E. coli containing the BAC is a class I genetically modified organism. The genotype of E. coli strain Stellar is: F-, endA1, supE44, thi-1, recA1, relA1, gyrA96, phoA, Φ80d lacZΔ M15, Δ (lacZYA-argF) U169, Δ (mrr-hsdRMS-mcrBC), ΔmcrA, λ-. Chimpanzee adenovirus ChAd68 is provisionally classified within the species Human adenovirus E based on the nucleotide sequence of the viral DNA polymerase.

The BAC propagates within the bacteria during replication and can be maintained by selection with chloramphenicol. The E. coli strain Stellar containing the BAC into which the genome is cloned can be propagated in Luria-Bertani broth or agar containing 12.5 µg/mL chloramphenicol at 37° C.

Converting the BAC clones of the viral genomes into viruses ("rescue") can be carried out by the following steps. The E. coli host is propagated and the BAC DNA is purified from the bacteria according to standard methods. The DNA is linearised with the restriction endonuclease PacI and transfected into HEK293 cells (or a similar E1 complementing cell line). The resulting adenovirus can then be propagated and purified for use as a vaccine for example. All of these reagents and cells are publicly available. If the deposition were rescued, the resulting virus would be a class I genetically modified organism.

As used herein, the phrase "viral vector" refers to a recombinant virus or a derivative thereof which is capable of introducing genetic material, including recombinant DNA, into a host cell or host organism by means of transduction or non-productive infection. For example, the vector of the present invention may be a gene delivery vector, a vaccine vector, an antisense delivery vector or a gene therapy vector.

As used herein, "C68" refers to the chimpanzee adenovirus 68 or subunits derived therefrom, and the term "ChAd68" refers to vectors derived therefrom or based thereon.

Shorthand terms are used to indicate modifications made to the wildtype virus. For example, "ΔE1" or "delE1" indicates deletion or functional deletion of the E1 locus. The phrase "Ad5E4Orf6" indicates that the viral vector comprises heterologous E4 open reading frame 6 from the Ad5 virus.

One of skill in the art will appreciate that the present invention can include variants of those particular amino acid sequences which are exemplified herein. Particularly preferred are variants having an amino acid sequence similar to that of the parent protein, in which one or more amino acid residues are substituted, deleted or added in any combination. Especially preferred are silent substitutions, additions and deletions, which do not alter the properties and activities of the protein of the present invention. Various amino acids have similar properties, and one or more such amino acids of a substance can often be substituted by one or more other such amino acids without eliminating a desired activity of that substance. Thus, the amino acids glycine, alanine, valine, leucine and isoleucine can often be substituted for one another (amino acids having aliphatic side chains). Of these possible substitutions it is preferred that glycine and alanine are used to substitute for one another (since they have relatively short side chains) and that valine, leucine and isoleucine are used to substitute for one another (since they have larger aliphatic side chains which are hydrophobic). Other amino acids which can often be substituted for one another include: phenylalanine, tyrosine and tryptophan (amino acids having aromatic side chains); lysine, arginine and histidine (amino acids having basic side chains); aspartate and glutamate (amino acids having acidic side chains); asparagine and glutamine (amino acids having amide side chains); and cysteine and methionine (amino acids having sulphur containing side chains). Variants include naturally occurring and artificial variants. Artificial variants may be generated using mutagenesis techniques, including those applied to nucleic acid molecules, cells or organisms. Preferably, the variants have substantial identity to the amino acid sequences exemplified herein.

As used herein, amino acid sequences which have "substantial identity" preferably have at least 80%, 90%, 91%, 92%, 93%, 94%, 95% 96%, 97%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8% or 99.9% identity with said sequences. Desirably, the term "substantial identity" indicates that said sequence has a greater degree of identity with any of the sequences described herein than with prior art amino acid sequences.

One can use a program such as the CLUSTAL program to compare amino acid sequences. This program compares amino acid sequences and finds the optimal alignment by inserting spaces in either sequence as appropriate. It is possible to calculate amino acid identity or similarity (identity plus conservation of amino acid type) for an optimal alignment. A program like BLASTx will align the longest stretch of similar sequences and assign a value to the fit. It is thus possible to obtain a comparison where several regions of similarity are found, each having a different score. The above applied mutatis mutandis to all amino acid sequences disclosed in the present application.

The vector of the present invention also preferably comprises an exogenous nucleotide sequence. Preferably, the exogenous nucleotide sequence is operably linked to expression control sequences which direct the translation, transcription and/or expression thereof in an animal cell and an adenoviral packaging signal sequence.

Preferably, the exogenous nucleotide sequence encodes a molecule of interest. The molecule of interest may be a protein, polypeptide or nucleic acid molecule of interest. The exogenous nucleotide sequence may encode one or more, two or more or three or more molecules of interest.

Proteins and polypeptides of interest include antigens, molecular adjuvants, immunostimulatory proteins and recombinases.

Preferably the antigen is a pathogen-derived antigen. Preferably the pathogen is selected from the group consisting of M. tuberculosis, Plasmodium sp, influenza virus, HIV, Hepatitis C virus, Cytomegalovirus, Human papilloma virus, rabies virus, measles virus, mumps, rubella, zika virus, leishmania parasites or any mycobacterial species. Preferably the antigen is selected from TRAP, MSP-1, AMA-1 and CSP from *Plasmodium*, influenza virus antigens, or ESAT6, TB10.4 85A and 85B antigens from *Mycobacterium tuberculosis*. More preferably, the antigen may be Ag85A from *Mycobacterium tuberculosis*. The antigen may be nucleoprotein (NP) and/or matrix protein 1 (M1) from influenza A virus.

More preferably the antigen is from *Mycobacterium avium* subspecies paratuberculosis (MAP) or the antigen is rabies virus glycoprotein.

Preferably, the protein or polypeptide of interest is an antigen. In one embodiment, the antigen is a pathogen-derived antigen. Preferably, the pathogen is selected from the group consisting of bacteria, viruses, prions, fungi, protists and helminths. Preferably, the antigen is derived from the group consisting of *M. tuberculosis, Plasmodium* sp, influenza virus, HIV, Hepatitis C virus, Cytomegalovirus, Human papilloma virus, rabies virus, measles virus, mumps, rubella, zika virus, malaria parasites, leishmania parasites or any mycobacterial species. Preferred antigens include TRAP, MSP-1, AMA-1 and CSP from *Plasmodium*, influenza virus antigens and ESAT6, TB10.4 85A and 85B antigens from *Mycobacterium tuberculosis*.

Particularly preferred antigens include Ag85A from *Mycobacterium tuberculosis* and nucleoprotein (NP) and matrix protein 1 (M1) from influenza A virus, preferably Influenza A virus.

The nucleic acid sequence of *Mycobacterium tuberculosis* protein Ag85A is shown in SEQ ID NO. 11 and the amino acid sequence is shown in SEQ ID NO. 12. The nucleic acid sequence of nucleoprotein (NP) and matrix protein 1 (M1) from influenza A virus is shown in SEQ ID NO. 13 and the amino acid sequence is shown in SEQ ID NO. 14.

In a preferred embodiment, the vaccine contains antigens from *Mycobacterium avium* subspecies paratuberculosis (MAP) which is the causative agent for Johne's disease in cattle and has been linked to Crohn's disease in humans.

In another preferred embodiment, the exogenous nucleotide sequence encodes the rabies virus glycoprotein, preferably the ERA strain.

In an alternative embodiment, the antigen is a self-antigen. Suitable self-antigens include antigens expressed by tumour cells which allow the immune system to differentiate between tumour cells and other cell types. Suitable self-antigens include antigens that are either inappropriate for the cell type and/or its environment, or are only normally present during the organisms' development (e.g. foetal antigens). For example, GD2 is normally only expressed at a significant level on the outer surface membranes of neuronal cells, where its exposure to the immune system is limited by the blood-brain barrier. However, GD2 is expressed on the surfaces of a wide range of tumour cells including small-cell lung cancer, neuroblastoma, melanomas and osteosarcomas. Other suitable self-antigens include cell-surface receptors that are found on tumour cells but are rare or absent on the surface of healthy cells. Such receptors may be responsible for activating cellular signalling pathways that result in the unregulated growth and division of the tumour cell. For example, ErbB2 is produced at abnormally high levels on the surface of breast cancer tumour cells. Preferably, the self antigen comprises a tumour-associated antigen (TAA).

As used herein, the term 'antigen' encompasses one or more epitopes from an antigen and includes the parent antigen, and fragments and variants thereof. These fragments and variants retain essentially the same biological activity or function as the parent antigen. Preferably, they retain or improve upon the antigenicity and/or immunogenicity of the parent antigen. Generally, "antigenic" is taken to mean that the protein or polypeptide is capable of being used to raise antibodies or T cells or indeed is capable of inducing an antibody or T cell response in a subject. "Immunogenic" is taken to mean that the protein or polypeptide is capable of eliciting a potent and preferably a protective immune response in a subject. Thus, in the latter case, the protein or polypeptide may be capable of generating an antibody response and a non-antibody based immune response.

Preferably, fragments of the antigens comprise at least n consecutive amino acids from the sequence of the parent antigen, wherein n is preferably at least, or more than, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 57, 58, 59, 60, 70, 80, 90 or 100. The fragments preferably include one or more epitopic regions from the parent antigen. Indeed, the fragment may comprise or consist of an epitope from the parent antigen. Alternatively, the fragment may be sufficiently similar to such regions to retain their antigenic/immunogenic properties.

The antigens of the present invention include variants such as derivatives, analogues, homologues or functional equivalents of the parent antigen. Particularly preferred are derivatives, analogues, homologues or functional equivalents having an amino acid sequence similar to that of the parent antigen, in which one or more amino acid residues are substituted, deleted or added in any combination.

Preferably, these variants retain an antigenic determinant or epitope in common with the parent antigen.

Preferably, the derivatives, analogues, homologues, and functional equivalents have an amino acid sequence substantially identical to amino acid sequence of the parent antigen.

The exogeneous nucleotide sequence may encode more than one antigen. The viral vector may be designed to express the one or more antigen genes as an epitope string. Preferably, the epitopes in a string of multiple epitopes are linked together without intervening sequences such that unnecessary nucleic acid and/or amino acid material is avoided. The creation of the epitope string is preferably achieved using a recombinant DNA construct that encodes the amino acid sequence of the epitope string, with the DNA encoding the one or more epitopes in the same reading frame. An exemplary antigen, TIPeGFP, comprises an epitope string which includes the following epitopes: E6FP, SIV-gag, PyCD4 and Py3. Alternatively, the antigens may be expressed as separate polypeptides.

One or more of the antigens or antigen genes may be truncated at the C-terminus and/or the N-terminus. This may facilitate cloning and construction of the vectored vaccine and/or enhance the immunogenicity or antigenicity of the antigen. Methods for truncation will be known to those of skill in the art. For example, various well-known techniques of genetic engineering can be used to selectively delete the encoding nucleic acid sequence at either end of the antigen gene, and then insert the desired coding sequence into the viral vector. For example, truncations of the candidate protein are created using 3' and/or 5' exonuclease strategies selectively to erode the 3' and/or 5' ends of the encoding nucleic acid, respectively. Preferably, the wild type gene sequence is truncated such that the expressed antigen is truncated by 1, 2, 3, 4, 5, 6, 7, 8, 9, 10, 11, 12, 13, 14, 15, 16, 17, 18, 19, 20 or more amino acids relative to the parent antigen. Preferably, the antigen gene is truncated by 10-20 amino acids at the C-terminus relative to the wild type antigen. More preferably, the antigen gene is truncated by 13-18 amino acids, most preferably by 15 amino acids at the C-terminus relative to the wild type antigen. Preferably, the Ag85A antigen is C-terminally truncated in this manner.

One or more of the antigen genes may also comprise a leader sequence. The leader sequence may affect processing of the primary transcript to mRNA, translation efficiency, mRNA stability, and may enhance expression and/or immunogenicity of the antigen. Preferably, the leader sequence is tissue plasminogen activator (tPA). Preferably, the tPA leader sequence is positioned N-terminal to the one or more antigens.

The leader sequence such as the tPA leaders sequence may be linked to the sequence of the antigen via a peptide linker. Peptide linkers are generally from 2 to about 50 amino acids in length, and can have any sequence, provided that it does not form a secondary structure that would interfere with domain folding of the fusion protein.

One or more of the antigen genes may comprise a marker such as the Green Fluorescent Protein (GFP) marker to facilitate detection of the expressed product of the inserted gene sequence.

One or more of the antigen genes may comprise a nucleic acid sequence encoding a tag polypeptide that is covalently linked to the antigen upon translation. Preferably the tag polypeptide is selected from the group consisting of a PK tag, a FLAG tag, a MYC tag, a polyhistidine tag or any tag that can be detected by a monoclonal antibody. The nucleic acid sequence encoding the tag polypeptide may be positioned such that, following translation, the tag is located at the C-terminus or the N-terminus of the expressed antigen or may be internal to the expressed antigen. Preferably, the tag is located at the C-terminus of the expressed antigen. In a preferred embodiment, one or more of the antigen genes encode a PK tag. A tag of this type may facilitate detection of antigen expression and clones expressing the antigen, and/or enhance the immunogenicity or antigenicity of the antigen.

If a tag polypeptide is used, nucleotides encoding a linker sequence are preferably inserted between the nucleic acid encoding the tag polypeptide and the nucleic acid encoding the expressed antigen. An exemplary linker is IPNPLLGLD (SEQ ID NO.15).

In an alternative embodiment, the exogeneous sequence of interest may be non-protein encoding. For example, the exogeneous nucleotide sequence may be an miRNA or immunostimulatory RNA sequence.

The adenoviral vector may comprise one or more exogeneous nucleotide sequences, for example 1, 2 or 3 or more exogeneous nucleotide sequences. Preferably, each exogeneous nucleotide sequence embodies a transgene. The exogeneous nucleotide sequence embodying the transgene can be a gene or a functional part of the gene. The adenoviral vector may comprise one nucleotide sequence encoding a single molecule of interest. Alternatively, the adenoviral vector may comprise one nucleotide sequence or more than one nucleotide sequence encoding more than one molecule of interest.

Preferably, the exogeneous nucleotide sequence is located within the genome of the adenovirus, i.e. in a nucleic acid molecule that contains other adenoviral sequences. The exogeneous nucleotide sequence may be inserted into the site of a partially or fully deleted gene, for example into the site of an E1 deletion or an E3 deletion within the adenovirus genome.

The exogeneous nucleotide sequence may be inserted into an existing C68 gene region to disrupt the function of that region. Alternatively, the exogeneous nucleotide sequence may be inserted into a region of the genome with no alteration to the function or sequence of the surrounding genes.

The exogeneous nucleotide sequence or transgene is preferably operably linked to regulatory sequences necessary to drive translation, transcription and/or expression of the exogeneous nucleotide sequence/transgene in a host cell, for example a mammalian cell. As used herein, the phrase "operably linked" means that the regulatory sequences are contiguous with the nucleic acid sequences they regulate or that said regulatory sequences act in trans, or at a distance, to control the regulated nucleic acid sequence. Such regulatory sequences include appropriate expression control sequences such as transcription initiation, termination, enhancer and promoter sequences, efficient RNA processing signals, such as splicing and polyadenylation signals, sequences that enhance translation efficiency and protein stability and sequences promote protein secretion. Additionally they may contain sequences for repression of transgene expression, for example during production in cell lines expression a trans-activating receptor. Promoters and other regulatory sequences which control expression of a nucleic acid have been identified and are known in the art. Preferably, the promoter is selected from the group consisting of human CMV promoters, simian CMV promoters, murine CMV promoters, ubiquitin, the EF1 promoter, frog EF1 promoter, actin and other mammalian promoters. Most preferred are human CMV promoters and in particular the human CMV major immediate early promoter.

The exogeneous nucleotide sequence(s) of interest may be introduced into the viral vector as part of a cassette. As used herein, the term "cassette" refers to a nucleic acid molecule comprising at least one nucleotide sequence to be expressed, along with its transcriptional and translational control sequences to allow the expression of the nucleotide sequence(s) in a host cell, and optionally restriction sites at the 5' and 3' ends of the cassette. Because of the restriction endonuclease sites, the cassettes can easily be inserted, removed or replaced with another cassette. Changing the cassette will result in the expression of different sequence(s) by the vector into which the cassette is incorporated. Alternatively, any method known to one of skill in the art could be used to construct, modify or derive said cassette, for example PCR mutagenesis, In-Fusion®, recombineering, Gateway® cloning, site-specific recombination or topoisomerase cloning.

The expression control sequences preferably include the adenovirus elements necessary for replication and virion encapsidation. Preferably, the elements flank the exogeneous nucleotide sequence. Preferably, the ChAd68 vector comprises the 5' inverted terminal repeat (ITR) sequences of C68, which function as origins of replication, and 3' ITR sequences.

The packaging signal sequence functions to direct the assembly of the viral vector, and are well characterised and understood in the art.

As one of skill in the art will appreciate, there are minimum and maximum constraints upon the length of the nucleic acid molecule that can be encapsidated in the viral vector. Therefore, if required, the nucleic acid molecule may also comprise "stuffing", i.e. extra nucleotide sequence to bring the final vector genome up to the required size. Preferably, the nucleic acid molecule comprises sufficient "stuffing" to ensure that the nucleic acid molecule is about 80% to about 108% of the length of the wild-type nucleic acid molecule.

The nucleic acid molecule may also comprise one or more genes or loci from the C68 genome. The wild-type C68 genome comprises 4 early transcriptional units (E1, E2, E3 and E4), which have mainly regulatory functions and prepare the host cell for viral replication. The genome also comprises 5 late transcriptional units (L1, L2, L3, L4 and L5), which encode structural proteins including the penton (L2), the hexon (L3), the scaffolding protein (L4) and the fiber protein (L5), which are under the control of a single promoter. Each extremity of the genome comprises an Inverted Terminal Repeat (ITR) which is necessary for viral replication.

The viral vector of the present invention may be based on the complete native C68 genome, from which the native E4 region has been deleted and into which the heterologous E4Orf1, E4Orf2 and E4Orf3 coding regions from AdY25 have been inserted.

The native E4 region of C68 is provided herein as SEQ ID NO. 2.

An exogenous nucleotide sequence of interest may also be inserted into the C68 genome. One of skill in the art will appreciate that various additional modifications to the native C68 genome are possible, and indeed desirable, when creating a viral vector.

One or more native C68 genes may be deleted, functionally deleted or modified to optimise the viral vector.

As used herein, the phrase "deleted" refers to total deletion of a gene, whilst "functional deletion" refers to a partial deletion of a gene/locus, or some other modification such as a frame shift mutation, which destroys the ability of the adenovirus to express the gene/locus or renders the gene product non-functional.

The C68 genome may be modified to increase the insert capacity or hinder replication in host cells and/or increase growth and yield of the viral vector in transformed packaging cell lines. One of skill in the art will appreciate that any number of early or late genes can be functionally deleted. Replication of such modified viral vectors will still be possible in transformed cell lines which comprise a complement of the deleted genes. For example, the viral proteins necessary for replication and assembly can be provided in trans by engineered packaging cell lines or by a helper virus.

Therefore, in addition to the exogenous nucleotide sequence, the vector of the present invention may comprise the minimal adenoviral sequences, the adenoviral genome with one or more deletions or functional deletions of particular genes, or the complete native adenoviral genome, into which has been inserted the exogenous nucleotide sequence.

Preferably, one or more of the early transcriptional units are modified, deleted or functionally deleted.

In one embodiment, the viral vector is non-replicating or replication-impaired. As used herein, the term "non-replicating" or "replication-impaired" means not capable of replicating to any significant extent in the majority of normal mammalian cells, preferably normal human cells. It is preferred that the viral vector is incapable of causing a productive infection or disease in the human patient. However, the viral vector is preferably capable of stimulating an immune response. Viruses which are non-replicating or replication-impaired may have become so naturally, i.e. they may be isolated as such from nature. Alternatively, the viruses may be rendered non-replicating or replication-impaired artificially, e.g. by breeding in vitro or by genetic manipulation. For example, a gene which is critical for replication may be functionally deleted.

Preferably, the adenoviral vector replication is rendered incompetent by functional deletion of a single transcriptional unit which is essential for viral replication. Preferably, the E1 gene/locus is deleted or functionally deleted. The E1 gene/locus may be replaced with a heterologous transgene, for example a nucleotide sequence or expression cassette encoding a protein or polypeptide of interest.

The native E1 region of C68 is provided herein as SEQ ID NO. 16.

As discussed herein, the recombinant adenovirus may be created by generating a molecular clone of C68 in a Bacterial Artificial Chromosome (BAC), and the E1 locus is preferably deleted by including an extra homology flank downstream of the adenovirus E1 region to enable simultaneous deletion of E1 during homologous recombination between the C68 viral DNA and a linearised BAC "rescue vector".

Preferably, the viral vector according to the present invention comprises one or more recombination sites to enable the insertion of one or more transgenes or cassettes comprising the exogenous nucleotide sequence. Preferably, the recombination sites comprise phage lambda site specific recombination sites. These recombination sites may be introduced at any suitable locus, but are preferably introduced at the adenovirusE1 locus. Thus, the non-replicating or replication-impaired vector may be prepared by replacing the E1 gene with a nucleotide sequence encoding the protein or polypeptide of interest. Preferably, the recombination sites attR1 and attR2 are introduced at the adenovirusE1 locus as part of an Invitrogen Gateway® destination cassette.

Preferably, the vector lacks an adenovirus E3 gene/locus. Deletion of the adenovirus E3 region increases the insert capacity of the new vector by approximately 5 kb. Deletion of E3 has little consequence to viral vector yield since this region is not required for virus replication and therefore does not need to be provided in trans in the packaging cell line. The E3 locus may be deleted using GalK recombineering.

The native E3 region of C68 is provided herein as SEQ ID NO. 17.

In a particularly preferred embodiment of the present invention, both the E1 and E3 loci are deleted from the C68 genome.

The viral vectors of the present invention may be produced in engineered cell lines containing a complement of any deleted genes required for viral replication. However, replication of viral vectors according to the present invention may be sub-optimal in cells designed to facilitate replication of other serotypes. Therefore, the adenoviral vectors according to the present invention preferably further comprise one or more modifications designed to optimise vector growth and yield in transformed cell lines, such as HEK293, expressing the genes functionally deleted in the adenoviral vector according to the present invention.

Of particular importance for viral replication in HEK293 cells is the gene product of E4Orf6, a multifunctional protein implicated in late viral mRNA splicing and selective export of viral mRNA, viral DNA synthesis and inhibition of apoptosis. Suboptimal interaction between E4Orf6 and the cell-expressed E1B-55K is believed to reduce the yield of ChAdOx2 vectors in HEK293 cells. Therefore, the native E4Orf6 region may be replaced with a heterologous E4Orf6 region.

In a preferred embodiment, the native E4Orf4, E4Orf6 and E4Orf6/7 coding regions are replaced with the E4Orf4, E4Orf6 and E4Orf6/7 coding regions from AdHu5. In a particularly preferred embodiment, the recombinant E4 region comprises the E4Orf1, E4Orf2 and E4Orf3 coding regions from AdY25 and the E4Orf4, E4Orf6 and E4Orf6/7 coding regions from AdHu5.

The amino acid sequence of E4Orf4 from AdHu5 is found in SEQ ID NO. 7. A corresponding nucleotide sequence is found at nucleotides 29262 to 28918 of the ChAdOx2 vector sequence (SEQ ID NO. 10). The amino acid sequence of the E4Orf6 from AdHu5 is found in SEQ ID NO. 8. A corresponding nucleotide sequence is found at nucleotides 28997 to 28113 of SEQ ID NO. 10. The amino acid sequence of the E4Orf6/7 from AdHu5 is found in SEQ ID NO. 9. A corresponding nucleotide sequence is found at nucleotides 28997 to 27834 of SEQ ID NO. 10.

In one preferred embodiment, the vector of the present invention comprises the nucleotide sequences of AdHu5 E4Orf4, E4Orf6 and E4Orf6/7 or sequences substantially identical thereto.

The amino acid sequence of E4Orf1 from AdY25 is provided herein as SEQ ID NO. 3. A corresponding nucleotide sequence is found at nucleotides 30434 to 30060 of the ChAdOx2 vector sequence (SEQ ID NO. 10).

The amino acid sequence of E4Orf2 from AdY25 is provided herein as SEQ ID NO. 4. A corresponding nucleotide sequence is found at nucleotides 30010 to 29621 of SEQ ID NO. 10.

The amino acid sequence of E4Orf3 from AdY25 is provided herein as SEQ ID NO. 5. A corresponding nucleotide sequence is found at nucleotides 29624 to 29271 of SEQ ID NO. 10.

In a particularly preferred embodiment of the present invention, the viral vector comprises a modified form of the native C68 genome, wherein the native C68 nucleotide sequence lacks the nucleotide sequences which encode the adenovirus E1 and E3 regions, and has the native E4 locus replaced with E4Orf4, E4Orf6 and E4Orf6/7 coding regions from AdHu5, and the E4Orf1, E4Orf2 and E4Orf3 coding regions from AdY25. This particularly preferred viral vector according to the invention is referred to herein as "ChAdOx2".

An exemplary nucleotide sequence encoding ChAdOx2, with a Gateway® Destination Cassette in the E1 locus) is set out in SEQ ID NO. 10.

Preferably, the genome of the viral vector according to the present invention comprises the nucleotide sequence of SEQ ID NO.10 or a sequence substantially identical thereto, into which is inserted the exogeneous nucleotide sequence encoding the protein of interest.

A second aspect of the present invention provides a pharmaceutical or immunogenic composition comprising the viral vector according to the second aspect of the present invention optionally in combination with one or more additional active ingredients, a pharmaceutically acceptable carrier, diluent, excipient or adjuvant.

Preferably, the composition is an immunogenic and/or antigenic composition. The immunogenic and/or antigenic compositions according to the present invention may be prophylactic (to prevent infection), post-exposure (to treat after infection but before disease) or therapeutic (to treat disease). Preferably, the composition is prophylactic or post-exposure. Preferably, the composition is a vaccine.

Where the immunogenic composition is for prophylactic use, the subject is preferably an infant, young child, older child or teenager. Where the immunogenic composition is for therapeutic use, the subject is preferably an adult.

The composition may comprise one or more additional active agents, such as an anti-inflammatory agent (for example a p38 inhibitor, glutamate receptor antagonist, or a calcium channel antagonist), AMPA receptor antagonist, a chemotherapeutic agent and/or an antiproliferative agent. The composition may also comprise one or more antimicrobial compounds. Examples of suitable antimicrobial compounds include antituberculous chemotherapeutics such as rifampicin, isoniazid, ethambutol and pyrizinamide.

Suitable carriers and/or diluents are well known in the art and include pharmaceutical grade starch, mannitol, lactose, magnesium stearate, sodium saccharin, talcum, cellulose, glucose, sucrose, (or other sugar), magnesium carbonate, gelatin, oil, alcohol, detergents, emulsifiers or water (preferably sterile). The composition may be a mixed preparation of a composition or may be a combined preparation for simultaneous, separate or sequential use (including administration).

Suitable adjuvants are well known in the art and include incomplete Freund's adjuvant, complete Freund's adjuvant, Freund's adjuvant with MDP (muramyldipeptide), alum (aluminium hydroxide), alum plus Bordatella pertussis and immune stimulatory complexes (ISCOMs, typically a matrix of Quil A containing viral proteins).

The composition according to the invention for use in the aforementioned indications may be administered by any convenient method, for example by oral (including by inhalation), parenteral, mucosal (e.g. buccal, sublingual, nasal), rectal or transdermal administration and the compositions adapted accordingly.

For oral administration, the composition can be formulated as liquids or solids, for example solutions, syrups, suspensions or emulsions, tablets, capsules and lozenges.

A liquid formulation will generally consist of a suspension or solution of the compound or physiologically acceptable salt in a suitable aqueous or non-aqueous liquid carrier(s) for example water, ethanol, glycerine, polyethylene glycol or oil. The formulation may also contain a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and microcrystalline cellulose.

A composition in the form of a capsule can be prepared using routine encapsulation procedures. For example, powders, granules or pellets containing the active ingredient can be prepared using standard carriers and then filled into a hard gelatine capsule; alternatively, a dispersion or suspension can be prepared using any suitable pharmaceutical carrier(s), for example aqueous gums, celluloses, silicates or oils and the dispersion or suspension then filled into a soft gelatine capsule.

Compositions for oral administration may be designed to protect the active ingredient against degradation as it passes through the alimentary tract, for example by an outer coating of the formulation on a tablet or capsule.

Typical parenteral compositions consist of a solution or suspension of the compound or physiologically acceptable salt in a sterile aqueous or non-aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

Compositions for nasal or oral administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively the sealed container may be a unitary dispensing device such as a single dose nasal inhaler or an aerosol dispenser fitted with a metering valve, which is intended for disposal once the contents of the container have been exhausted. Where the dosage form comprises an aerosol dispenser, it will contain a pharmaceutically acceptable propellant. The aerosol dosage forms can also take the form of a pump-atomiser.

Compositions suitable for buccal or sublingual administration include tablets, lozenges and pastilles, wherein the active ingredient is formulated with a carrier such as sugar and acacia, tragacanth, or gelatin and glycerin.

Compositions for rectal or vaginal administration are conveniently in the form of suppositories (containing a conventional suppository base such as cocoa butter), pessaries, vaginal tabs, foams or enemas.

Compositions suitable for transdermal administration include ointments, gels, patches and injections including powder injections.

Conveniently the composition is in unit dose form such as a tablet, capsule or ampoule.

The pharmaceutical composition is preferably sterile. It is preferably pyrogen-free. It is preferably buffered e.g. at between pH 6 and pH 8, generally around pH 7. Preferably, the composition is substantially isotonic with humans.

Preferably, the pharmaceutical compositions of the present invention deliver an immunogenically or pharmaceutically effective amount of the viral vector to a patient. As used herein 'immunogenically or pharmaceutically effective amount' means that the administration of that amount to an individual, either as a single dose or as a series of doses, is effective for prevention or treatment of a disease or condition. In particular, this phrase means that a sufficient amount of the viral vector is delivered to the patient over a suitable timeframe such that a sufficient amount of the antigen is produced by the patient's cells to stimulate an immune response which is effective for prevention or treatment of a disease or condition. This amount varies depending on the health and physical condition of the individual to be treated, age, the capacity of the individual's immune system, the degree of protection desired, the formulation of the vaccine, the doctor's assessment of the medical situation and other relevant factors.

In general, a pharmaceutically effective dose comprises $1 \times 10^7$ to $1 \times 10^{12}$ viral particles (vp), preferably $1 \times 10^{10}$ to $1 \times 10^{11}$ particles. More preferably, a pharmaceutically effective dose comprises $2.5 \times 10^{10}$ v.p. to $5 \times 10^{10}$ vp. Most preferably, a pharmaceutically effective dose comprises $2.5 \times 10^{10}$ v.p.

In a preferred embodiment, there is provided a vaccine based on ChAdOx2, wherein the vaccine contains antigens from *Mycobacterium avium* subspecies paratuberculosis (MAP). Preferably, this vaccine is administered at a dose of between $5 \times 10^9$ and $5 \times 10^{10}$ vp. More preferably, this vaccine is administered at a dose of between $2.5 \times 10^{10}$ v.p. and $5 \times 10^{10}$ vp. Most preferably, the vaccine is administered at a dose of $2.5 \times 10^{10}$ v.p.

In a preferred embodiment, there is provided a vaccine based on ChAdOx2, wherein the ChAdOx2 vector encodes the rabies virus glycoprotein. In a preferred embodiment, this vaccine is administered to animals at a dose of between $1 \times 10^6$ and $1 \times 10^8$ infectivity units. In another preferred embodiment, this vaccine is administered to humans at a dose of between $5 \times 10^9$ and $5 \times 10^{10}$ vp. More preferably, this vaccine is administered in humans at a dose of between $2.5 \times 10^{10}$ v.p. and $5 \times 10^{10}$ vp. Most preferably, the vaccine is administered in humans at a dose of $2.5 \times 10^{10}$ v.p.

The immunogenic composition of the present invention may also comprise one or more other viral vectors, preferably other adenoviral vectors.

A third aspect of the present invention provides the use of the viral vector according to the first aspect of the present invention or the immunogenic composition according to the second aspect of the present invention. In particular, the third aspect provides the use of the viral vector or the immunogenic composition of the present invention in medicine.

This aspect also provides: i) the viral vector or the immunogenic composition according to the present invention for use in medicine and ii) the use of the viral vector or the immunogenic composition according to the present invention in the manufacture of a medicament for use in medicine. Some exemplary medical uses are described in further detail below.

In one embodiment, the viral vector according to the first aspect of the present invention or the immunogenic composition according to the second aspect of the present invention may be used to deliver a transgene into a host cell. This method preferably comprises the step of administering to said host cell a viral vector according to the second aspect of the present invention or the immunogenic composition according to the third aspect of the present invention.

Preferably, the host cell is an animal cell, more preferably a mammalian cell. Preferred mammals include chickens, other poultry, cows, sheep, goats, pigs, wild boar, buffalo, bison, horses, camelids, deer, elephants, badgers, possums, cats, lions, monkeys and humans. Preferably, the host cell is a somatic cell. The host cell may be selected from the group consisting of an antigen-presenting dendritic cell, langerhans cell, macrophage, B cell, lymphocyte, leukocyte, myocyte and fibroblast.

This method may be carried out in vitro or in vivo. Where the method is carried out in vitro, the viral vector or immunogenic composition is brought into contact with the host cell under suitable conditions such that transduction or non-productive infection of the host cell with the viral vector is facilitated. In this embodiment, the host cell may comprise an isolated host cell or a sample from an animal subject. Where the method is carried out in vivo, the viral vector or immunogenic composition is preferably administered to the animal subject such that transduction of one or more cells of the subject with the viral vector is facilitated. Preferably, the viral vector or immunogenic composition is administered to the subject by oral (including by inhalation), parenteral (e.g. intramuscular, subcutaneous, intravenous or intraperitoneal), mucosal (e.g. buccal, sublingual, nasal), rectal or transdermal administration.

Preferably, the transduction of the host cell with the viral vector of the present invention results in the stable delivery of the exogeneous nucleotide sequence of interest into the host cell.

Therefore, in another embodiment, the viral vector according to the first aspect of the present invention or the immunogenic composition according to the second aspect of the present invention may be used to elicit an immune response in an animal. This method preferably comprises the step of administering to said animal a viral vector according to the first aspect of the present invention or the immunogenic composition according to the second aspect of the present invention.

Where the protein or polypeptide of interest is an antigen, expression of the protein or polypeptide in an animal will result in the elicitation of a primary immune response to that antigen, leading to the development of an immunological memory which will provide an enhanced response in the event of a secondary encounter, for example upon infection by the pathogen from which the antigen was derived.

Preferably, the animal is a naïve animal, i.e. an animal that has not previously been exposed to the pathogen or antigens in question.

As well as eliciting an immune response in an animal, the viral vector of the present invention or the immunogenic composition thereof can be used to boost the immune response of an animal previously exposed to the antigen.

Therefore, in a further embodiment, the viral vector according to the first aspect of the present invention or the immunogenic composition according to the second aspect of the present invention may be used to boost an immune response in an animal. This method preferably comprises the step of administering to said animal a viral vector according to the second aspect of the present invention or the immunogenic composition according to the third aspect of the present invention.

Preferably, the animal subject has been previously exposed to the antigen in question, or "primed". For example, the subject may have previously been inoculated or vaccinated with a composition comprising the antigen, or may have previously been infected with the pathogen from which the antigen was derived. The subject may be latently infected with the pathogen from which the antigen was derived.

In another embodiment, the vector according to the first aspect of the present invention or the immunogenic composition according to the second aspect of the present invention may be used to treat or prevent at least one disease in a patient. A method of treating or preventing a disease in a patient according to the invention preferably comprises the step of administering to said patient a viral vector according to the first aspect of the present invention or the immunogenic composition according to the second aspect of the present invention.

Preferably, the disease is selected from the group consisting of Tuberculosis and other mycobacterial infections including Johne's disease, Crohn's disease, malaria, influenza, HIV/AIDS, Hepatitis C, Cytomegalovirus infection, Human papilloma virus infection, adenoviral infection, leishmaniasis, *streptococcus* spp., *staphylococcus* spp., *meningococcus* spp., infection, foot and mouth disease, chikungunya virus infection, Zika virus, rabies, Crimean Congo haemorrhagic fever, Ebola virus disease, Marburg, Lassa fever, MERS and SARS coronavirus diseases, Nipah and Rift Valley fever, Zika, Chikungunya.

Most preferably, the disease is selected from the group consisting of Tuberculosis and other mycobacterial infections, and rabies.

As well as inducing an immune response against the pathogenic organism from which the heterologous antigen is derived, the adenoviral vector of the present invention may also induce an immune response against the adenovirus from which the viral vector is derived. As such, an immune response against C68 may be elicited. The immune response induced against C68 may also be cross-reactive with other adenoviral serotypes, and as such an immune response against more than one adenovirus may be elicited. The viral vector according to the second aspect of the present invention or the immunogenic composition according to the third aspect of the present invention can therefore also be used for treating or preventing an adenoviral disease.

This embodiment of the present invention therefore also provides the treatment or prevention of at least one adenoviral disease and at least one non-adenoviral disease in a patient.

In a further embodiment, the viral vector according to the first aspect of the present invention or the immunogenic composition according to the second aspect of the present invention may be used to induce an immune response in an animal that will break tolerance to a self antigen. This method preferably comprises the step of administering to said animal a viral vector according to the first aspect of the present invention or the immunogenic composition according to the second aspect of the present invention.

Many tumour cells are tolerated by the patient's immune system, on the grounds that tumour cells are essentially the patient's own cells that are growing, dividing and spreading without proper regulatory control. Thus, cancerous tumours are able to grow unchecked within the patient's body. However, the viral vector of the present invention can be used to stimulate a patient's immune system to attack the tumour cells in a process known as "cancer immunotherapy". Specifically, the vector of the present invention can be used to 'train' the patient's immune system to recognise tumour cells as targets to be destroyed. This can be achieved by including within the viral vector an exogeneous nucleotide sequence encoding a suitable self-antigen. As described previously, suitable self-antigens include antigens expressed by tumour cells which allow the immune system to differentiate between tumour cells and other cell types. Suitable self-antigens include antigens that are either inappropriate for the cell type and/or its environment, or are only normally present during the organisms' development (e.g. foetal antigens). For example, GD2 is normally only expressed at a significant level on the outer surface membranes of neuronal cells, where its exposure to the immune system is limited by the blood-brain barrier. However, GD2 is expressed on the surfaces of a wide range of tumour cells including small-cell lung cancer, neuroblastoma, melanomas and osteosarcomas. Other suitable self-antigens include cell-surface receptors that are found on tumour cells but are rare or absent on the surface of healthy cells. Such receptors may be responsible for activating cellular signalling pathways that result in the unregulated growth and division of the tumour cell. For example, ErbB2 is produced at abnormally high levels on the surface of breast cancer tumour cells. Thus, the adenoviral vector of the present invention may be used to induce an immune response against a tumour cell, and can therefore be used in the treatment of cancer.

The adenoviral vector of the invention can be used to treat, prevent or limit development of a tumour or cancer, including, but not limited to, cancer of the spleen, pancreas, prostate, liver, lung, breast, bowel, brain and colon.

A method of treating or preventing cancer in a patient comprises administering a therapeutically-effective dose of the adenoviral vector of the invention to a patient.

The adenoviral vector of the invention can also be used to treat autoimmune conditions, or conditions caused by hypersensitivity to own antigens.

A method of treating an autoimmune condition in a patient comprises administering a therapeutically-effective dose of the adenoviral vector of the invention to a patient.

The following details apply mutatis mutandis to all of the above uses of the vector and immunogenic composition of the present invention.

The treatment and prevention of many diseases, including liver stage malaria, tuberculosis and influenza, are associated with the maintenance of a strong cell-mediated response to infection involving both CD4+ and CD8+ T cells and the ability to respond with Th1-type cytokines, particularly IFN-γ, TNF-α, IL-2 and IL-17. Although many subunit vaccine platforms effectively generate human immunity, the generation of robust cell-mediated immune responses, particularly CD4+ and CD8+ T cell immune responses, has been much more challenging. The viral vector of the present invention preferably stimulates both cellular and humoral immune responses against the encoded antigen.

It is also desirable to induce a memory immune response. Memory immune responses are classically attributed to the reactivation of long-lived, antigen-specific T lymphocytes that arise directly from differentiated effector T cells and persist in a uniformly quiescent state. Memory T cells have been shown to be heterogeneous and to comprise at least two subsets, endowed with different migratory capacity and effector function; effector memory T cells (TEM) and central memory T cells (CTM). TEM resemble the effector cells generated in the primary response in that they lack the lymph node-homing receptors L-selectin and CCR7 and express receptors for migration into inflamed tissues. Upon re-encounter with antigen, these TEM can rapidly produce IFN-γ or IL-4 or release pre-stored perform. TCM express L-selectin and CCR7 and lack immediate effector function. These cells have a low activation threshold and, upon re-stimulation in secondary lymphoid organs, proliferate and differentiate to effectors.

Preferably, the viral vector according to the first aspect of the present invention or the immunogenic composition according to the second aspect of the present invention is capable of eliciting, inducing or boosting an antigen-specific immune response. Preferably, the immune response is a strong T cell immune response, for example a strong CD8+ and CD4+ T cell response. Preferably, the T cell immune response is a protective T cell immune response. Preferably, the T cell immune response is long lasting and persists for at least 1, 2, 5, 10, 15, 20, 25 or more years. Preferably, the immune response induced is a memory T cell immune response.

The viral vector of the first aspect of the present invention or immunogenic composition according to the second aspect of the present invention may be administered to the host cell or subject either as a single immunisation or multiple immunisations. Preferably, the viral vector or immunogenic composition thereof are administered as part of a single, double or triple vaccination strategy. They may also be administered as part of a homologous or heterologous prime-boost immunisation regime.

The vaccination strategy or immunisation regime may include second or subsequent administrations of the viral vector or immunogenic composition of the present invention. The second administration can be administered over a short time period or over a long time period. The doses may be administered over a period of hours, days, weeks, months or years, for example up to or at least 1, 2, 3, 4, 5, 6, 7, 8, 9, or 10 or more weeks or 0.25, 0.5, 0.75, 1, 5, 10, 15, 20, 25, 30, 35 or 40 or more years after the first administration. Preferably, the second administration occurs at least 2 months after the first administration. Preferably, the second administration occurs up to 10 years after the first administration. These time intervals preferably apply mutatis mutandis to the period between any subsequent doses.

The viral vector and/or immunogenic composition may be administered alone or in combination with other viral or non-viral DNA/protein vaccines. Preferred examples include modified vaccinia Ankara (MVA), Fowlpox 9 (FP9) and other adenoviral vector vaccines.

The viral vector and/or immunogenic composition may be administered to the subject by oral (including by inhalation), parenteral, mucosal (e.g. buccal, sublingual, nasal), rectal or transdermal administration. Alternatively, the viral vector and/or immunogenic composition may be administered to an isolated host cell or sample from a subject by contacting the cell(s) with the viral vector or immunogenic composition in vitro under conditions that facilitate the transduction of the host cell with the viral vector.

The viral vector and immunogenic composition of the present invention are not limited to the delivery of nucleic acid sequences encoding antigens. Many diseases, including cancer, are associated with one or more deleterious mutant alleles in a patient's genome. Gene therapy is a process involving the insertion of genes into the patient's cells or tissues to replace the deleterious mutant or non-functional allele(s) with 'normal' or functional allele(s). Commonly, a functional allele is inserted into a non-specific location within the genome to replace the non-functional allele. Alternatively, the non-functional allele may be swapped for the functional allele through homologous recombination. Subsequent expression of the functional allele within the target cell restores the target cell to a normal state and thus provides a treatment for the disease. The 'normal' or functional allele(s) may be inserted into a patient's genome using a viral vector. The present invention therefore also provides the use of the viral vector according to the first aspect of the present invention or the immunogenic composition according to the second aspect of the present invention in gene therapy.

This method preferably comprises the step of administering to said animal a viral vector according to the second aspect of the present invention or the immunogenic composition according to the third aspect of the present invention.

The vector of the present invention may comprise an exogenous nucleotide sequence encoding the functional or 'normal' protein, the non-functional or 'mutant' version of which is associated with a disease or condition.

Preferably, the target cell is a somatic cell. The subject to be treated is preferably mammalian. Preferred mammals include chickens, other poultry, cows, sheep, goats, pigs, wild boar, buffalo, bison, horses, camelids, deer, elephants, badgers, possums, cats, lions, monkeys and humans.

A fourth aspect of the present invention provides a polynucleotide sequence encoding the viral vector according to the first aspect of the present invention.

Preferably, the polynucleotide sequence comprises the sequence of SEQ ID NO. 10, or a sequence substantially identical thereto. The polynucleotide may additionally comprise the exogenous nucleotide sequence of interest.

A fifth aspect of the present invention provides a host cell transduced or infected with the viral vector according to the first aspect of the present invention. Following transduction or infection, the host cell will express the exogenous nucleotide sequence in the nucleic acid molecule to produce the molecule of interest, in addition to any other adenoviral proteins encoded by the nucleic acid molecule. Preferably, the host cell is stably transduced and suitable for viral propagation.

The host cell may be an isolated host cell, part of a tissue sample from an organism, or part of a multicellular organism or organ or tissue thereof.

Preferably, the host cell is a somatic cell. Preferably, the host cell is not a stem cell, more particularly an embryonic stem cell, more particularly a human embryonic stem cell.

The host cell may be selected from the group consisting of an antigen-presenting dendritic cell, langerhans cell, macrophage, B cell, lymphocyte, leukocyte, myocyte and fibroblast.

Preferably, the host cell is an animal cell, more preferably a mammalian cell. Preferred mammals include chickens, other poultry, cows, sheep, goats, pigs, wild boar, buffalo, bison, horses, camelids, deer, elephants, badgers, possums, cats, lions, monkeys and humans.

The fifth aspect of the present invention also encompasses an animal transduced or infected with the viral vector according to the first aspect of the present invention. Preferably, the animal comprises one or more cells transformed or transfected with the viral vector according to the first aspect of the present invention. Preferably, the animal is a mammal. Preferred mammals include chickens, other poultry, cows, sheep, goats, pigs, wild boar, buffalo, bison, horses, camelids, deer, elephants, badgers, possums, cats, lions, monkeys and humans.

In a sixth aspect, the present invention provides a method of producing the viral vector according to the first aspect of the present invention. Preferably, the method comprises the step of incorporating the polynucleotide sequence according to the fourth aspect of the invention into a Bacterial Artificial Chromosome (BAC) to produce an Ad-BAC vector.

Unlike plasmid vectors, BACs are present within *E. coli* in single copy conferring increased genetic stability. In addition, the single copy BAC vectors permit very precise modifications to be made to the viral genome by recombineering (recombination mediated genetic engineering).

Preferably, incorporation of the polynucleotide sequence of the invention (preferably derived from C68) into a Bacterial Artificial Chromosome (BAC) comprises the steps of:
  i) constructing a BAC rescue vector comprising regions of homology to the left and right flanks of the viral nucleotide sequence;
  ii) linearising the BAC rescue vector; and
  iii) performing homologous recombination in a host cell between the viral nucleotide sequence and the linearised BAC rescue vector to incorporate the viral nucleotide sequence into the BAC rescue vector.

Preferably, the polynucleotide sequence incorporated into the BAC rescue vector comprises the sequence of SEQ ID NO. 10 or a sequence substantially identical thereto.

Preferably, the method additionally comprises the step of further modifying the Ad-BAC vector genome. These further modifications may be carried out by GalK recombineering. This technique, pioneered by Søren Warming and colleagues, utilises the GalK gene for both positive and negative selection of recombinant clones[6]. SW102 *E. coli* cells, in which recombination may be performed, have been specifically engineered to lack the GalK gene which is required for the utilisation of galactose as the sole carbon source. Gene deletion is performed by recombination between the vector genome and a PCR amplified GalK cassette, flanked by 50 bp regions of homology either side of the gene targeted for deletion. Selection on minimal media containing only galactose should ensure that only recombinants containing the GalK gene (in place of the target gene) should grow. Replacement of GalK with a different gene sequence can be performed in a similar fashion, this time using GalK for negative selection. The addition of 2-deoxygalactose (DOG) to selection media will select clones in which GalK has been replaced since the product of GalK, galactokinase, metabolises DOG into a product that is highly toxic to *E. coli*.

Preferably, the host cell is BJ5183 *E. coli* for steps i) to iii) above and SW102 for further modifications.

Preferably, an extra homology flank is included downstream of the adenovirus E1 region to enable simultaneous deletion of E1.

Preferably, the method further includes deletion of the E3 region of the Ad-BAC vector genome. Deletion of the E3 region may be carried out by GalK recombineering.

Preferably, the method further includes introducing phage lambda site specific recombination sites attR1 and attR2 at the Ad E1 locus as part of an Invitrogen Gateway® destination cassette. Such a modification enables the efficient directional insertion of vaccine transgenes. Transgenes could also be inserted by recombineering, In-Fusion®, conventional ligation or gap repair.

A seventh aspect of the present invention provides a Bacterial Artificial Chromosome (BAC) clone comprising a polynucleotide sequence encoding the viral vector according to the first aspect of the present invention.

Preferably, the BAC clone comprises:
  (a) a BAC backbone;
  (b) the polynucleotide sequence according to the fourth aspect of the present invention.

As described above, the viral vector according to the first aspect of the present invention may be replicated in a transformed cell line or helper virus (gutless vector system) which, if necessary, comprises the complement of any genes deleted from the virus. Such genes may be deleted from the virus in order to hinder replication in host cells, but are of course required in order to replicate the viral vector to produce immunogenic compositions according to the second aspect of the present invention. One can make use of any cell line permissive of wild type adenovirus replication that has been modified to express the functionally deleted genes, or a cell line which is not permissive of wild-type virus replication which has additionally or alternatively been modified to express CAR or integrins in addition to the functionally deleted genes.

The present invention provides host cells comprising a Bacterial Artificial Chromosome (BAC) in accordance with the seventh aspect of the present invention, and suitable for propagation thereof. Preferably such host cells are bacteria, most preferably *E. coli*. Suitable examples include *E. coli* strains DH10B and SW102[9].

An eighth aspect of the present invention therefore provides a packaging cell or cell line producing or capable of producing the viral vector according to the first aspect of the present invention.

The packaging cell or cell line comprises one or more nucleotide sequences which encode the viral vector of the first aspect of the present invention. Expression of these sequences results in the production of the viral vector. Some of the required genes may be provided by infection of the cell or cell line with a viral vector according to the first aspect. Preferably, the cell comprises the complement of any genes deleted or functionally deleted from the viral vector. Preferably, the cell is an HEK293 cell or a PER.C6® cell.

Merely for the convenience of those of skill in the art, a sample of *E. coli* strain Stellar containing bacterial artificial chromosomes (BACs) containing the ChAdOx2-GFP was deposited by Isis Innovation Limited on 13 Jun. 2016 with the European Collection of Cell Cultures (ECACC) at the Health Protection Agency Culture Collections, Health Protection Agency, Porton Down, Salisbury SP4 0JG, United Kingdom under the Budapest Treaty and designated by provisional accession no. 16061301.

In respect of all designated states to which such action is possible and to the extent that it is legally permissible under the law of the designated state, it is requested that a sample of the deposited material be made available only by the issue thereof to an independent expert, in accordance with the relevant patent legislation, e.g. Rule 32(1) EPC, Rule 13(1) and Schedule 1 of the UK Patent Rules 2007, Regulation 3.25(3) of the Australian Patent Regulations and generally similar provisions mutatis mutandis for any other designated state.

As described herein, the vector ChAdOx2 is derived from chimpanzee adenovirus C68, with deletion of E1 region, E3 region, modification of E4 region and insertion of eGFP model antigen into E1 locus. The E. coli containing the BAC is a class I genetically modified organism.

The BAC propagates within the bacteria during replication and can be maintained by selection with chloramphenicol. The E. coli strain SW102 containing the bacterial artificial chromosomes into which the genomes are cloned can be propagated in Luria-Bertani broth or agar containing 12.5 µg/mL chloramphenicol at 32° C. The genome may be modified by genetic engineering in E. coli according to standard methods, as described in the specification, e.g. to insert an alternative recombinant antigen in place of eGFP.

Converting the BAC clones of the viral genomes into viruses ("rescue") can be carried out by the following steps. The E. coli host is propagated and the BAC DNA is purified from the bacteria according to standard methods. The DNA is linearised with the restriction endonuclease PacI and transfected into HEK293 cells (or a similar E1 complementing cell line). The resulting adenovirus can then be propagated and purified for use as a vaccine, for example. All of these reagents and cells are publicly available. If the deposition were rescued, the resulting virus would be a class I genetically modified organism.

In respect of all designated states to which such action is possible and to the extent that it is legally permissible under the law of the designated state, it is requested that a sample of the deposited material be made available only by the issue thereof to an independent expert, in accordance with the relevant patent legislation, e.g. Rule 32(1) EPC, Rule 13(1) and Schedule 1 of the UK Patent Rules 2007, Regulation 3.25(3) of the Australian Patent Regulations and generally similar provisions mutatis mutandis for any other designated state.

A specific embodiment of the fourth aspect of the present invention provides a polynucleotide sequence encoding an adenoviral vector according to the first aspect of the present invention, wherein said polynucleotide sequence comprises or consists of the polynucleotide sequence of the viral vector ChAdOx2 (SEQ ID NO. 10).

ChAdOx2 was deposited in a BAC contained in E. coli strain Stellar by Isis Innovation Limited on 13 Jun. 2016 with the European Collection of Cell Cultures (ECACC) at the Health Protection Agency Culture Collections, Health Protection Agency, Porton Down, Salisbury SP4 0JG, United Kingdom under the Budapest Treaty and designated by provisional accession no. 16061301. The deposited BAC additionally comprises a transgene encoding the antigen eGFP. In this aspect of the present invention, the polynucleotide sequence for ChAdOx2 preferably does not include the sequence encoding the eGFP antigen.

A further embodiment of the present invention provides a host cell transduced with the viral vector according to the first aspect of the present invention, wherein said host cell is preferably a bacterium, more preferably E. coli strain Stellar containing a bacterial artificial chromosome (BAC) containing the cloned genome of ChAdOx2 deposited by Isis Innovation Limited on 13 Jun. 2016 with the European Collection of Cell Cultures (ECACC) at the Health Protection Agency Culture Collections, Health Protection Agency, Porton Down, Salisbury SP4 0JG, United Kingdom under the Budapest Treaty and designated by provisional accession no. 16061301. The deposited BAC additionally comprises a transgene encoding the antigen eGFP. In this aspect of the present invention, the polynucleotide sequence for ChAdOx2 preferably does not include the sequence encoding the eGFP antigen. Such a host cell may be used for BAC propagation.

A specific embodiment of the seventh aspect of the present invention provides a Bacterial Artificial Chromosome (BAC) clone comprising the polynucleotide sequence according to the fourth aspect of the present invention, wherein said BAC is the BAC containing the cloned genome of ChAdOx2, deposited in E. coli strain Stellar by Isis Innovation Limited on 13 Jun. 2016 with the European Collection of Cell Cultures (ECACC) at the Health Protection Agency Culture Collections, Health Protection Agency, Porton Down, Salisbury SP4 0JG, United Kingdom under the Budapest Treaty and designated by provisional accession no. 16061301. The deposited BAC additionally comprises a transgene encoding the antigen eGFP. In this aspect of the present invention, the polynucleotide sequence for ChAdOx2 preferably does not include the sequence encoding the eGFP antigen.

A further aspect of the invention provides a kit, comprising an adenoviral vector according to the first aspect of the invention, or an immunogenic composition according to the second aspect of the invention, together with instructions for use.

The kit may include medical equipment for administering the adenoviral vector or immunogenic composition to a subject, such as a syringe. The kit may comprise instructions for administering the adenoviral vector or immunogenic composition to a subject, and may include specific dosage instructions. The kit may be useful for vaccinating a subject against a disease by inducing or enhancing an immune response, or for otherwise treating or preventing disease in a subject.

For the avoidance of doubt, it is hereby expressly stated that features described herein as 'preferred', 'preferable', "alternative" or the like may be present in the invention in isolation or in any combination with any one or more other features so described (unless the context dictates otherwise) and this constitutes and explicit disclosure of such combinations of features.

All the features of each embodiment described above apply mutatis mutandis to all other embodiments of the present invention.

The invention will now be further described with reference to the following non-limiting examples.

Example 1

Simian Adenvorius (sAd) Vaccine Vector Design and Development

Key considerations in the design of sAd vectors for use as vaccines are similar to those for AdHu5. The vaccine vector must be non-replicating and unlike adenovirus gene therapy vectors have negligible immune modulatory activity. Hence, SAd vectors lack the E1 region encoding viral transactivator proteins which are essential for virus growth and the E3 region encoding immunomodulatory proteins.

The advent of bacterial artificial chromosomes (BACs) coupled to bacteriophage λ Red recombination (recombineering) technology has facilitated the manipulation of large virus genome. Using this approach linear DNA adenovirus genomes isolated from non-human primates have been cloned for use as viral vectors.

Figure 1A:
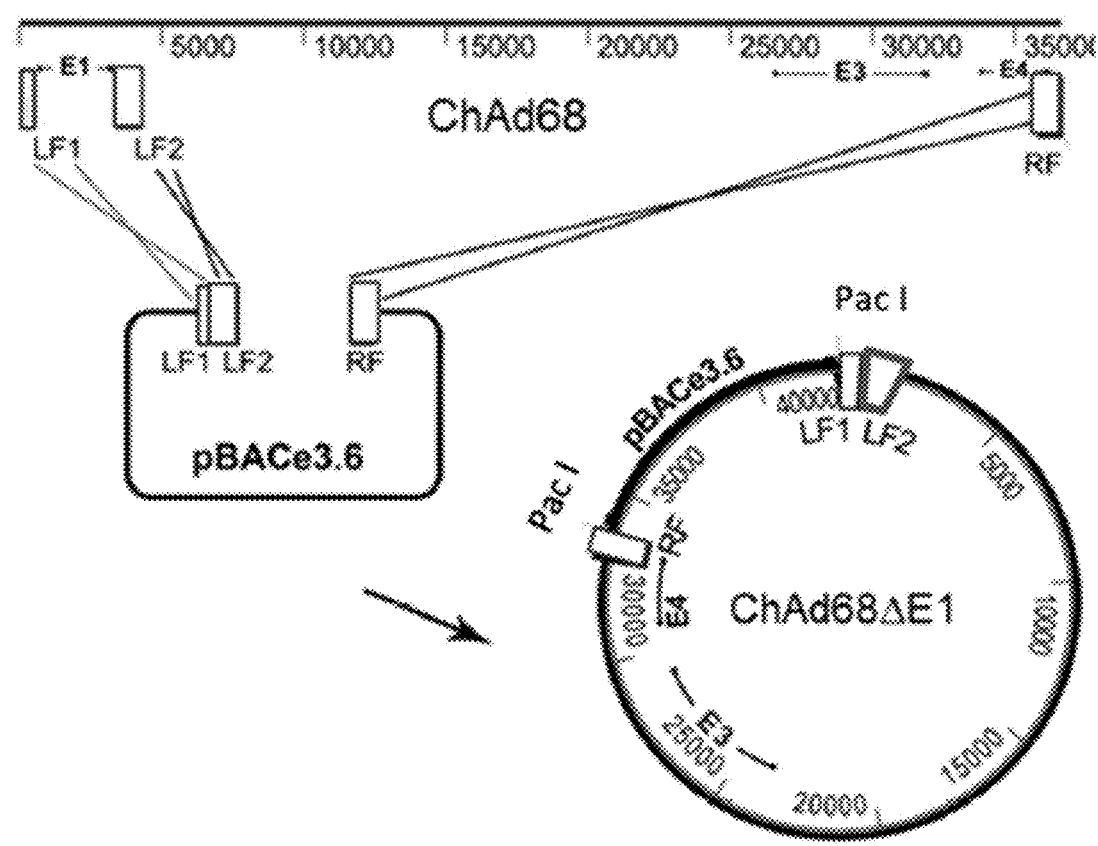

The first stage, following virus isolation and genome sequencing, is either the amplification or artificial synthesis of two products homologous to the left arm of the genome, flanking the E1 region and one, approximately 1000 bp, product homologous to the right arm of the genome each incorporating a unique restriction enzyme site for cloning and genome excision for vector production. These fragments are assembled and inserted into a BAC by conventional restriction enzyme cloning. The virus genome is then inserted into the BAC clone by single step gap repair homologous recombination to generate an E1 deleted viral vector molecular clone (FIG. 1a).

Figure 1C:
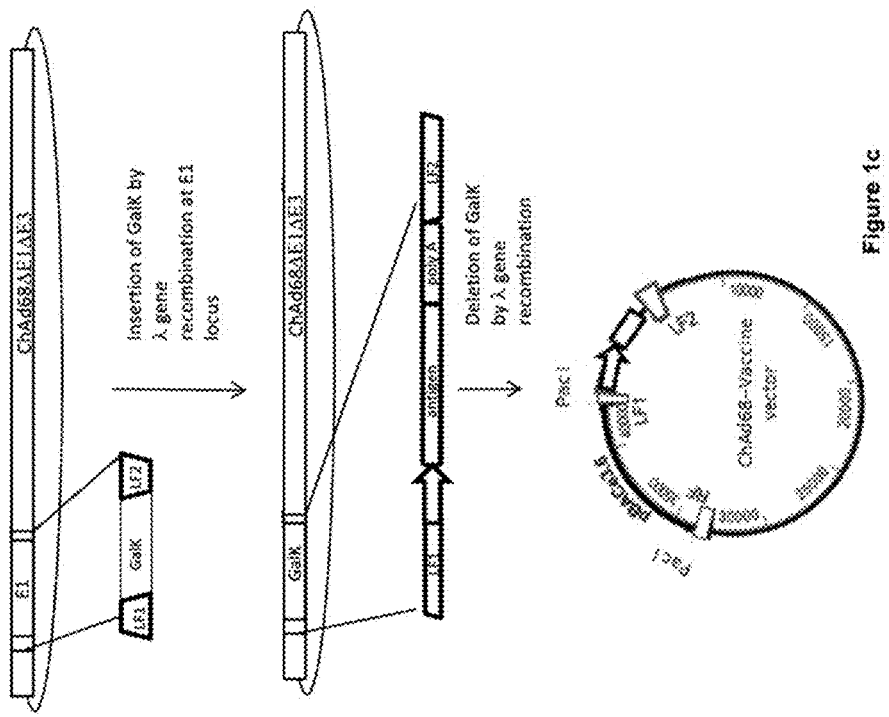
Figure 1B:
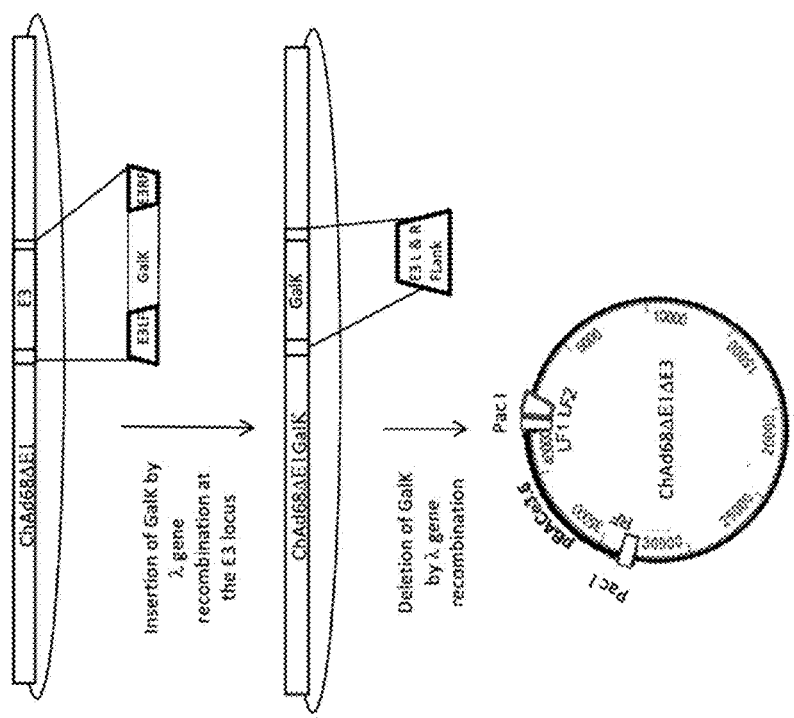

The bacteriophage λ Red recombination (recombineering) system is then used to allow seamless deletion of the adenovirus E3 immunomodulatory genes. Firstly, the bacterial galactokinase gene (GalK) is amplified from the plasmid, pGalK, such that it contains ~50 bp homology arms flanking the E3 region, this gene is inserted at the E3 locus of the BAC rescued adenovirus genome by λ Red recombination. Clones are screened for growth on galactose as this phenotype is attributed to the GalK gene product. The GalK gene is then removed by λ Red recombination with a PCR product comprised of the E3 left and right flanking region only (FIG. 1b).

Positive clones are selected on 2-deoxygalactose media which prevents growth of bacteria expressing the GalK gene. Further manipulation using λ Red recombination firstly to insert the GalK gene and then to exchange it for an antigen expression cassette at the E1 locus completes the engineering of the vaccine vector (FIG. 1c).

The linear virus genome is excised from the BAC using unique restriction enzymes, usually PacI or PmeI, and transfected into complementing cells to generate the viral vector. The antigen cassette typically consists of a strong promoter such as the minimal CMV immediate early promoter, to drive antigen expression, the antigen of interest and a polyadenylation signal.

Figure 2:
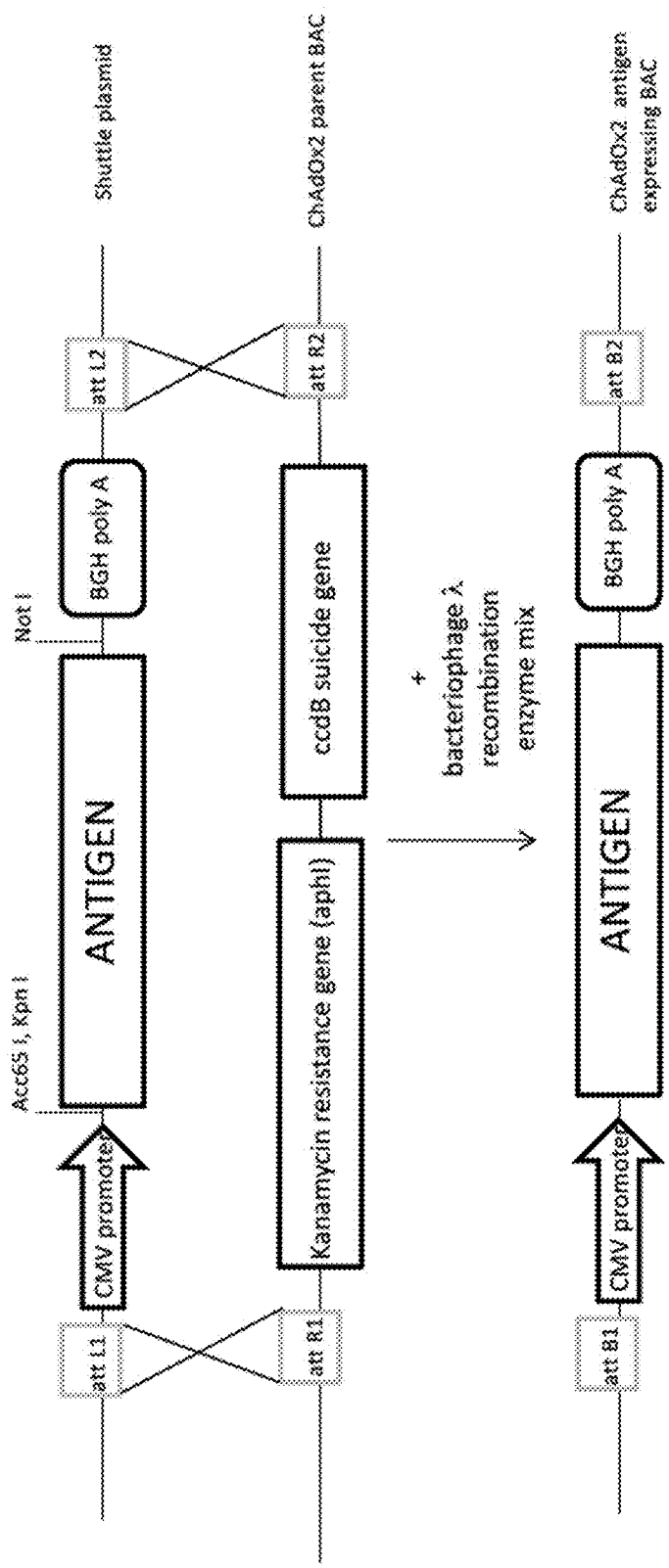

The inventors have generated a molecular toolbox that allows the insertion of any gene easily into a set region within the ChAd genome by inserting universal cassettes expressing a bacteria antibiotic resistance gene flanked by specific recombination sequences, such as attR1 and attR2, derived from bacteriophage λ (note this system is based on the Gateway cloning system from Invitrogen), into our ChAd derived vaccine vectors at the E1 locus and/or the E3 locus. Shuttle plasmids containing an antigen expression cassette flanked by specific recombination sites paired with those present in the genome (for example attR1/R2 recombination sequence requires attL1/L2 recombination sequence) allow site specific recombination in the presence of an enzyme mixture containing bacteriophage λ integrase, integration host factor and excisionase (FIG. 2).

Although the deleted E1 region from SAds is complemented by AdHu5 E1 proteins constitutively expressed by human embryonic kidney (HEK) 293 cells or PerC.6 cells, viral yields vary depending on SAd serotype. High yields of Pan5, Pan6 and Pan7, all derived from chimpanzees can be obtained from HEK293 cells, whereas ChAd1 yields are poor. For virus vectors with poor replication, further genome manipulation has been shown to increase yields. In the case of AdHu5, the E4 gene products in particular those from orf3, orf4, orf6 and orf6/7 coordinate their function with the E1 proteins (E1A and E1B 55K) and host cell cofactors to bind, regulate and de-repress several cellular functions during viral multiplication. Manipulation of the E4 region can therefore be a promising means of increasing virus yields.

Figure 3:
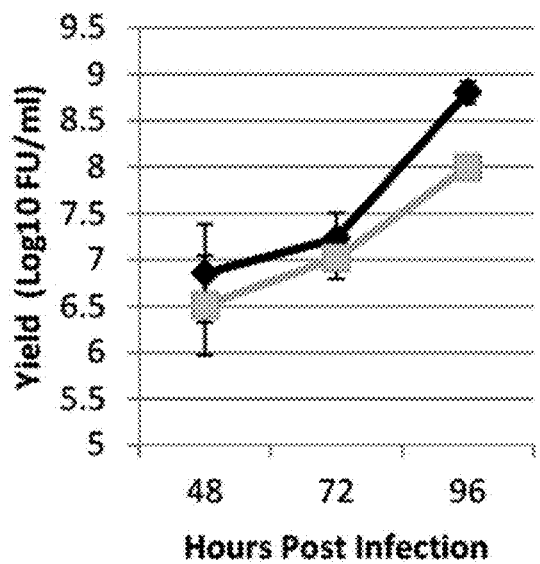

In patent publication WO2012/172277, the present inventors described the generation of a chimeric vaccine vector, ChAdOx1, derived from ChAd serotype Y25 engineered by λ Red recombination to exchange the native E4 orf4 orf6 and orf6/7 genes for those from AdHu5. This vector showed an increase in hexon protein production from HEK 293 cells compared to the ChAd parent virus. Using this approach, the inventors have now generated a novel adenovirus vector according to the present invention, ChAdOx2, an E1/E3 deleted vaccine vector derived from ChAd68 (also referred to as Pan6 and sAd25) containing E4 orf1, orf2 and orf3 from Y25 and E4 orf4, orf6 and orf6/7 from AdHu5 to increase virus yields in HEK 293 cells (FIG. 3).

SAd Vector Engineering to Improve Immunogenicity

Figure 4:
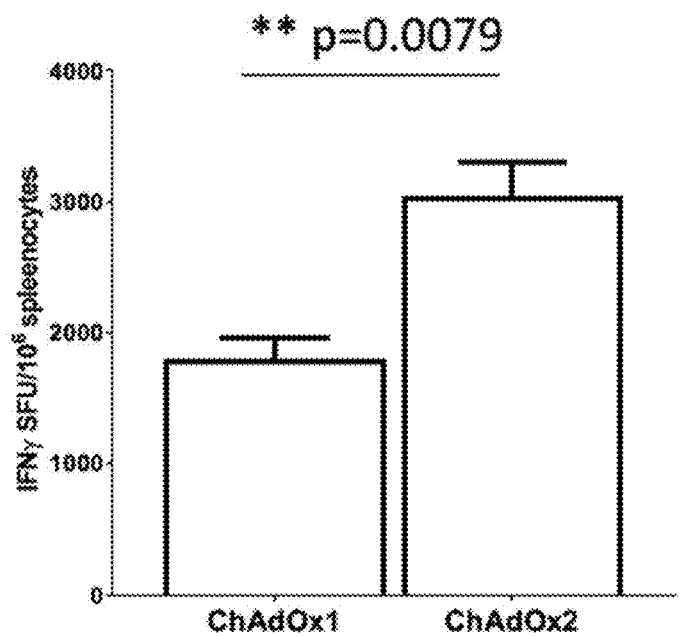

Adenovirus vaccine vectors, regardless of parental origin, can induce humoral, mucosal and cellular immune responses, depending on the route of administration. However, although the T- and B-cell responses elicited are good for most vectors, the level of immunological potency can differ depending on adenovirus vector parental strain/serotype[10, 11]. For example, when the two simian vectors ChAdOx1 (derived from Y25 and disclosed in WO2012/172277) and ChAdOx2 (derived from C68, according to the present invention), which both carried a GFP expression cassette in the E1 locus, were compared, the T-cell response elicited to GFP was significantly higher for ChAdOx2 (FIG. 4).

Example 2: Results from Phase I Clinical Trial of the Candidate *Mycobacterium avium* Subspecies Paratuberculosis (MAP) Vaccine ChAdOx2 HAV A phase I clinical trial was initiated to determine the safety and immunogenicity of the candidate *Mycobacterium avium* subspecies paratuberculosis (MAP) vaccine ChAdOx2 HAV in healthy adult volunteers. The vaccine contains antigens from *Mycobacterium avium* subspecies paratuberculosis (MAP) which is the causative agent for Johne's disease in cattle and has been linked to Crohn's disease in humans.

Figures 5, 6:
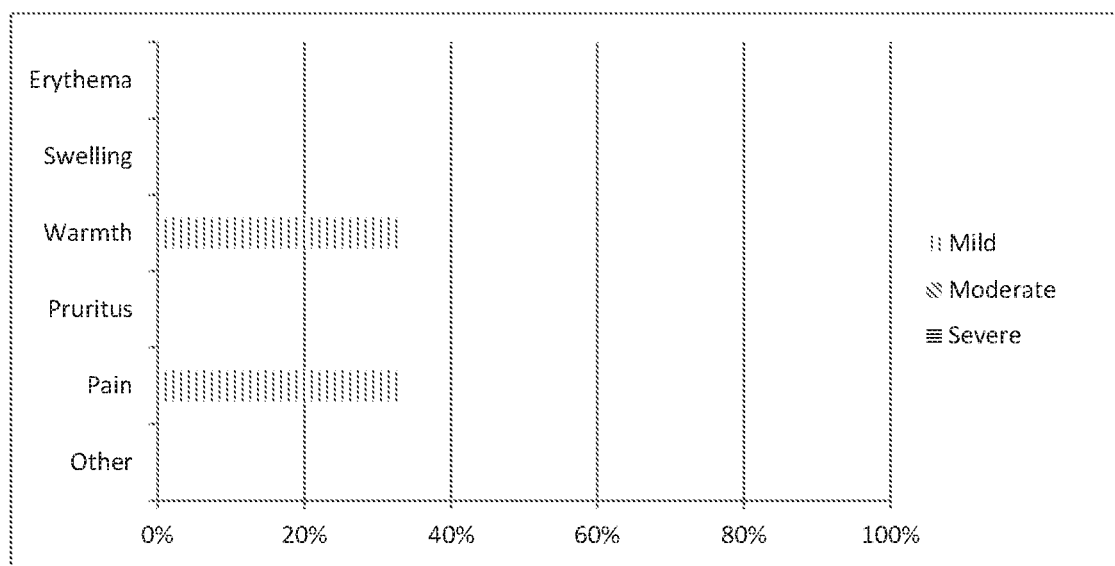
Figure 7:
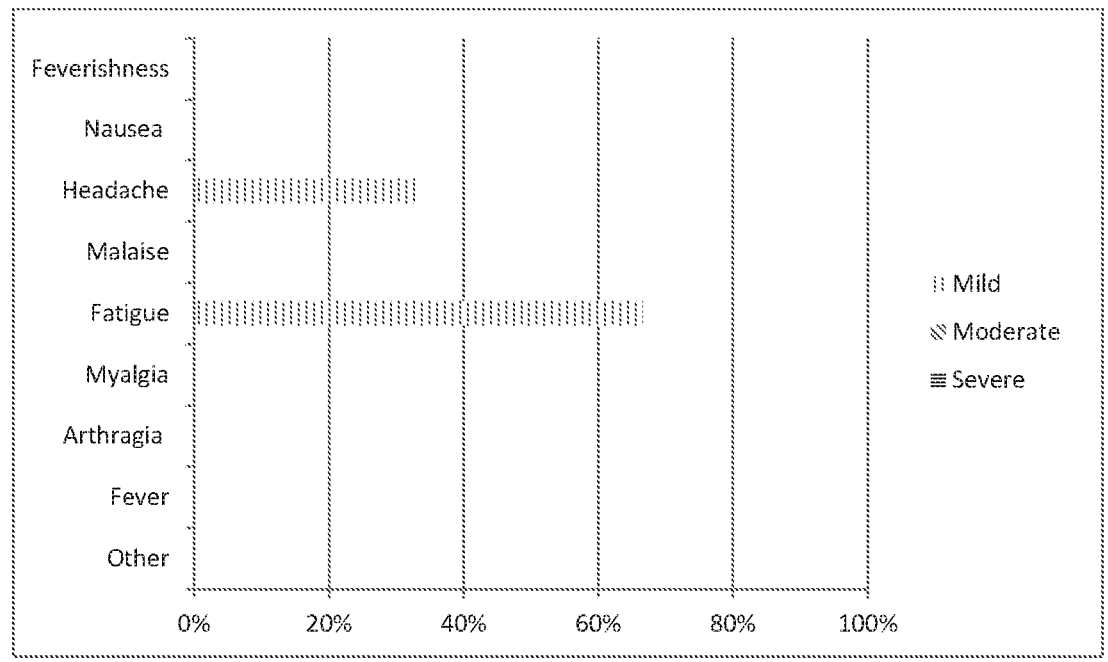
Figure 8:
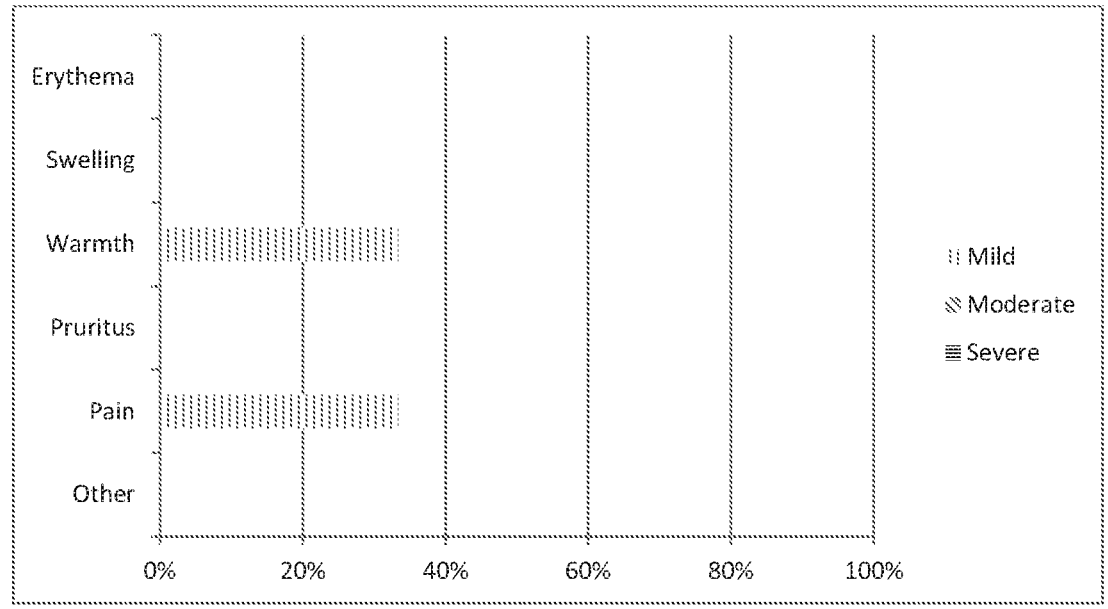
Figure 9:
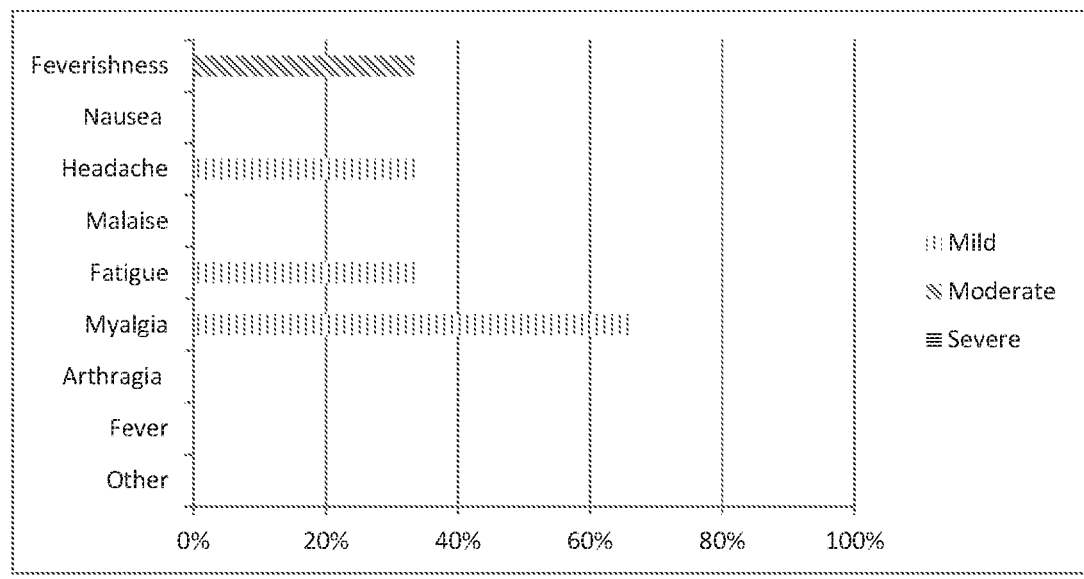
Figure 10:
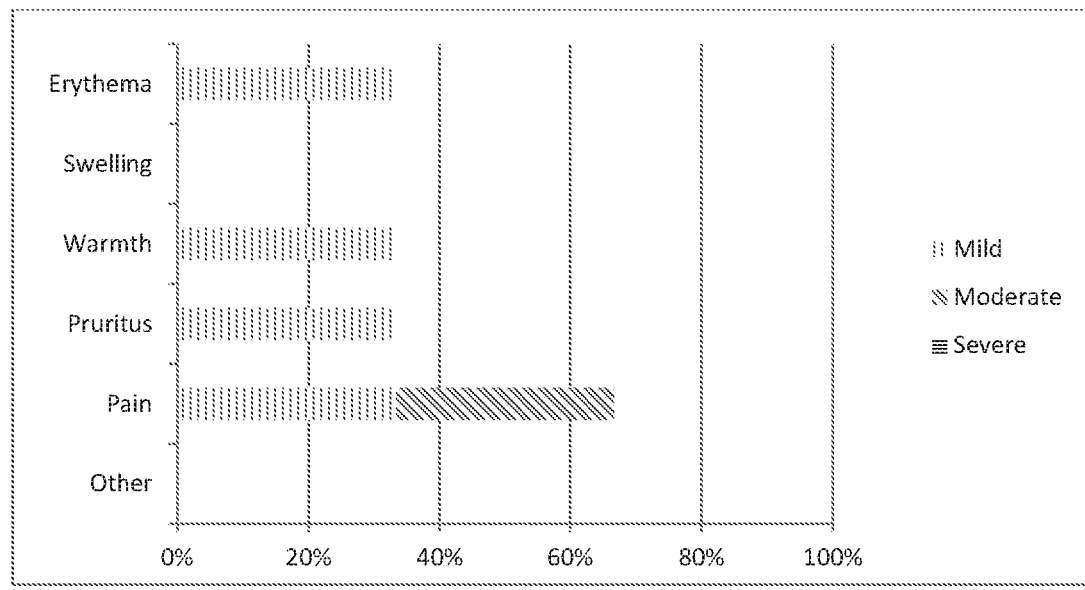

20 volunteers were screened. 13 of these were deemed eligible to take part in the study. 1 volunteer withdrew consent prior to enrolment. 9 participants received their single dose of ChAdOx2 HAV. FIG. 5 shows the study groups (table 1) and the current progress of enrollment (table 2, completed follow-up visits shaded):

FIGS. 6 to 11 show the proportions of volunteers presenting adverse events (AEs) at different dose groups. As can be seen from these figures, the vaccine is safe and well tolerated. There have been no severe or serious AEs related to ChAdOx2 HAV. FIG. 6 shows the proportion of volunteers presenting local AEs after a single dose of ChAdOx2 HAV ($5 \times 10^9$ vp). FIG. 7 shows the proportion of volunteers presenting systemic AEs after a single dose of ChAdOx2 HAV ($5 \times 10^9$ vp). FIG. 8 shows the proportion of volunteers presenting local AEs after a single dose of ChAdOx2 HAV ($2.5 \times 10^{10}$ vp). FIG. 9 shows the proportion of volunteers presenting systemic AEs after a single dose of ChAdOx2 HAV ($2.5 \times 10^{10}$ vp). FIG. 10 shows the proportion of volunteers presenting local AEs after a single dose of ChAdOx2

Figure 11:
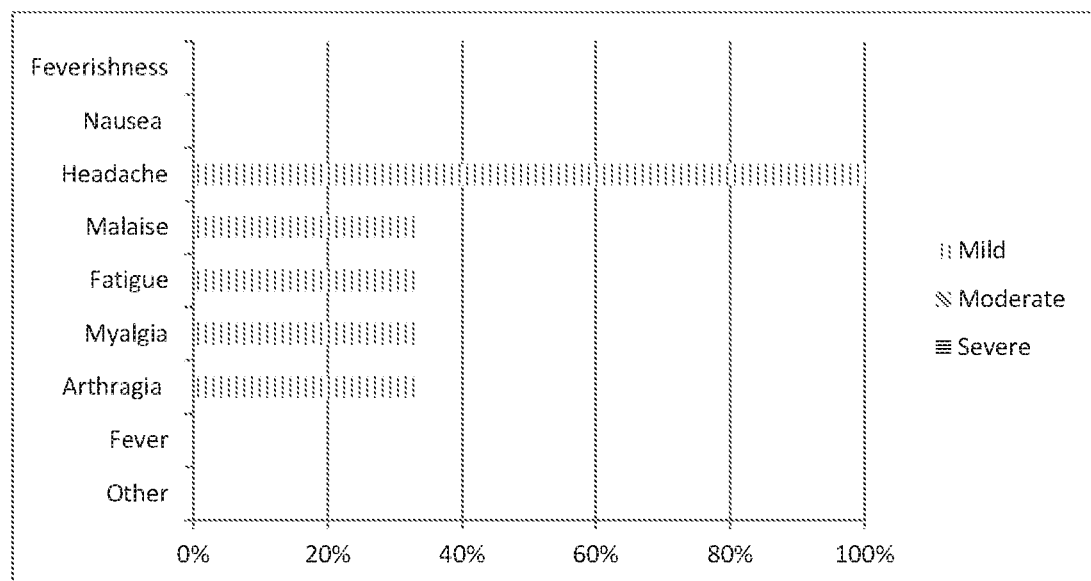

HAV ($5 \times 10^{10}$ vp). FIG. 11 shows the proportion of volunteers presenting systemic AEs after a single dose of ChAdOx2 HAV ($5 \times 10^{10}$ vp).

Responses to vaccination with ChAdOx2 HAV in humans were assessed using the interferon-gamma ELISPOT assay using freshly-isolated peripheral blood mononuclear cells (PBMC) stimulated with pools of peptides spanning the HAV vaccine construct. Assays were performed prior to vaccination (Day 0) and at one and two months' post vaccination (Day 28 and 56).

Figure 12:
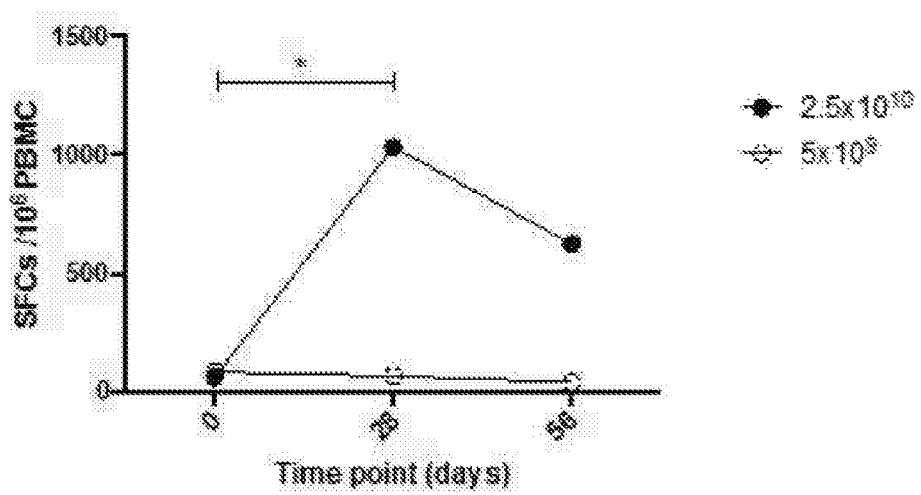

Responses to HAV antigens prior to vaccination were low, with a median response of 104 spot-forming cells per million PBMC (SFC), which increased to a median of 331 SFC at day 28 taking an average across all dose groups (FIG. 12). Responses were higher at day 28 in participants immunised with $2.5 \times 10^{10}$ v.p. than $5 \times 10^{9}$ v.p. ($p<0.05$, Kruskall-Wallis test with Dunn's multiple comparison test). Individual responses are tabulated, see FIG. 13.

Example 3: Antibody Responses in Mice Vaccinated with ChAdOx2 RabGP

The rabies virus glycoprotein coding sequence (RabGP; ERA strain; Genbank accession number AJ489620.1) was PCR amplified from a plasmid kindly supplied by Hildegund Ertl (Wistar Institute), using primers flanking Acc65I and NotI restriction enzyme sites. After digestion with these enzymes, the fragment was cloned into a similarly digested pENTR4 plasmid providing the human cytomegalovirus major immediate early promoter (IE CMV) that includes intron A and flanked by Gateway® recombination cassettes. Gateway LR recombination cloning (Life Technologies) was used to transfer the transgene cassette into the ChAdOx2 destination vector in the E1-homologous site to produce pBAC ChAdOx2 LPTOS RabGP ERA.

Following enzymatic linearization of the ChAdOx2 RabGP destination plasmid and transfection into HEK293A cells (Invitrogen, Cat. R705-07), the resultant viruses were purified by CsCl gradient ultracentrifugation. The titres were determined on HEK293A cells using anti-hexon immunostaining assay based on the QuickTiter™ Adenovirus Titer Immunoassay kit (Cell Biolabs Inc).

Figures 13, 14:
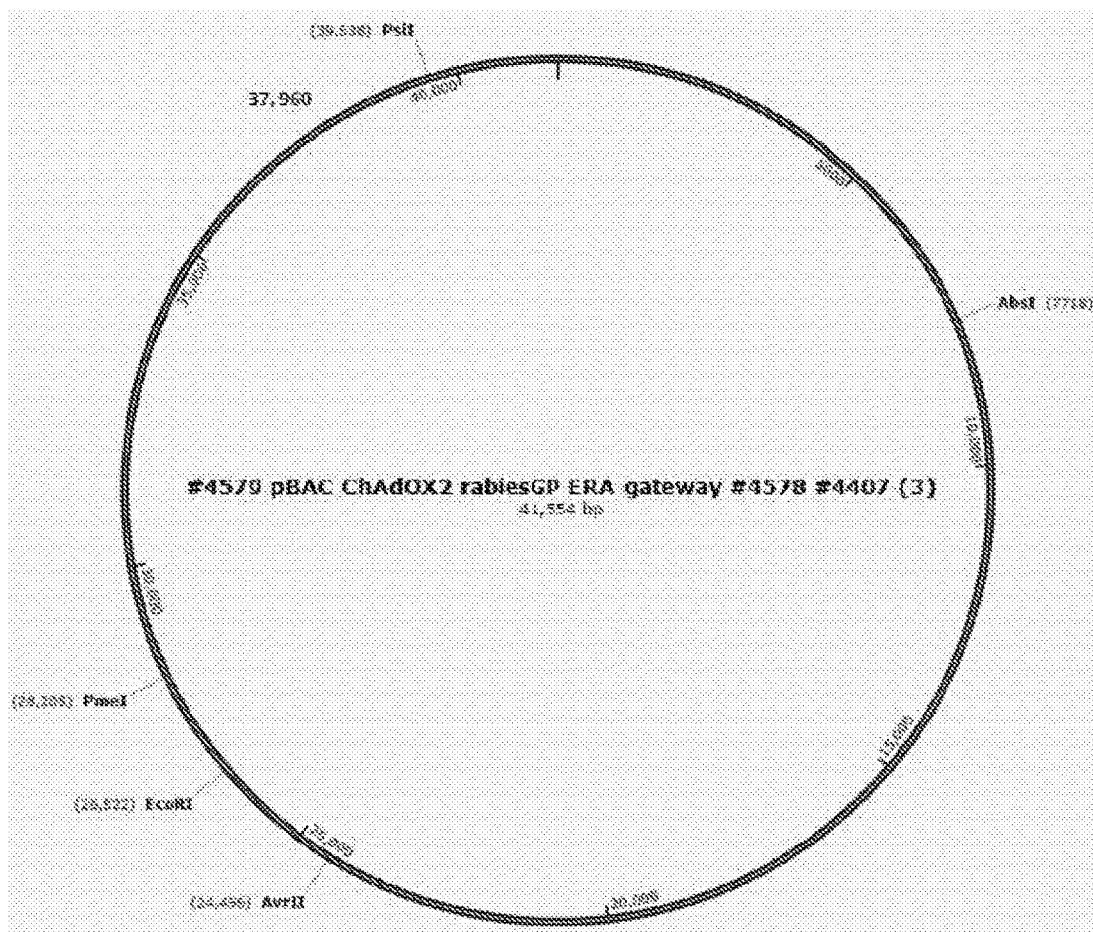
FIG. 14 shows structure of the destination vector for the ChAdOx2 RabGP vaccine.

The destination vector structure is shown in FIG. 14. The amino acid sequence of the rabies glycoprotein is provided in SEQ ID NO. 21.

Vaccine was diluted in PBS prior to administration, and in some cases were mixed with squalene oil-in-water adjuvant (Addavax, Sigma). 6 week old female CD1 outbred mice were immunised with the following formulations (n=6 mice/group), all given intramuscularly into each gastrocnemius.
A: ChAdOx2-RabGP, 1e8 infectivity units (IU)
B: ChAdOx2-RabGP, 1e7 IU
C: ChAdOx2-RabGP, 1e6 IU
D: ChAdOx2-RabGP, with Addavax, 1e8 IU
E: ChAdOx2-RabGP, with Addavax, 1e7 IU
F: ChAdOx2-RabGP, with Addavax, 1e6 IU Serum was collected 28 days after immunisation, and antibody titers were assessed by ELISA against a recombinant rabies glycoprotein (SAD B19 strain, lacking the transmembrane domain, with a C-terminal C-tag and purified using C-tag affinity resin [ThermoFisher]). Results were expressed in arbitrary units, relative to a dilution series/standard curve of a positive control sample, and $\log_{10}$ transformed prior to analysis.

Figure 15:
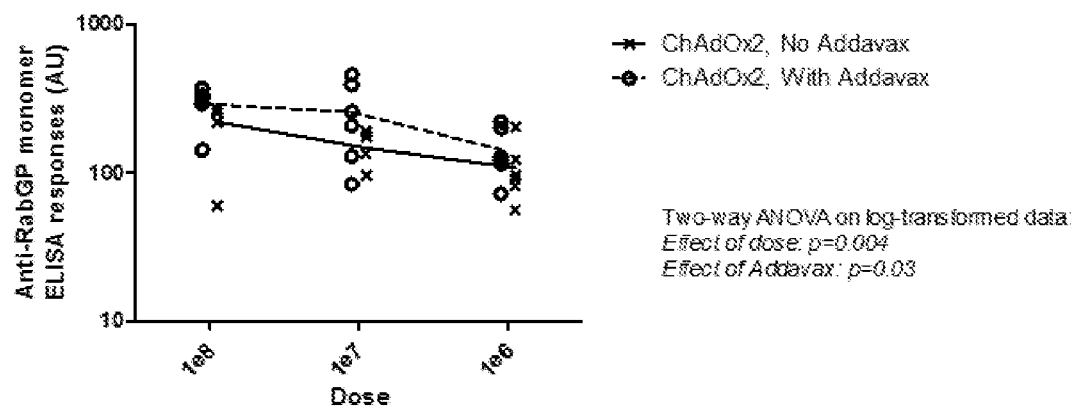
FIG. 15 shows the two-way ANOVA across the ChAdOx2 RabGP vaccine groups immunised with different doses with and without Addavax.

The vaccine induced ELISA-detectable antibody to the rabies glycoprotein, with statistically significant enhancements of antibody titer associated with rising vaccine dose and with co-formulation with Addavax. FIG. 15 shows antibody responses in mice vaccinated with ChAdOx2 RabGP at a range of doses, with and without adjuvant (groups A-F). $p=0.004$ for effect of dose and $p=0.03$ for effect of adjuvant co-formulation the two-way ANOVA across groups A-F.

A comparison of the immunogenicity of the ChAdOx2 vaccine construct with a AdC68 vaccine construct having the same antigen insert was made. The AdC68 was a kind gift of Hildegund Ertl, Wistar Institute, as disclosed in Xiang et al., Novel, Chimpanzee Serotype 68-based Adenoviral Vaccine Carrier for Induction of Antibodies to a Transgene Product, Journal of Virology, 76 (6), pp 2667-2675. The ChAdOx2 vaccine construct was surprisingly found to have higher immunogenicity than the AdC68 vaccine, as shown in FIG. 16.

REFERENCES

1. Buchbinder et al, Lancet, Vol 372, November 2008
2. Farina et al, J. Virol, December 2001, p 11603-11613
3. Dudareva et al, Vaccine 27, 2009, 3501-3504
4. R. Wigand et al, Intervirology, Vol 30; 1 1989
5. Roy et al, Hum. Gen. Ther., 2004, 15:519-530
6. Warming et al. Nuc. Acid. Res, 2005, Vol 33; 4
7. www.invitrogen.com/gateway
8. Havenga et al, J. G. V., 2006, 87, 2135-214
9. Warming, S. et al. Nucleic Acids Res, 2005, Feb. 24; 33(4): e36
10. Colloca, S., et al., Sci Transl Med, 2012. 4(115): p. 115ra2.
11. Quinn, K. M., et al. J Immunol, 2013. 190(6): p. 2720-35.

| SEQ ID NO. | List of Sequences<br>Description of sequence |
|---|---|
| 1 | Complete DNA sequence of C68 |
| 2 | E4 region of C68 |
| 3 | E4Orf1 from AdY25 |
| 4 | E4Orf2 from AdY25 |
| 5 | E4Orf3 from AdY25 |
| 6 | Complete DNA sequence of AdY25 |
| 7 | E4Orf4 from AdHu5 |
| 8 | E4Orf6 from AdHu5 |
| 9 | E4Orf6/7 from AdHu5 |
| 10 | ChAdOx2 vector (with Gateway cassette in E1 locus) |
| 11 | Nucleic acid sequence of *M. tuberculosis* protein Ag85A |
| 12 | Amino acid sequence of *M. tuberculosis* protein Ag85A |
| 13 | Nucleic acid sequence of nucleoprotein (NP) and matrix protein 1 (M1) from influenza A virus |
| 14 | Amino acid sequence of nucleoprotein (NP) and matrix protein 1 (M1) from influenza A virus |
| 15 | Linker sequence |
| 16 | E1 region of C68 |
| 17 | E3 region of C68 |
| 18 | Amino acid sequence of C68 hexon protein |
| 19 | Amino acid sequence of C68 penton protein |
| 20 | Amino acid sequence of C68 fibre protein |
| 21 | Amino acid sequence of the rabies glycoprotein |

The invention claimed is:

1. An adenoviral vector comprising:
genome of an adenovirus other than AdHu5 and AdY25, wherein the genome of the adenovirus has been modified such that the vector lacks native E4 locus of the adenovirus and comprises heterologous E4Orf1, E4Orf2 and E4Orf3 coding regions from AdY25, and heterologous E4Orf4, E4Orf6 and E4Orf6/7 coding regions from AdHu5 in the E4 locus of the adenovirus.

2. The adenoviral vector of claim 1, wherein said adenovirus is C68.

3. The adenoviral vector of claim 1, wherein said adenoviral vector lacks a functional E1 locus or E3 locus.

4. The adenoviral vector of claim 1, wherein said adenoviral vector comprises one or more capsid proteins selected from the group consisting of:
   (a) a hexon protein encoded by coding sequence corresponding to nucleotides 18315 to 21116 of SEQ ID NO. 1;
   (b) a penton protein encoded by coding sequence corresponding to nucleotides 13884 to 15488 of SEQ ID NO. 1; and
   (c) a fiber protein encoded by coding sequence corresponding to nucleotides 32134 to 33411 of SEQ ID NO. 1.

5. The adenoviral vector of claim 1, further comprising an exogenous nucleotide sequence of interest that encodes a protein or polypeptide.

6. The adenoviral vector of claim 5, wherein said protein or polypeptide is selected from the group comprising an antigen, a molecular adjuvant, an immunostimulatory protein or a recombinase.

7. The adenoviral vector of claim 6, wherein the antigen is a pathogen-derived antigen.

8. The adenoviral vector of claim 7, wherein the pathogen is selected from the group consisting of *M. tuberculosis*, *Plasmodium* spp, influenza virus, HIV, Hepatitis C virus, Cytomegalovirus, Human papilloma virus, rabies virus, measles virus, mumps, rubella, zika virus, *leishmania* parasites, *Mycobacterium* spp, and *Mycobacterium avium* subspecies paratuberculosis (MAP).

9. The adenoviral vector of claim 8, wherein the antigen is rabies virus glycoprotein.

10. The adenoviral vector of claim 5, wherein said exogenous nucleotide sequence of interest is a miRNA or immunostimulatory RNA sequence.

11. An immunogenic composition comprising the adenovirus vector according to claim 1 and optionally one or more additional active ingredients, a pharmaceutically acceptable carrier, diluent, excipient or adjuvant.

12. A polynucleotide sequence encoding the adenoviral vector of claim 1.

13. A host cell transduced with the adenoviral vector of claim 1.

14. A method of producing the adenoviral vector of claim 1, comprising the step of incorporating a polynucleotide sequence encoding said adenoviral vector into a Bacterial Artificial Chromosome (BAC) to produce an Ad-BAC vector.

15. A Bacterial Artificial Chromosome (BAC) clone comprising the polynucleotide sequence of claim 12.

16. A packaging cell line producing the viral vector of claim 1.

17. The packaging cell line of claim 16, wherein said cell comprises complement of any genes functionally deleted in the viral vector of claim 1.

18. A kit comprising: (i) one of an adenoviral vector according to claim 1 or an immunogenic composition comprising the adenoviral vector according to claim 1, and (ii) instructions for use.

19. A method of treating or preventing a disease comprising administering the immunogenic composition according to claim 11 to a subject in need thereof.

20. The method of claim 19, wherein the disease is selected from the group comprising tuberculosis, Johne's disease, Crohn's disease, malaria, influenza, HIV/AIDS, Hepatitis C virus infection, Cytomegalovirus infection, Human papilloma virus infection, adenoviral infection, leishmaniasis, *Streptococcus* spp infection, *Staphylococcus* spp infection, *Meningococcus* spp infection, foot and mouth disease, chikungunya virus infection, Zika virus infection, rabies, Crimean Congo haemorrhagic fever, Ebola virus infection, Marburg, Lassa fever, MERS and SARS coronavirus disease, and Nipah and Rift Valley fever.

21. The method of claim 19, wherein the method comprises delivering a transgene into a host cell of the subject.

* * * * *